(12) United States Patent
Sabbisetti et al.

(10) Patent No.: US 10,712,349 B2
(45) Date of Patent: Jul. 14, 2020

(54) CIRCULATING KIM-1 LEVELS FOR DETECTION OF PATHOLOGIES ASSOCIATED WITH INJURY TO, OR CANCER OF, THE KIDNEY

(71) Applicant: THE BRIGHAM AND WOMEN'S HOSPITAL, INC., Boston, MA (US)

(72) Inventors: Venkata S. Sabbisetti, Brighton, MA (US); Joseph V. Bonventre, Wayland, MA (US)

(73) Assignee: THE BRIGHAM AND WOMEN'S HOSPITAL, INC., Boston, MA (US)

( * ) Notice: Subject to any disclaimer, the term of this patent is extended or adjusted under 35 U.S.C. 154(b) by 0 days.

(21) Appl. No.: 15/303,883

(22) PCT Filed: Apr. 14, 2015

(86) PCT No.: PCT/US2015/025746
§ 371 (c)(1),
(2) Date: Oct. 13, 2016

(87) PCT Pub. No.: WO2015/160805
PCT Pub. Date: Oct. 22, 2015

(65) Prior Publication Data
US 2017/0122966 A1 May 4, 2017

Related U.S. Application Data

(60) Provisional application No. 61/979,587, filed on Apr. 15, 2014, provisional application No. 62/007,998, filed on Jun. 5, 2014.

(51) Int. Cl.
*G01N 33/68* (2006.01)
*G01N 33/574* (2006.01)
*A61K 31/00* (2006.01)

(52) U.S. Cl.
CPC ......... *G01N 33/6893* (2013.01); *A61K 31/00* (2013.01); *G01N 33/57438* (2013.01); *G01N 2333/705* (2013.01); *G01N 2800/347* (2013.01)

(58) Field of Classification Search
None
See application file for complete search history.

(56) References Cited

U.S. PATENT DOCUMENTS

| | | | |
|---|---|---|---|
| 7,300,652 B2 | 11/2007 | Bailly | |
| 2006/0008804 A1 | 1/2006 | Chibout et al. | |
| 2006/0009904 A1 | 1/2006 | Sakashita | |
| 2007/0254370 A1 | 11/2007 | Devarajan | |
| 2008/0064047 A1 | 3/2008 | Zetter | |
| 2008/0124336 A1 | 5/2008 | Bailly | |
| 2009/0306625 A1* | 12/2009 | Pereira-Kamath | A61B 5/412 604/509 |
| 2011/0287964 A1 | 11/2011 | Bonventre | |
| 2015/0219660 A1* | 8/2015 | Meseguer Navarro | G01N 33/57438 435/7.1 |

FOREIGN PATENT DOCUMENTS

WO  WO-2015077676 A1 * 5/2015 ......... G01N 33/6893

OTHER PUBLICATIONS

Meso Scale Discovery (pp. 1 and 2, Apr. 2012).*
Adiyanti et al., "Acute kidney injury (AKI) biomarker" Acta Med Indones 44(3) 246-255 (2012).
Basile et al., "Renal ischemic injury results in permanent damage to peritubular capillaries and influences long-term function", Am J Physiol Renal Physiol 281(5) F887-F899 (2001).
Bonventre, "Kidney Injury Molecule-1 (KIM-1): A specific and sensitive biomarker of kidney injury" Scand J Clin Lab Invest Suppl, 68(S241) 78-83 (2008).
Bonventre et al., "Kidney injury molecule-1 (KIM-1): a urinary biomarker and much more", Nephrol Dial Transplant 24(11) 3265-3268 (2009).
Bonventre et al., "Next-generation biomarkers for detecting kidney toxicity", Nat Biotechnol 28(5) 436-440 (2010).
Bonventre et al., "Can We Target Tubular Damage to Prevent Renal Function Decline in Diabetes?", Semin Nephrol 32(5) 452-462 (2012).
Bonventre et al., "AKI: A Path Forward", Clin J Am Soc Nephrol 8(9) 1606-1608 (2013).
Cerda et al., "In severe acute kidney injury, a higher serum creatinine is paradoxically associated with better patient survival", Nephrol Dial Transplant, 22(10) 2781-2784 (2007).
Chaturvedi et al., "Assay Validation for KIM-1: human urinary renal dysfunction biomarker", Int J Biol Sci 5(2) 128-134 (2009).
Chen et al., "Increased susceptibility of aging kidney to ischemic injury: identification of candidate genes changed during aging, but corrected by caloric restriction" Am J Physiol Renal Physiol, 293(4):F1272-F1281 (2007).
Coca et al., "Biomarkers for the diagnosis and risk stratification of acute kidney injury: a systematic review", Kidney International 73(9) 1008-1016 (2008).

(Continued)

*Primary Examiner* — Alana Harris Dent
(74) *Attorney, Agent, or Firm* — Nixon Peabody LLP; David S. Resnick; Susanna C. Benn

(57) ABSTRACT

The present invention is directed to KIM-1 polypeptide as a plasma acute and chronic kidney injury and renal cell carcinoma biomarker, and methods and kits comprising the use of agents specific to KIM-1 for facilitating and enhancing the diagnosis of kidney injury or carcinoma. The present invention is based on the discovery that measuring KIM-1 levels in the blood is more accurate and reliable than measuring KIM-1 levels in the urine for the diagnosis of subjects with proximal kidney tubule injury or kidney cancer. The invention is directed to methods for diagnosis of acute kidney injury, chronic kidney disease (CKD), and renal cell cancer by determining and monitoring the levels of KIM-1 polypeptide in a blood sample, such as plasma or serum sample.

19 Claims, 24 Drawing Sheets

Specification includes a Sequence Listing.

(56) References Cited

OTHER PUBLICATIONS

Conti et al., "Urinary cystatin C as a specific marker of tubular dysfunction", Clin Chem Lab Med, 44(3):288-291 (2006).
Dieterle et al., "Renal biomarker qualification submission: a dialog between the FDA-EMEA and Predictive Safety Testing Consortium", Nat Biotechnol 28(5) 455-462 (2010).
Fahmy et al., "Urinary Expression of Novel Tissue Markers of Kidney Injury after Ureteroscopy, Shockwave Lithotripsy, and in Normal Healthy Controls", J Endourol 27(12) 1455-1462 (2013).
Feigelstock et al., "The Human Homolog of HAVcr-1 Codes for a Hepatitis A Virus Cellular Receptor", J Virol 72(8) 6621-6628 (1998).
Fliser et al., "Advances in Urinary Proteome Analysis and Biomarker Discovery", J Am Soc Nephrol, 18(4) 1057-1071 (2007).
Foster et al., "Urinary Biomarkers and Risk of ESRD in the Atherosclerosis Risk in Communities Study", Clin J Am Soc Nephrol 10(11) 1956-1963 (2015).
Grgic et al., "Targeted proximal tubule injury triggers interstitial fibrosis and glomerulosclerosis", Kidney Int 82(2) 172-183 (2012).
Han et al., "Kidney Injury Molecule-1 (KIM-1): A novel biomarker for human renal proximal tubule injury", Kidney Int, 62(1) 237-244 (2002).
Han et al., "Human Kidney Injury molecule-1 is a Tissue and Urinary Tumor Marker of Renal Cell Carcinoma", J Am Soc Nephrol 16(4) 1126-1134 (2005).
Han et al., "Urinary biomarkers in the early diagnosis of acute kidney injury", Kidney Int., 73(7) 863-869 (2008).
Hanley et al., "A Method of Comparing the Areas under Receiver Operating Characteristic Curves Derived from the Same Cases", Radiology 148(3) 839-843 (1983).
Herget-Rosenthal et al., "Prognostic Value of Tubular Proteinuria and Enzymuria in Nonoliguric Acute Tubular Necrosis", Clin Chem, 50(3) 552-558 (2004).
Huang et al., "The Clinical Utility of Kidney Injury Molecule 1 in the Prediction, Diagnosis and Prognosis of Acute Kidney Injury: A Systematic Review", Inflamm Allergy Drug Targets 10(4) 260-271 (2011).
Humphreys et al., "Chronic epithelial kidney injury molecule-1 expression causes murine kidney fibrosis", J ClinInvest 123(9) 4023-4035 (2013).
Huo et al., "Kidney injury molecule-1 (KIM-1): a novel kidney-specific injury molecule playing potential double-edged functions in kidney injury", Transplantation Reviews 24(3) 143-146 (2010).
Ichimura et al., "Kidney Injury Molecule-1 (KIM-1), a Putative Epithelial Cell Adhesion Molecule Containing a Novel Immunoglobulin Domain, is Up-regulated in Renal Cells after injury", J Biol Chem, 273(7) 4135-4142 (1998).
Ichimura et al., "Kidney injury molecule-1: a tissue and urinary biomarker for nephrotoxicant-induced renal injury", Am J Physiol Renal Phisiol 286(3) F552-F563 (2004).
Ichimura et al., "Kidney injury molecule-1 is a phosphatidylserine receptor that confers a phagocytic phenotype on epithelial cells", J Clin Invest 118(5) 1657-1668 (2008).
Ishani et al., "Acute Kidney Injury Increases Risk of ESRD among Elderly", J Am Soc Nephrol 20(1) 223-228 (2009).
Jefferson et al., "Proteinuria in diabetic kidney disease: A mechanistic viewpoint", Kidney International 74(1) 22-36 (2008).
Kang et al., "Role of the Microvascular Endothelium in Progressive Renal Disease", J Am Soc Nephrol 13(2) 806-816 (2002).
Khosrotehrani et al., "Fetal cells participate over time in the response to specific types of murine maternal hepatic injury", Hum Reprod 22(3) 654-661 (2007).
Khwaja, "KDIGO Clinical Practice Guidelines for Acute Kidney Injury", Nephron Clin Pract 120, 179-184 (2012).
Kim et al., "Vascular endothelial growth factor (VEGF) and soluble VEGF receptor FLT-1 in diabetic nephropathy", Kidney Int, 67(1):167-77 (2005).
Kobayashi et al., "TIM-1 and TIM-4 Glycoproteins Bind Phosphatidylserine and Mediate Uptake of Apoptotic Cells", Immunity 27(6) 927-940 (2007).

Lafrance et al., "Acute Kidney Injury Associates with Increased Long-Term Mortality", J Am Soc Nephrol 21(2) 345-352 (2010).
Latif et al., "Identification of the von Hippel-Lindau Disease Tumor Suppressor Gene", Science 260(5112) 1317-1320 (1993).
Lattanzio et al., "Acute Kidney Injury: New Concepts in Definition, Diagnosis, Pathophysiology, and Treatment", The Journal of the American Osteopathic Association 109(1) 13-19 (2009).
Liangos et al., "Urinary N-Acetyl-Beta-(D)-Glucosaminidase Activity and Kidney Injury Molecule-1 Level Are Associated with Adverse Outcomes in Acute Renal Failure", J Am Soc Nephrol, 18(3):904-12 (2007).
Liangos et al., "Comparative Analysis of Urinary Biomarkers for Early Detection of Acute Kidney Injury Following Cardiopulmonary Bypass", Biomarkers 14(6) 423-431 (2009).
Matz et al., "Early post-transplant urinary IP-10 expression after kidney transplantation is predictive of short- and long-term graft function", Kidney Int, 69(9) 1683-1690 (2006).
Mauer et al., "Structureal-Funcional Relationships in Diabetic Nephropathy", J Clin Invest 74(4) 1143-1155 (1984).
Miyanishi et al., "Identification of Tim4 as a phosphatidylserine receptor", Nature 450(7168) 435-439 (2007).
Myers et al., "Transtubular leakage of glomerular filtrate in human acute renal failure", Am J Physiol 237(4) 319-325 (1979).
Nangaku et al., "Chronic Hypoxia and Tubulointerstitial Injury: A Final Common Pathway to End-Stage Renal Failure", J Am Soc Nephrol 17(1) 17-25 (2006).
Nguyen et al.,"Biomarkers for the early detection of acute kidney injury", Pediatr Nephrol, 23(12) 2151-2157 (2008).
Owen et al., "Dose of Hemodialysis and Survival: Differences by Race and Sex", JAMA, 280(20) 1764-1768 (1998).
Palevsky et al., "KDOQI US Commentary on the 2012 KDIGO Clinical Practice Guideline for Acute Kidney Injury", Am J Kidney Dis 61(5) 649-672 (2013).
Parikh et al., "Urine IL-18 is an Early Diagnostic Marker for Acute Kidney Injury and Predicts Mortality in the Intensive Care Unit", J Am Soc Nephrol, 16(10) 3046-3052 (2005).
Peng et al., "Non-invasive Detection of Acute Renal Allograft Rejection by Measurement of Vascular Endothelial Growth Factor in Urine", J Int Med Res, 35(4) 442-449 (2007).
Peralta et al., "Associations of Urinary Levels of Kidney Injury Molecule-1 (KIM-1) and Neutrophil Gelatinase-Associated Lipocalin (NGAL) With Kidney Function Decline in the Multi-Ethnic Study of Atherosclerosis (MESA)", Am J Kidney Dis 60(6) 904-911 (2012).
Rees et al., "Kim-1/Tim-1: from biomarker to therapeutic target?", Translational Nephrology 23(11) 3394-3396 (2008).
Rennert, "Novel roles for TIM-1 in immunity and infection", Immunol Lett 141(1) 28-35 (2011).
Rifai et al., "Protein biomarker discovery and validation: the long and uncertain path to clinical utility", Nat Biotechnol, 24(8) 971-983 (2006).
Ronco et al., "Improving outcomes from acute kidney injury (AKI): Report on an initiative", The International Journal of Artificial Organs 30(5) 373-376 (2007).
Rosolowsky et al., "Risk for ESRD in Type 1 Diabetes Remains High Despite Renoprotection", J Am Soc Nephrol 22(3) 545-553 (2011).
Ruster et al., "The Role of chemokines and chemokine receptors in diabetic nephropathy", Front Biosci, 13, 944-955 (2008).
Sabbisetti et al., "Blood Kidney Injury Molecule-1 Is a Biomarker of Acute and Chronic Kidney Injury and Predicts Progression to ESRD in Type 1 Diabetes", J Am Soc Nephrol 25, 2177-2186 (2014).
Sabbisetti et al., Abstract 5195: "Kidney injury molecule-1: a novel therapeutic target in renal cell carcinoma", Proceedings: AACR 104th Annual Meeting Apr. 6-10, 2013: Molecular and Cellular Biology 73(8) (2013).
Sabbisetti et al., "Novel Assays for Detection of Urinary KIM-1 in Mouse Models of Kidey Injury", Toxicological Sciences 131(1) 13-35 (2013).

(56) References Cited

OTHER PUBLICATIONS

Sangoi et al., "Evaluation of Putative Renal Cell Carcinoma Markers PAX-2, PAX-8, and hKIM-1 in Germ Cell Tumors: A Tissue Microarray Study of 100 Cases", Appl Immunohistochem Mol Morphol 20(5) 451-453 (2012).
Shao et al., "Diagnostic Value of Urinary Kidney Injury Molecule 1 for Acute Kidney Injurt: A Meta-Analysis", PLoS One 9(1) e84131 (2014).
Skupien et al., "The early decline in renal function in patients with type 1 diabetes and proteinuria predicts the risk of end-stage renal disease", Kidney Int 82(5) 589-597 (2012).
Slocum et al., "Marking Renal Injury: Can We Move Beyond Serum Creatinine?", Transl Res 159(4) 277-289 (2012).
Sutton et al., "Microvascular endothelial injury and dysfunction during ischemic acute renal failure", Kidney International 62(5) 1539-1549 (2002).
Sutton et al., "Alteration of microvascular permeability in acute kidney injury", Microvasc Res 77(1) 4-7 (2009).
Taman et al., "Increased urinary hepatocyte growth factor excretion in human acute renal failure", Clin Nephrol, 48(4) 241-245 (1997).
Tang et al., "The pathogenic role of the renal proximal tubular cell in diabetic nephropathy", Nephrol Dial Transplant 27(8) 3049-3056 (2012).
Tatapudi et al., "Noninvasive detection of renal allograft inflammation by measurements of mRNA for IP-10 and CXCR3 in urine" Kidney Int, 65(6) 2390-2397 (2004).
Timmeren et al., "Tubular kidney injury molecule-1 (KIM-1) in human renal disease", Journal of Pathology 212(2) 209-217 (2007).
U.S. Food and Drug Administration: FDA, European Medicines Agency to Consider Additional Test Results When Assessing New Drug Safety: Collaborative effort by FDA and EMEA expected to yield additional safety data. 2008. Available at: http://www.fda.gov/.
Uchida et al., "Measurement of cystatin-C and creatinine in urine", Clin Chim Acta, 323(1-2) 121-8 (2002).
Vaidya et al., "Mechanistic biomarkers for cytotoxic acute kidney injury", Expert Opin Drug Metab Toxicol, 2(5) 697-713 (2006).
Vaidya et al., "Urinary kidney injury molecule-1: a sensitive quantitative biomarker for early detection of kidney tubular injury", Am J Physiol Renal Physiol, 290(2) F517-F529 (2006).
Vaidya et al., "Biomarkers of Acute Kidney Injury" Annu Rev Pharmacol Toxicol, 48, 463-493 (2008).
Vaidya et al., "Urinary Biomarkers for Sensitive and Specific Detection of Acute Kidney Injury in Humans", Clin Transl Sci, 1(3) 200-208 (2008).
Vaidya et al., "Kidney Injury Molecule-1 Outperforms Traditional Biomarkers of Kidney Injury in Multi-site Preclinical Biomarker Qualification Studies", Nat Biotechnol 28(5) 478-485 (2010).
Vallon, "The proximal tubule in the pathophysiology of the diabetic kidney", Am J Physiol Regul Integr Comp Physiol 300(5) R1009-R1022 (2011).
Van Timmeren et al., "Tubular kidney injury molecule-1 in protein-overload nephropathy", Am J Physiol Renal Physiol 291(2) F456-F464 (2006).
Waanders et al., "Kidney injury molecule-1 in renal disease", J Pathol 222(1) 7-16 (2010).
Waikar et al., "Biomarkers for the Diagnosis of Acute Kidney Injury", Nephron Clin Pract, 109(4) c192-c197 (2008).
Waikar et al., "Imperfect Gold Standards for Kidney Injury Biomarker Evaluation", J Am Soc Nephrol 23(1) 13-21 (2012).
Waikar et al., "Normalization of urinary biomarkers to creatinine during changes in glomerular filtration rate", Kidney Int, 78(5) 486-494 (2010).
Wald et al., "Chronic Dialysis and Death Among Survivors of Acute Kidney Injury Requiring Dialysis", JAMA 302(11) 1179-1185 (2009).
Webb et al., "ARF, ATN or AKI? It's now acute kidney injury", Anaesthesia and intensive care 35(6) 843-845 (2007).
Westhuyzen et al., "Measurement of tubular enzymuria facilitates early detection of acute renal impairment in the intensive care unit", Nephrol Dial Transplant, 18(3) 543-551 (2003).
White et al., "Type 2 Diabetic Patients with Nephropathy Show Structural-Functional Relationships that Are Similar to Type 1 Disease", J Am Soc, 11:1667-1673 (2000).
Yang et al., "Epithelial cell cycle arrest in G2/M mediates kidney fibrosis after injury", Nat Med 16(5) 535-543 (2010).

* cited by examiner

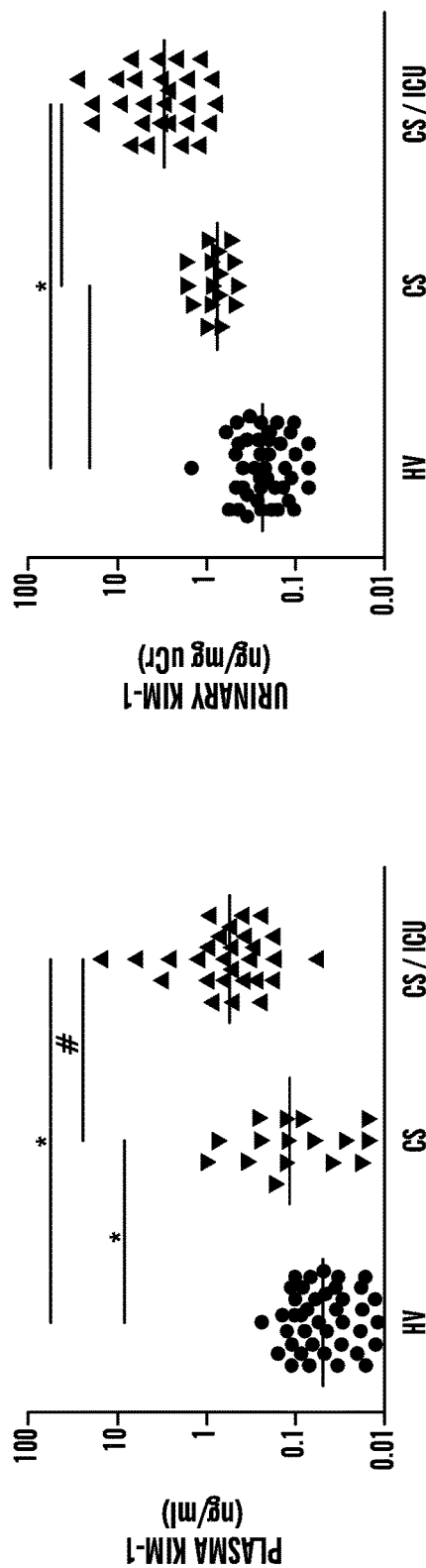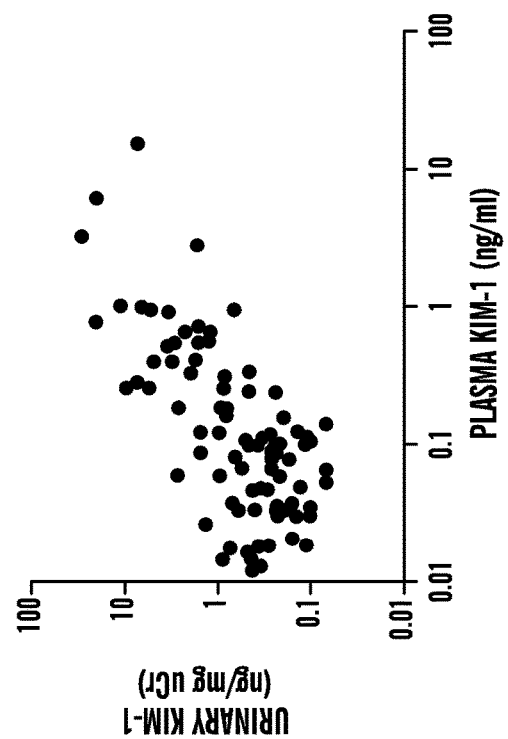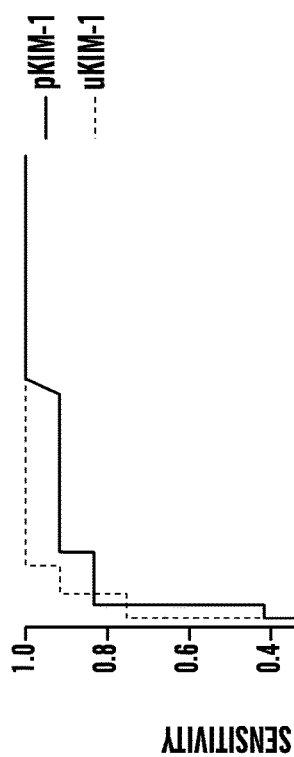
FIG. 2A  FIG. 2B  FIG. 2C  FIG. 2D

CIRCULATING KIM-1 LEVELS FOR DETECTION OF PATHOLOGIES ASSOCIATED WITH INJURY TO, OR CANCER OF, THE KIDNEY

CROSS REFERENCE TO RELATED APPLICATIONS

This application is a 371 National Phase Entry of International Patent Application No. PCT/US2015/025746 filed on Apr. 14, 2015 which claims benefit under 35 U.S.C. § 119(e) of U.S. Provisional Patent Application Ser. No. 61/979,587 filed on Apr. 15, 2014, and Provisional Patent Application Ser. No. 62/007,998 filed on Jun. 5, 2014, the contents of which are incorporated herein in their entirety by reference.

GOVERNMENT SUPPORT

This work was made with Government support under Grant No. DK39773,DK072381, DK075941, RC2 GM093080, U01-DK85660 and DK041526 awarded by the National Institutes of Health. The Government has certain rights to the invention.

SEQUENCE LISTING

The sequence listing of the present application has been submitted electronically via EFS-Web as an ASCII formatted sequence listing with a file name "043214-081461-PCT SL", creation date of Oct. 3, 2016 and a size of 12,872. The sequence listing submitted via EFS-Web is part of the specification and is herein incorporated by reference in its entirety.

FIELD OF THE INVENTION

The present invention relates generally to the use of Kidney Injury Molecule-1 (KIM-1) as a plasma biomarker for sensitive and specific detection of acute kidney injury (AKI), chronic kidney disease (CKD), end stage renal disease (ESRD) and Renal cell carcinoma (RCC) in subjects, including subjects with diabetes and proteinuria, as well as for detecting disease progression and severity of injury to the kidney in humans by assessing the levels of KIM-1 protein in the blood or plasma of human subjects.

BACKGROUND OF THE INVENTION

Acute kidney injury (AKI) is a common and serious condition recognized in nearly all fields of medical practice. It is characterized as a rapid and intensive decline of renal function associated with series of clinical syndrome which account for high morbidity and mortality (Ronco et al. (2007) Improving outcomes from acute kidney injury (AKI): Report on an initiative. Int J Artif Organs 30: 373-376), Webb S et a., (2007) ARF, ATN or AKI? It's now acute kidney injury. Anaesth Intensive Care 35: 843-844). The mortality rate in hospital intensive care units ranges from 40% to 80%. Furthermore, Acute kidney injury (AKI) predisposes patients to the development of both chronic kidney disease and end-stage renal failure. AKI is characterized by a rapid decline in kidney function, often triggered by an ischemic or toxic insult. This clinical syndrome is associated with substantial short-term morbidity, mortality, and cost, but it had previously been assumed that patients surviving the episode made a full renal recovery. However, AKI is now appreciated to be markedly associated with increased risk of future chronic kidney disease (CKD), end-stage renal disease (ESRD) (Ishani A, et al., J Am Soc Nephrol. 2009; 20(1):223-228.; Wald R, et al., JAMA. 2009; 302(11):1179-1185.), and long-term mortality (Lafrance J P, Miller D R, J Am Soc Nephrol. 2010; 21(2):345-352.). The population rate of AKI is increasing at greater than 7% per year, and some estimates indicate that the incidence of AKI-related ESRD is equal to the incidence of ESRD from diabetes. The mechanisms that might explain the link between AKI and future CKD/ESRD are poorly understood, but peritubular capillary loss, a known consequence of AKI (Basile D P, et al., Am J Physiol Renal Physiol. 2001; 281 (5):F887-F899.), is proposed to lead to chronic hypoxia and later development of tubulointerstitial fibrosis and CKD (Kang D H, et al., J Am Soc Nephrol. 2002; 13(3):806-816; Nangaku M., J Am Soc Nephrol. 2006; 17(1):17-25). How chronic ischemia might trigger parenchymal loss at a molecular level is unresolved.

Acute kidney injury (AKI) predisposes patients to the development of both chronic kidney disease and end-stage renal failure, but the molecular details underlying this important clinical association remain obscure. AKI is characterized by a rapid decline in kidney function, often triggered by an ischemic or toxic insult. This clinical syndrome is associated with substantial short-term morbidity, mortality, and cost, but it had previously been assumed that patients surviving the episode made a full renal recovery. However, AKI is now appreciated to be markedly associated with increased risk of future chronic kidney disease (CKD), end-stage renal disease (ESRD) (Ishani A, et al., J Am Soc Nephrol. 2009; 20(1):223-228.; Wald R, et al., JAMA. 2009; 302(11):1179-1185.), and long-term mortality (Lafrance J P, Miller D R, J Am Soc Nephrol. 2010; 21(2):345-352).

Furthermore, diabetic nephropathy (DN) is the leading cause of end-stage renal disease (ESRD) in the United States and is epidemic worldwide. It is estimated that 33% of the US adult population will have diabetes by 2050. While proteinuria in diabetes has generally been attributed to abnormalities in the glomerulus, tubulointerstitial disease is the best indicator of functional progression of disease (Bonventre, J. V. Semin Nephrol 32, 452-462 (2012); Vallon, V., Am J Physiol Regul Integr Comp Physiol 300, R1009-1022 (2011); Tang, S. C. & Lai, K. N., Nephrol Dial Transplant 27, 3049-3056 (2012); Mauer, S. M., et al., J Clin Invest 74, 1143-1155 (1984); White, K. E. & Bilous, R. W., J Am Soc Nephrol 11, 1667-1673 (2000)). Tubular abnormalities may precede glomerular pathology early in DN (Jefferson, J. A., et al., Kidney Int 74, 22-36 (2008)). Pathological mechanisms that may initiate and/or mediate tubular epithelial injury and degeneration in DN remain, however, poorly understood. While current therapies that target hemodynamics in the glomerulus can slow disease progression, in most patients, DN is progressive, resulting in chronic kidney disease (CKD) and ESRD in approximately 30% of patients. A better understanding of the pathobiology and identification of novel therapeutic targets for the treatment of DN are desperately needed.

Early diagnosis and intervention of AKI and subjects at risk of ESRD could effectively prevent the occurrence of the outcome. Despite the advanced progress made in etiology and pathology of AKI, the clinical detection and diagnosis was still in controversy. Nowadays, the most widely used and commonly accepted clinical standard for the definition and diagnosis of AKI usually relies on the increase of serum creatinine or decrease of urine output which was proposed by both AKIN (acute kidney injury network), RIFLE (risk, injury, failure, loss, and ESRD) [Lattanzio et al., (2009) Acute kidney injury: new concepts in definition, diagnosis, pathophysiology, and treatment. J Am Osteopath Assoc 109: 13-19. 4)], and Kidney Disease Improving Global Outcomes (KDIGO) criteria. Unfortunately, due to the poor sensitivity and specificity and 48 h-72 h time needs, serum creatinine was incapable to comprehensively reflect the time and type of renal injury. Moreover, serum creatinine was also affected by some other factors, such as age, acute and chronic renal failure. These studies suggested that more accurate and efficient measure for AKI diagnosis was urgently required (Slocum J L, et al., (2012) Marking renal injury: can we move beyond serum creatinine? Transl Res 159: 277-289).

The lack of sensitive and specific kidney injury biomarkers greatly impedes the development of therapeutic strategies to improve outcomes of AKI. The traditional blood (creatinine, blood urea nitrogen) and urine markers of kidney injury (casts, fractional excretion of sodium, urinary concentrating ability), that have been used for decades in clinical studies for diagnosis and prognosis of AKI, are insensitive, nonspecific, and do not directly reflect injury to kidney cells. Outside of the clinical setting, the lack of specific AKI biomarkers has impeded the development of drugs and therapies that may improve the devastating outcomes of AKI. There is currently no plasma biomarker that specifically reflects kidney proximal tubule injury with high specificity.

Lines of evidence showed that urinary NGAL, IL-18, Cys-C, KIM-1 and some other candidate molecules were believed as potential urinary markers to diagnosis of AKI (Adiyanti S S (2012) Acute Kidney Injury (AKI) biomarker. Acta Med Indones 44: 246-255; Edelstein C L (2008) Biomarkers of acute kidney injury. Adv Chronic Kidney Dis 15: 222-234. But until now, none of them are currently established well enough to replace serum creatinine as a marker of renal function. Among these markers, growing evidence showed that KIM-1 performed significantly better in early detection of AKI than others, especially within 24 hours, well before serum creatinine increase, which made it possible to conduct prevention or treatment strategies at a very early stage of AKI (Liangos O, (2009) Comparative analysis of urinary biomarkers for early detection of acute kidney injury following cardiopulmonary bypass. Biomarkers 14: 423-431; Han W K, et al. (2008) Urinary biomarkers in the early diagnosis of acute kidney injury. Kidney Int 73: 863-869).

Kidney Injury Molecule-1 (KIM-1) is highly upregulated in dedifferentiated proximal tubular cells following kidney injury, and the ectodomain of KIM-1 is shed into the lumen and can be used as a urinary biomarker of kidney injury. Previous reports had proved KIM-1 in rat model to be an outstanding indicator of kidney proximal tubule injury, much better than serum creatinine (Ichimura T, (1998). KIM-1 is a putative epithelial cell adhesion molecule containing a novel immunoglobulin domain, and is markedly up-regulated in renal cells after injury. J Biol Chem 273: 4135-414213). Urinary KIM-1 levels are strongly related to tubular KIM-1 expression in experimental and in human renal disease [Waanders F, (2010) Kidney injury molecule-1 in renal disease. J Pathol 220: 7-1612]. Studies in humans indicated that urinary KIM-1 was sensitive and specific marker of injury as well as predictors of outcome [Bonventre J V (2008) Kidney Injury Molecule-1 (KIM-1): a specific and sensitive biomarker of kidney injury. Scand J Clin Lab Invest Suppl 241: 78-83]. Recently, two systematic reviews have reported that KIM-1 was an efficient novel urinary biomarker in diagnosis of AKI within 24 hours after kidney injury [Huang Y, (2011) The clinical utility of kidney injury molecule 1 in the prediction, diagnosis and prognosis of acute kidney injury: a systematic review. Inflamm Allergy Drug Targets 10: 260-271; Coca S G, (2008) Biomarkers for the diagnosis and risk stratification of acute kidney injury: a systematic review. Kidney Int 73: 1008-1016), especially in the diagnosis of ischemic ATN (Huang Y, 2011).

However, KIM-1 as a urinary biomarker for diagnosis of AKI was determined to be only 74% sensitive (Shao et al., (2014); PLOS, Diagnostic value of urinary kidney-injury molecule-1 for acute kidney injury: A Meta Analysis. 9(1); e84131)) when AKI was defined by an increase in serum creatinine. Furthermore, while spot urinary KIM-1 concentration normalized to urinary creatinine concentration is very attractive as a urinary biomarker given the stability of KIM-1 and the easy accessibility of urine specimens, there can be significant variability of urinary excretion over time in patients with AKI such that a spot collection may not be ideal under all circumstances (Waikar et al., (2010). Normalization of urinary biomarkers to creatinine during changes in glomerular filtration rate. Kidney Int 78(5):486-494). Thus, for urinary biomarkers to accurately detect kidney injury, it would be ideal to assay the biomarker from timed collection of urine samples in order to estimate renal excretion rate; however, this is not practical for routine clinical care. Hence, there remains an urgent need for more reliable sensitive biomarkers for detecting and monitoring kidney injury and AKI.

Another type of injury to the kidney is kidney or renal cancer. Kidney cancer is a heterogeneous disease consisting of various subtypes with diverse generic, biochemical and morphologic features. Renal cell carcinoma (RCC) accounts for 2-3% of adult malignancies and its incidence is increasing. RCC is not a uniform disease and is subdivided into clear cell, papillary, chromophobe and oncocytoma. The most common histological subtype of RCC is conventional RCC (also referred to as clear cell RCC or ccRCC), which accounts for 70-80% of all RCC cases. Based on morphological features defined in the WHO International Histological classification of Kidney Tumors, RCC can be divided into clear cell (conventional or ccRCC) (80%), papillary RCC (chromophil) (10-15%), chromophobe RCC (5%), collecting duct RCC (<1%) and unclassified RCC (<2%) subtypes. Many patients with von Hippel Lindau (VHL) disease, an autosomal dominant genetic disorder of inherited predisposition to RCC, also develop conventional RCC and studies on this familial disease facilitated the identification of the VHL tumor suppressor gene (Latif et al., Science, 1993; 260; 1317-1320).

The incidence of renal cell carcinoma (RCC) has steadily risen in the United States since 1970 and is currently estimated at approximately 51,000 cases per year. This increase has been observed across gender and race, increasing among black males and females by 3.9% and 4.3% per year, and white males and females by 2.3% and 3.1% per year, respectively. Typically, kidney organ confined RCC is treated with surgery and the five-year survival rate for patients presenting with Stage I disease is 95%, while the survival rate for patients with Stage II and III RCC is decreased to 70-80% and 40-60%, respectively. It is therefore reasonable to assume that early disease detection would improve overall survival in RCC patients.

RCC is a histological diverse disease, with variable and often unpredictable clinical behavior. The prognosis worsens dramatically with the onset of clinical metastasis and current regimens of systematic therapy yield only modest benefits for metastatic RCC. However, targeted therapy has opened a new set of possibilities and questions in RCC treatment. Tumor response by classical imaging criteria fails to reflect changes in tumor vessel density, tumor viability, or correlate with disease progression or even overall survival. The availability of biomarkers that reflect disease progression and severity as well as activity may therefore help guide therapy. Biomarkers that serve as surrogate markers of tumor response will expedite a large number of clinical trials in which kinase inhibitor are used in combination in patients both pre and post surgery. Treatment of patients with minimal residual disease may prove, now that effective therapies are available, to be a better approach than treatment following clinical detection. Adjuvant trials may target patients with biomarker-detected minimal residual disease after nephrectomy for the primary tumor.

Surgical resection is the mainstay of therapy for patients with localized primary tumors. However, new therapies are desperately needed for metastatic RCC, which is poorly responsive to chemotherapy and radiotherapy. Biomarkers could potentially be used to identify high-risk patients with localized RCC for early systemic therapy. Refining prognostic systems to more accurately predict patient outcomes and thereby guide more effective treatment decisions is an ongoing process. To date, key prognostic factors identified include TNM staging, tumor grade, functional status, and various biochemical assessments. Integrated prognostic systems combine clinical and pathological data in order to stratify patients and improve prognostic power. Additional biomarkers are likely to further increase prediction accuracy. Currently, there is no validated biomarker for renal cell cancer (RCC) such as PSA for prostate and CA125 for breast cancer. Currently there is no FDA approved marker for diagnosis of renal cell carcinoma.

Biomarker(s) that reliably correlate with disease burden or activity could be useful to detect disease before clinical signs and symptoms are apparent, even before there is radiological evidence of tumor growth. Such biomarkers can also be useful to guide early detection, such as techniques for detection of minimal residual disease (such as exploratory surgery or imaging), and could guide timing and choices of systemic therapy for relapsed or metastatic disease and can also be useful for the early identification of patients at need for adjuvant therapy after seemingly curative nephrectomy.

Such biomarkers could also be useful in the testing of potential therapeutic strategies for RCC. Surrogate markers of disease activity could also serve as surrogate endpoints in clinical trials and help shortening the length of a trial. Patients might avoid treatment with ineffective medications, thus preventing unnecessary side effect risks and serious complications. The may also be able to guide a physician to treat a patient with a more aggressive therapy where the level of the biomarker indicates a rapid progression of the RCC, and thus biomarkers for early diagnosis of RCC have the potential to guide therapeutic and preventive interventions, such as early administration of targeted/anti-angiogenic therapy, specialized imaging, exploratory surgery or chemoprevention trials. Unfortunately, reliable biomarkers for RCC have not been established yet.

SUMMARY OF THE INVENTION

Provided herein are methods, assays and kits for measuring Kidney Injury Molecule-1 (KIM-1) polypeptide as a sensitive and specific plasma biomarker for diagnosing and monitoring pathologies of injury to the kidney, including, subjects with acute kidney injury (AKI), chronic kidney disease (CKD), or end-stage renal disease (ESRD) and subjects with renal cell carcinoma (RCC).

The inventors have previously demonstrated that KIM-1 can be a urinary biomarker for AKI. There can be significant variability of urinary excretion over time in patients with AKI, and levels of KIM-1 in random or spot urine samples from subjects with AKI can be misleading due to time variation in excretion. For KIM-1 to be an ideal and accurate urine biomarker to detect kidney injury, it is necessary to measure the levels of KIM-1 from timed collection of urine samples to estimate renal excretion rate, which is not practical for routine clinical care. Thus, the use of KIM-1 as a urinary biomarker is limited due to its variability over time. Accordingly there is an urgent need for more accurate AKI biomarkers, especially ones that can provide an integrated measure that with a single measurement can indicate mean levels over time.

Herein, the inventors have now surprisingly discovered that, in addition to the ectodomain of KIM-1 being shed into the lumen of the kidney, KIM-1 is also released into the systemic circulation after kidney proximal tubule injury. Accordingly, the inventors have discovered that KIM-1 polypeptide is an accurate and sensitive plasma and serum circulating biomarker of kidney injury. The inventors demonstrate herein that in both rodent and human acute kidney injury (AKI) and human chronic kidney disease (CKD), increased levels of KIM-1 can be detected in the plasma and can serve as a circulating biomarker of kidney injury. This was surprising as KIM-1 polypeptide is expressed predominantly on the apical membrane of the proximal tubule epithelial cells and its ectodomain was previously believed to be released only into the urine on injury to the kidney, especially in milder forms of injury.

While U.S. Patent Application 2011/0287964 discloses using KIM-1 as a urinary biomarker in combination with a number of other urinary biomarkers for diagnosing a subject AKI, the present invention is directed to assessing levels of KIM-1 protein by itself in the blood for diagnosing a subject AKI, indicating how much epithelial cell injury is present, and predicting long term outcome of the kidney injury. Further, given that it has been reported that a single biomarker is rarely adequate to clearly define a particular pathologic state (Fliser et al., 18 J. Am. Soc. Nephrol. 1057-71 (2007); Rifai et al., 24 Nat. Biotech. 971-83 (2006)), it is surprising that levels of the KIM-1 polypeptide in the blood by itself is an accurate and sensitive plasma biomarker of AKI. The fact that measurement of blood levels of KIM-1 polypeptide by itself (and not with other blood biomarkers) can be used to reliably and accurately detect a subject with AKI is highly advantageous as it enables simple, quick and non-complex (e.g., not multiplex) assays to be used for the rapid and accurate diagnosis of a subject with AKI.

Herein, the inventors have developed sensitive assays to measure plasma KIM-1 in mouse, rat and human and demonstrated that plasma KIM-1 levels were elevated in a graded fashion with increasing periods of ischemia (10, 20 or 30 min) as early as 6 hr after reperfusion in mice and with gentamicin treatment (50 or 200 mg/kg for 10 days) in rats. In humans, plasma KIM-1 levels were higher in patients with acute kidney injury (AKI) than healthy controls or patients admitted to the ICU without AKI. The inventors discovered that in patients undergoing cardiopulmonary bypass, plasma KIM-1 levels increased within 2 days after surgery only in patients who developed AKI, and that blood KIM-1 levels were also elevated in patients with chronic kidney disease (CKD) of various etiologies, and correlated with stage of CKD. The inventors have also discovered that, in a cohort of patients with type 1 diabetes and proteinuria, serum KIM-1 level at baseline strongly predicted rate of eGFR loss and risk of end stage renal disease (ESRD) during 5-15 years of follow-up, even after adjustment for baseline urinary albumin-to-creatinine ratio, eGFR, and Hb1Ac.

Accordingly, the present invention is based on the discovery that blood levels of KIM-1 polypeptide can accurately and reliably detect AKI and CKD in subjects. Importantly, unlike measuring KIM-1 protein in the urine, blood KIM-1 protein levels can be measured in random blood samples, and does not require determination of the renal excretion rate of the subject, or normalization by urinary creatinine concentration.

Accordingly, the invention is directed to methods for diagnosis of AKI or CKD by determining and monitoring the levels of KIM-1 in a blood sample from the subject, e.g., where the blood sample can be any of; whole blood, plasma, serum or a fractionated blood sample. Further, the invention is directed to methods for facilitating the distinction of kidney infection from bladder infection in a subject. Accordingly, one embodiment of this aspect, and all aspects described herein, provides kidney injury molecule-1 (KIM-1), as a blood biomarker for kidney infection in patients exhibiting symptoms of bladder infection.

Herein, the inventors have also discovered that KIM-1 in the blood, e.g., in the plasma, is increased in subjects with ccRCC and papillary RCC, but not other types of RCC (e.g., chromophobe or oncocytoma (see FIG. 5A), and that increased levels of KIM-1 in the blood of subjects indicates a more severe tumor pathology (e.g., more severe tumor grade) as well as RCC metastasis (See e.g., FIGS. 6A-6B, and FIG. 11B-11D). Although KIM-1 levels are increased in the urine in patients with ccRCC (Bonventre (2009), Nephrol Dial Transplant, 24; 3265-3268; Han W K et al., (2005) Human kidney injury molecule-1 is a tissue and urinary tumor marker of renal cell carcinoma. J Am Soc Nephrol; 16: 1126-1134), it is more reliable for general use in detecting metastases and over all burden of tumor mass since the KIM-1 ectodomain may not get adequately filtered by the glomeruli of the kidney due to the size of the polypeptide. Furthermore when the tumor is located in the kidney the architecture of the kidney is distorted and hence KIM-1 may not readily get into the collecting system of the kidney and excreted into the urine. Thus, it is highly surprising that it is released into the blood, as KIM-1 polypeptide is expressed by tubular epithelium kidney cells, and it was previously believed that it was released only into the urine in subjects with RCC.

Accordingly, another aspect of the present invention is directed to methods, kits and compositions for diagnosis of Renal Cell Carcinoma (RCC), e.g., ccRCC, in a subject by detecting levels of KIM-1 in the blood sample obtained from a subject. Accordingly, aspects of the present invention provides compositions and methods for the diagnosis and prognosis of renal cell carcinoma (RCC) using blood, serum, or plasma levels of KIM-1 as a diagnostic test that is sensitive and specific. Plasma KIM-1 levels is useful for diagnosis and/or assessment of prognosis of clear cell RCC in a subject.

Another aspect of the present invention provides a method for monitoring the progression of RCC in a subject having, or a subject likely to develop, RCC, the method comprising: (a) measuring the level of KIM-1 polypeptide in a blood sample obtained from the subject, e.g., a plasma sample or serum sample at a first time point; (b) measuring the level of the level of KIM-1 polypeptide in a blood sample obtained from the subject at a second time point; and comparing the level of KIM-1 polypeptide from the first time point with the level of KIM-1 polypeptide from the second timepoint; wherein a change in the level of the KIM-1 polypeptide at the first time point as compared to the level of KIM-1 polypeptide at the second timepoint indicates an alteration in the rate of progression of RCC in the subject. In such embodiments, if a decrease in the level of KIM-1 polypeptidefrom the first timepoint as compared to the second timepoint, it indicates in improved prognosis of RCC progression at the second timepoint as compared to the first timepoint. Alternatively, if an increase in the level of the of KIM-1 polypeptide from the first timepoint as compared to the second timepoint indicates in decreased likelihood of RCC progression at the second timepoint as compared to the first timepoint.

In all such embodiments of this aspect and all aspects described herein, an agent specific for total protein or a normalizing protein, such as creatinine, may also be included, or an assay to measure the level or concentration of total protein or a normalizing protein may be performed in order to normalize the level or concentration of KIM-1 protein. Such normalization is often useful in order to permit various comparisons of KIM-1 blood levels, or determine ratios, for example, between subject samples, or between a series of samples isolated from the same subject at different timepoints (e.g., at a first timepoint and/or between any subsequent timepoint thereafter).

In one embodiment of the invention, KIM-1 protein biomarker levels present in a blood sample, such as plasma, whole blood or serum, are measured by contacting the test sample, or preparation thereof, with an agent, such as an antibody-based agent, that specifically binds to the KIM-1 polypeptide, e.g., to the ectodomain of KIM-1, wherein the agent forms a complex with the KIM-1 polypeptide which can be used in assays to determine KIM-1 protein concentration or level. Any means known to those skilled in art can be used to assess biomarker levels. For example, biomarker levels can be assessed by ELISA, multiplex bead assay, or mass spectrometry, including SELDI mass spectrometry. In some embodiments, the level of KIM-1 polypeptide in the blood sample can be determined by any method commonly known by person or ordinary skill in the art, for example where the protein expression is detected using an antibody, human antibody, humanized antibody, recombinant antibodies, monoclonal antibodies, chimeric antibodies, aptamer, peptide or analogues, or conjugates or fragments thereof. In some embodiments, KIM-1 protein levels in the blood sample are detected by use of protein-binding molecules, such as in methods such as ELISA, or multiplex immuno assays.

In some aspects, provided herein are assays comprising: (i) measuring in a blood sample obtained from a subject, a level of KIM-1 polypeptide; (ii) comparing the level of the KIM-1 polypeptide in the blood sample with a reference blood level of KIM-1 polypeptide; and (iii) identifying the subject as (a) having a kidney injury if the level of KIM-1 polypeptide is higher by a statistically significant amount than reference level; or (b) not having a kidney injury if the level of KIM-1 polypeptide not higher by a statistically significant amount than the reference level.

In some embodiments of these aspects and all such aspects described herein, the assay comprises identifying the subject as (a) having a kidney injury if the level of KIM-1 polypeptide is at least 4-fold above than reference level; or (b) not having a kidney injury if the level of KIM-1 polypeptide less than 4-fold above the reference level.

In some embodiments of these aspects and all such aspects described herein, the assay further comprises selecting the subject for an appropriate treatment for kidney disease.

In some embodiments of these aspects and all such aspects described herein, when the level of KIM-1 polypeptide is at least 4-fold above the reference level, the assay further comprises providing a treatment appropriate for treating kidney disease.

In some embodiments of these aspects and all such aspects described herein, the kidney injury is injury to the proximal tubule of the kidney or acute kidney injury (AKI).

In some embodiments of these aspects and all such aspects described herein, the kidney injury is chronic kidney disease (CKD) or where the kidney injury is early kidney injury which will progress into chronic kidney disease (CKD).

In some embodiments of these aspects and all such aspects described herein, the blood sample is obtained from a subject suspected to have a kidney disease or who has undergone a cardiopulmonary bypass (CBP).

In some embodiments of these aspects and all such aspects described herein, the blood sample is obtained from a subject who has type-1 diabetes or from a subject who has diabetic nephropathy.

In some embodiments of these aspects and all such aspects described herein, when the level of KIM-1 polypeptide is at least 5-fold above the reference level, the assay further comprises identifying the subject (c) at risk of developing end stage renal disease (ESRD) within 10 years; or (d) not at risk of developing end stage renal disease (ESRD).

Also provided herein in some aspects are assays comprising: (i) measuring in a blood sample obtained from a subject, a level of KIM-1 polypeptide; (ii) comparing the level of the KIM-1 polypeptide in the blood sample with a reference blood level of KIM-1 polypeptide; and (iii) identifying the subject as (a) having renal cell carcinoma (RCC) if the level of KIM-1 polypeptide is higher by a statistically significant amount than a reference level; or (b) not having RCC if the level of KIM-1 polypeptide is not higher by a statistically significant amount than the reference level.

In some embodiments of these aspects and all such aspects described herein, the assay comprises identifying the subject as (a) having a kidney injury if the level of KIM-1 polypeptide is at least 4-fold above than reference level; or (b) not having a kidney injury if the level of KIM-1 polypeptide less than 4-fold above the reference level.

In some embodiments of these aspects and all such aspects described herein, the level of KIM-1 polypeptide is measured using an agent which specifically binds to the KIM-1 polypeptide.

In some embodiments of these aspects and all such aspects described herein, the agent which specifically binds to the KIM-1 polypeptide is selected from an antibody, antibody fragment, or antigen-binding fragment of an antibody, or a protein-binding molecule.

In some embodiments of these aspects and all such aspects described herein, the antibody or is a polyclonal antibody, a chimeric antibody, an Fab, fragment, an F(ab')2 fragment, an Fab' fragment, an F sc fragment, or an Fv fragment.

In some embodiments of these aspects and all such aspects described herein, the agent which specifically binds to the KIM-1 polypeptide is immobilized on, or attached to, the surface of a solid support.

In some embodiments of these aspects and all such aspects described herein, the solid support surface is in the format of a dipstick, a test strip, paper-based assay, a latex bead, a microsphere, or a multi-well plate.

In some embodiments of these aspects and all such aspects described herein, the assay is automated or a high-throughput assay.

In some embodiments of these aspects and all such aspects described herein, the agent which specifically binds to the KIM-1 polypeptide comprises a detectable label, or wherein the agent can be bound by a secondary agent which comprises a detectable label.

In some embodiments of these aspects and all such aspects described herein, the detectable label is a fluorescent label.

In some embodiments of these aspects and all such aspects described herein, the assay is selected from an immunoassay, mass spectrometry, nuclear magnetic resonance spectrometry, and tandem mass spectrometry HPLC.

In some embodiments of these aspects and all such aspects described herein, the immunoassay is an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

In some embodiments of these aspects and all such aspects described herein, the KIM-1 polypeptide is human KIM-1 polypeptide.

In some embodiments of these aspects and all such aspects described herein, the blood sample is any of; a whole blood sample, a plasma sample, a serum sample or a fractionated blood sample.

In some aspects provided herein are methods for monitoring progression of kidney injury in a subject with a level of KIM-1 polypeptide in the blood at least 4-fold higher than a reference blood KIM-1 polypeptide level, the methods comprising: (a) measuring, at a first timepoint, a first level of KIM-1 polypeptide in a first blood sample obtained from the subject; (b) measuring, at a second timepoint, a second level of KIM-1 polypeptide in a second blood sample obtained from the subject; wherein the second timepoint is later than the first timepoint; (c) comparing the level of the KIM-1 polypeptide in the first blood sample with the level of the KIM-1 polypeptide in the first blood sample; and (d) identifying the subject as (a) having a more severe kidney injury at the second timepoint as compared to the first timepoint, where the level of KIM-1 polypeptide in the blood sample obtained at the second timepoint is above the level of KIM-1 polypeptide in the blood sample obtained at the first timepoint; or (b) having a less severe kidney at the second timepoint as compared to the first timepoint where the level of KIM-1 polypeptide in the blood sample obtained at the second timepoint is below the level of KIM-1 polypeptide in the blood sample obtained at the first timepoint.

In some embodiments of these aspects and all such aspects described herein, the method further comprises administering an appropriate treatment for kidney disease where the subject is identified to have a more severe kidney injury at the second timepoint.

Provided herein in some aspects are methods for monitoring treatment progress in a subject with kidney injury, the methods comprising: (a) measuring, at a first timepoint, a first level of KIM-1 polypeptide in a first blood sample obtained from the subject; (b) administering to the subject an appropriate therapeutic agent for treating kidney injury or RCC; and (c) measuring, at a second timepoint, a second level of KIM-1 polypeptide in a second blood sample obtained from the subject; wherein the second timepoint is later than the first timepoint and after said administering; and wherein if the second level of KIM-1 polypeptide is significantly lower than the first level, then the treatment is considered effective.

In some embodiments of these aspects and all such aspects described herein, the subject has a level of KIM-1 polypeptide in the blood at least 4-fold higher than a reference blood KIM-1 polypeptide level.

Provided herein in some aspects are methods for treating a subject with kidney disease comprising administering an appropriate therapy for kidney disease to the subject determined to have a level of KIM-1 polypeptide in the blood at least 4-fold above a reference blood KIM-1 polypeptide level.

Also provided herein are methods for treating a subject with RCC comprising administering an appropriate therapy for RCC to the subject determined to have a level of KIM-1 polypeptide in the blood at least 4-fold above a reference blood KIM-1 polypeptide level.

In some embodiments of these aspects and all such aspects described herein, the first blood sample and second blood sample is whole blood, plasma, serum or fractionated blood.

In some embodiments of these aspects and all such aspects described herein, the kidney injury is injury to the proximal tubule of the kidney, acute kidney injury (AKI), kidney disease or chronic kidney disease (CKD).

In some embodiments of these aspects and all such aspects described herein, the subject is suspected to have a kidney disease or who has undergone a cardiopulmonary bypass (CBP).

In some embodiments of these aspects and all such aspects described herein, the subject has type-1 diabetes.

In some embodiments of these aspects and all such aspects described herein, the level of KIM-1 polypeptide is measured using an agent which specifically binds to the KIM-1 polypeptide.

In some embodiments of these aspects and all such aspects described herein, the agent which specifically binds to the KIM-1 polypeptide is selected from an antibody, antibody fragment, or antigen-binding fragment of an antibody, or a protein-binding molecule.

In some embodiments of these aspects and all such aspects described herein, the antibody or is a polyclonal antibody, a chimeric antibody, an Fab, fragment, an F(ab')2 fragment, an Fab' fragment, an F sc fragment, or an Fv fragment.

In some embodiments of these aspects and all such aspects described herein, the agent which specifically binds to the KIM-1 polypeptide is immobilized on, or attached to, the surface of a solid support.

In some embodiments of these aspects and all such aspects described herein, the solid support surface is in the format of a dipstick, a test strip, paper-based assay, a latex bead, a microsphere, or a multi-well plate.

In some embodiments of these aspects and all such aspects described herein, the assay is automated or a high-throughput assay.

In some embodiments of these aspects and all such aspects described herein, the agent which specifically binds to the KIM-1 polypeptide comprises a detectable label, or wherein the agent can be bound by a secondary agent which comprises a detectable label.

In some embodiments of these aspects and all such aspects described herein, the detectable label is a fluorescent label.

In some embodiments of these aspects and all such aspects described herein, the assay is selected from an immunoassay, mass spectrometry, nuclear magnetic resonance spectrometry, and tandem mass spectrometry HPLC.

In some embodiments of these aspects and all such aspects described herein, the immunoassay is an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

In some embodiments of these aspects and all such aspects described herein, the KIM-1 polypeptide is human KIM-1 polypeptide.

In some embodiments of these aspects and all such aspects described herein, the subject is a mammal.

In some embodiments of these aspects and all such aspects described herein, the subject is a human.

In another aspect, the invention provides methods of optimizing therapeutic efficacy for treatment of acute kidney injury. Accordingly, in one embodiment of this aspect, the method comprises (a) measuring a level or concentration of kidney injury molecule-1 (KIM-1) protein (e.g., in some embodiments the ectodomain of KIM-1) in a blood sample from the subject, and (b) comparing the level or concentration of the KIM-1 protein with a reference level or concentration of KIM-1, wherein an increase in the level or concentration of KIM-1 protein in the blood sample relative to the reference level or concentration of KIM-1 protein indicates a need to administer to the subject a therapeutic treatment for acute kidney injury. In some embodiments, the blood sample is a plasma sample.

In another embodiment of this aspect, the method comprises contacting a blood sample obtained from a subject with at least one agent specific for kidney injury molecule-1 (KIM-1) polypeptide, (b) measuring a level or concentration of the KIM-1 polypeptide using an assay specific for the at least one agent; and (c) comparing the level or concentration of the KIM-1 polypeptide with a reference level or concentration of KIM-1 polypeptide, wherein an increase in the level or concentration of the KIM-1 polypeptide in the blood sample relative to the reference level or concentration of KIM-1 polypeptide indicates a need to administer to the subject a therapeutic treatment for acute kidney injury. In some embodiments, the blood sample is a plasma or serum sample.

In another aspect, the invention provides for kits for measuring KIM-1 protein in a blood sample. In some embodiments, the kit comprises at least one agent which specifically binds to the KIM-1 polypeptide, wherein binding of the agent to the KIM-1 polypeptide results in a detectable signal which indicates the level of KIM-1 polypeptide. In some embodiments, the agent which specifically binds to the KIM-1 polypeptide binds to the ectodomain of KIM-1 protein. In some embodiments, the agent which specifically binds to the KIM-1 polypeptide is labeled, e.g., with a fluorescent or other detectable label. In some embodiments, the kit comprises a container for holding a blood sample (e.g. plasma sample), and at least one agent, such as an antibody, that specifically binds to KIM-1 polypeptide, e.g., the ectodomain of KIM-1 polypeptide for use in determining the level, concentration or the presence of at KIM-1 polypeptide in the blood sample.

In one embodiment of this aspect, the kit comprises at least one antibody or antibody fragment or antigen-binding fragment of an antibody (e.g., antigen-binding Ab fragment), which specifically binds to human KIM-1 polypeptide. In some embodiments, the antibody or antibody fragment or antigen-binding fragment of an antibody binds to the ectodomain of human KIM-1 polypeptide. In some embodiments, the kit comprises an agent (e.g., a secondary detection agent), which is an antibody that can specifically bind to, and be used to detect the antibody, antibody fragment or antigen-binding antibody fragment which specifically binds to human KIM-1 polypeptide (also referred to as a "secondary antibody").

In some embodiments, the antibody, antibody fragment or antigen-binding Ab which specifically binds to human KIM-1 polypeptide is immobilized on a solid support. In some embodiments, where the antibody, antibody fragment or antigen-binding Ab which specifically binds to human KIM-1 polypeptide is immobilized on a solid support, the secondary antibody (e.g., antibody that can specifically bind to the antibody, antibody fragment or antigen-binding Ab fragment which specifically binds to human KIM-1 polypeptide) is detectably labeled. In alternative embodiment, the secondary antibody (e.g., antibody that can specifically bind to the antibody, antibody fragment or antigen-binding Ab fragment which specifically binds to human KIM-1 polypeptide) is immobilized on a solid support. In some embodiments, where the secondary antibody (e.g., antibody that can specifically bind to the antibody, antibody fragment or antigen-binding Ab fragment which specifically binds to human KIM-1 polypeptide) is immobilized on a solid support, the antibody, antibody fragment or antigen-binding Ab which specifically binds to human KIM-1 polypeptide is detectably labeled.

BRIEF DESCRIPTION OF THE DRAWINGS

The accompanying drawings, which are incorporated in and constitute a part of this specification, illustrate embodiments of the invention and, together with the description, serve to explain the objects, advantages, and principles of the invention.

FIG. 1A shows male BALB/c mice were subjected to 0 (sham), 10, 20, or 30 minutes of bilateral ischemia by clamping the renal pedicles for the time indicated. Urine, blood, and tissue were collected 24 hours after reperfusion. Periodic acid-Schiff staining of kidneysections indicated no injury in sham-operated mice, whereas loss of brush border, necrosis, and sloughing of cells into the tubular lumen were found in post-ischemic mice. FIG. 1B shows immunohistochemical staining of KIM-1 on kidney tissues obtained from sham-operated mice and mice that underwent 10,20, and 30 minutes of ischemia/reperfusion. FIG. 1C shows plasma creatinine and urinary and plasma KIM-1 in mice 24 hours after challenge with different durations of bilateral ischemia (n=6 per group). FIG. 1D shows plasma creatinine and urinary and plasma KIM-1 levels assessed in male BALB/c mice at different times after sham surgery or after reperfusion following 30 minutes of bilateral ischemia (n=6 per group). FIG. 1E shows male BALB/c mice that were subjected to unilateral ureteral obstruction (UUO). Urine and blood were collected on day 7 after UUO. Plasma creatinine, urinary KIM-1, and plasma KIM-1 were measured (n=4 per group) *P<0.001. FIG. 1F shows male BALB/c mice that were administered one dose of 10% CC14 (0.5 ml/kg). Mice were euthanized 48 hours after CC14 administration and evaluated for liver (upper two panels) or kidney (lower two panels) toxicity by histopathology after periodic acid-Schiff staining (n=3 per group). FIG. 1G shows plasma creatinine, normalized urinary KIM-1, or plasma KIM-1 concentration in vehicle (Veh) and CC14-treated mice (n=3 per group) *P<0.001. FIG. 1H shows male Sprague-Dawley rats that were administrated 0.9% saline or 50 or 200 mg/kg gentamicin daily for 10 days and euthanized on day 11. Hematoxylin and eosin staining of kidney sections revealed no injury in vehicle-treated rats, whereas there were loss of brush border, necrosis, and sloughing of cells into the tubular lumen in gentamicin-treated rats. Tubular necrosis score (FIG. 1I), plasma creatinine (FIG. 1J), urinary KIM-1 normalized to urine creatinine (FIG. 1K), and plasma KIM-1 (FIG. 1L) is shown in rats administrated gentamicin at 0, 50, or 200 mg/kg per day for 10 days. *P<0.001, # P<0.05; n=5). Scale bars, 50 m. Error bars reflect SEM.

FIGS. 2A-2J show plasma KIM-1 is a marker of renal injury in human AKI. Plasma and urine were collected from healthy volunteers and post-cardiac surgery (CS) patients with or without AKI and ICU patients with AKI from other causes. FIG. 2A shows a dot plot for plasma KIM-1 normalized to urinary creatinine for each patient. FIG. 2B shows a dot plot for urinary KIM-1 normalized to urinary creatinine for each patient. *P<0.001; # P<0.05. FIG. 2C shows ROC curve analysis comparing performance of normalized urinary KIM-1 (dashed red line, AUC 0.98) and plasma KIM-1 (solid black line, AUC 0.96) levels. FIG. 2D shows a scatter plot demonstrating a positive correlation between plasma and urinary KIM-1 levels in all participants, including healthy volunteers (n=48) and patients with (n=28) or without AKI (n=16). (r=0.43; P<0.001). FIG. 2E shows a scatterplot demonstrating a correlation between plasma KIM-1 levels and urinary albumin-to-creatinine ratios (r=0.33; P=0.001). FIG. 2F shows a scatter plot demonstrating a correlation between urinary KIM-1 levels and urinary albumin levels (r=0.35; P<0.001 for urinary KIM-1). FIG. 2G shows a scatter plot demonstrating positive correlation between plasma KIM-1 and plasma creatinine in patients with or without AKI (r=0.58; P<0.001). FIG. 2H shows the plasma KIM-1 levels, and FIG. 2I shows urine KIM-1 levels collected at various times before and after CPB from nine patients who developed stage 1 AKI and nine who did not develop AKI. Mean plasma creatinine, plasma KIM-1 (FIG. 2H), normalized urinary KIM-1 (FIG. 2I), and urinary albumin (FIG. 2J) concentrations were determined. # P<0.05 for difference from baseline; *P<0.05 for difference between AKI and non-AKI groups. n=9 for both AKI and no-AKI groups. Error bars represents SDs.

FIG. 3A shows that, in a cross-sectional comparison, plasma KIM-1 levels were negatively associated with eGFR in patients with CKD of various causes. FIG. 3B shows that plasma KIM-1 levels are positively associated with increasing stages of CKD. FIG. 3C shows that in a cross-sectional comparison of 124 patients with type 1 diabetes and proteinuria, serum KIM-1 was positively associated with CKD stage. Median and 25th and 75th percentiles are shown. Numbers of patients in each category are indicated. FIG. 3D shows serum KIM-1 at baseline was associated with rate of renal decline (eGFR slopes) during 5-15 years (median, 10 years) of follow-up (Spearman correlation coefficient=0.52; P<0.001). The effect of serum KIM-1 remained very strong and significant (P<0.001) in multiple regression analyses when other covariates, such as baseline eGFR, urinary albumin-to-creatinine ratio, and hemoglobin A1c levels were considered. FIG. 3E shows serum KIM-1 level at baseline was a strong predictor of risk of progression to ESRD. Kaplan-Meier survival analysis shows the proportion of patients remaining without ESRD after 15 years of follow-up in patients with baseline serum KIM-1 below and above the median (97 pg/ml) (P<0.01). The effect of baseline serum KIM-1 remained significant in multivariable Cox regression analysis (P<0.01) when other covariates, such as baseline eGFR, urinary albumin-to-creatinine ratio, and hemoglobin A1c levels were considered. Analyses shown in FIGS. 3D and 3E were performed in 107 patients with type 1 diabetes, proteinuria, and CKD stages 1-3 at baseline. More clinical information of these patients is provided in Table 6 and can be found in Rosolowsky et al.[15] FIG. 3F shows a Western blot depicting 90-kD band of urinary KIM-1 in a patient with AKI (lane 2) and plasma KIM-1 in patients with AKI (lanes 4 and 5), and CKD (lane 6). Urine (lane 1) and plasma (lane 3) from healthy volunteers were also included for comparison.

FIG. 4A shows a dot plot indicates non-normalized urinary KIM-1 for each subject. *p<0.001. FIG. 4B shows a ROC curve analysis comparing performance of non-normalized urinary KIM-1 (AUC-0.91; 95% CI: 0.85-0.97, p<0.0001) in patients with and without AKI (HV & CS-ICU non-AKI). FIG. 4C shows a scatter plot of non-normalized urinary KIM-1 levels vs. plasma KIM-1 levels in all subjects including healthy volunteers and cardiac surgery ICU patients with or without AKI. (r=0.23, p=0.025).

FIG. 5A shows plasma KIM-1 is elevated in clear cell papillary subtype. FIG. 5B shows a AUC-ROC curve of plasma KIM-1 is elevated in clear cell papillary subtype. FIG. 5C shows plasma KIM-1 specific to tumor histology. FIG. 5D shows plasma KIM-1 levels in RCC subjects (identified by +) decrease post nephrectomy (PostNx) as compared to before nephrectomy (preNx).

FIG. 6A shows plasma KIM-1 is associated with TNM Staging of RCC, showing increased plasma KIM-1 levels as the severity of the RCC progresses. The TNM staging system is based on the size and/or extent (reach) of the primary tumor (T), the amount of spread to nearby lymph nodes (N), and the presence of metastasis (M) or secondary tumors formed by the spread of cancer cells to other parts of the body. T-stage refers to the extent of the Primary Tumor (T); TX: Primary tumor cannot be evaluated, T0: No evidence of primary tumor, Tis: Carcinoma in situ (CIS; abnormal cells are present but have not spread to neighboring tissue; although not cancer, CIS may become cancer and is sometimes called preinvasive cancer), T1, T2, T3, T4: Size and/or extent of the primary tumor. N-stage refers to the regional Lymph Nodes (N); N0: No regional lymph node involvement, N1, N2, N3 refer to the degree of regional lymph node involvement (number and location of lymph nodes). M-stage refers to the distant Metastasis (M), where MO indicates no distant metastasis detected, M1 indicates distant metastasis is present. FIG. 6B shows plasma KIM-1 is associated with tumor grade, showing that plasma KIM-1 is highest in subjects with grade 4 (G4) RCC as compared to subjects with RCC at grade 1 (G1). FIG. 6C shows plasma KIM-1 levels (pKIM-1) is associated with tumor size, with larger tumors having higher pKIM-levels. FIG. 6D shows no association between pKIM-1 and Age, and FIG. 6E shows no association of plasma KIM-1 levels and gender.

FIG. 7A shows Kaplan-Meier survival curves demonstrating that high plasma KIM-1 levels are associated with more severe disease progression in subjects with RCC.

FIG. 9A shows Kaplan-Meier survival curves demonstrating that high plasma KIM-1 levels are associated with more severe disease progression in subjects with RCC. FIG. 9B subjects with grade 3-4 (G3/4) or grade 1-2 (G1/2) RCC with higher plasma KIM-1 levels have a more severe progression as compared to subjects with the same grade of RCC but with lower plasma KIM-1 levels. FIG. 9C shows that subjects with metastatic RCC with higher plasma KIM-1 levels have a more severe disease progression as compared to subjects with the metastatic RCC but with lower plasma KIM-1 levels. FIG. 9D subjects with T stage 1-2 or grade 3-4 RCC with higher plasma KIM-1 levels have a more severe progression as compared to subjects with the same T-stage of RCC but with lower plasma KIM-1 levels.

FIG. 10A shows a Kaplien-meir survival curves showing high KIM-1 levels are associated with a decrease in overall survival compared to subjects with RCC with lower plasma KIM-1 levels. FIG. 10B subjects with grade 3 (G3) or grade 1-2 (G1/2) RCC with higher plasma KIM-1 levels have a lower survival rate and decreased overall survival as compared to subjects with the same grade of RCC but with lower plasma KIM-1 levels. FIG. 10C shows that subjects with metastatic RCC (M1), or non-metastasis (MO) RCC with higher plasma KIM-1 levels have a lower survival rate and decreased overall survival as compared to subjects with non-metastatic (MO) RCC but with lower plasma KIM-1 levels. FIG. 10D subjects with T stage 1-2 (T1/2) or T-stage 3 (T3) RCC with higher plasma KIM-1 levels have a lower survival rate and decreased overall survival as compared to subjects with the same T-stage of RCC but with lower plasma KIM-1 levels.

FIG. 11A shows Plasma KIM-1 is elevated in clear cell papillary subtype of RCC (ccRCC) in the German cohort subjects. FIG. 11B-11D shows plasma KIM-1 levels is associated with TNM staging of RCC showing increased plasma KIM-1 levels as the severity of the RCC progresses; FIG. 11B shows elevated pKIM in T3

RCC, FIG. 11C shows elevated pKIM-1 in subjects with N2 RCC, and FIG. 11D shows pKIM-1 is elevated in subjects with metastatic (M1) RCC. FIG. 11E shows a dot plot showing plasma KIM-1 (pKIM-1) is associated with tumor size. FIG. 11F shows there is no association of plasma KIM-1 with sex or gender.

DETAILED DESCRIPTION OF THE INVENTION

Figure 1A:
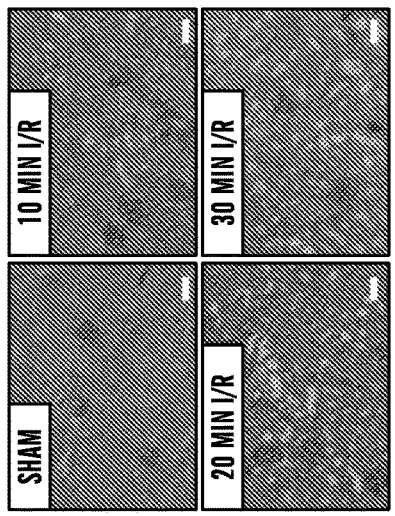
FIGS. 1A-1L show an increase in plasma KIM-1 levels in experimental models of kidney injury in mice and rats.

It should be understood that this invention is not limited to the particular methodology, protocols, and reagents, etc., described herein and as such may vary. The terminology used herein is for the purpose of describing particular embodiments only, and is not intended to limit the scope of the present invention, which is defined solely by the claims.

Acute kidney injury (AKI) is associated with high morbidity and mortality. The lack of sensitive and specific injury biomarkers has greatly impeded the development of therapeutic strategies to improve outcomes of AKI. The diagnostic approach to AKI has stagnated and rests today upon the same "legacy" biomarkers—BUN, creatinine, and urine output—that do not directly reflect cell injury but rather delayed functional consequences of the injury. This has greatly impeded therapeutic innovation.

The ectodomain of KIM-1 has been previously reported to be shed into the urine in both rodents (Ichimura et al., 273 J. Biol. Chem. 4135-42 (1998); Vaidya et al., 2 Expert Opin. Drug Metab. Toxicol. 697-713 (2006)), and humans (Han et al., 62 Kidney Int'1237-44 (2002)), after proximal tubular kidney injury. Previously, the inventors demonstrated that KIM-1 can be a urine biomarker for AKI. However, due to the significant variability of urinary excretion over time in patients with AKI, the use of KIM-1 as a reliable and accurate urine biomarker for AKI is limited because urine KIM-1 levels need to be measured in combination with renal excretion rate (by timing and measuring a subject urinary excretions), which is both time consuming and impractical in many instances where rapid diagnosis of AKI is required. Therefore, KIM-1 levels in the urine cannot reliably determine if the subject has AKI, as KIM-1 levels in random or spot urine samples can be inaccurate. Thus, the use of KIM-1 as a urine biomarker is limited due to accuracy, reliability and practical considerations.

Herein, the inventors have now surprisingly discovered that, in addition to the ectodomain of KIM-1 being shed into the lumen of the kidney tubules, since it is located primarily on the apical membrane of the epithelial cells, KIM-1 is released into the systemic circulation after kidney proximal tubule injury. Accordingly, the inventors have discovered that KIM-1 polypeptide is an accurate and sensitive plasma biomarker representing an integrated measure of kidney injury over time. Further, it has been reported that a single biomarker is rarely adequate to clearly define a particular pathologic state (Fliser et al., 18 J. Am. Soc. Nephrol. 1057-71 (2007); Rifai et al., 24 Nat. Biotech. 971-83 (2006)), with experts suggesting that combination of multiple biomarkers (e.g., a biomarkers panel) was an optimal to detect AKI more efficiently and accurately [Sprenkle P, Russo P (2013) Molecular markers for ischemia, do we have something better then creatinine and glomerular filtration rate? Arch Esp Urol 66: 99-114; Parikh C R, et al. (2013) Performance of Kidney Injury Molecule-1 and Liver Fatty Acid-Binding Protein and Combined Biomarkers of AKI after Cardiac Surgery. Clin J Am Soc Nephrol 8: 1079-1088); Liang X L, et al. (2010) Combination of urinary kidney injury molecule-1 and interleukin-18 as early biomarker for the diagnosis and progressive assessment of acute kidney injury following cardiopulmonary bypass surgery: a prospective nested case-control study).

Given the previous reports that urinary KIM-1 biomarker by itself is an inadequate to diagnose AKI, it is surprising that levels of KIM-1 polypeptide in the blood is an accurate and sensitive plasma biomarker of AKI. The fact that blood levels of KIM-1 polypeptide by itself (and not with other blood biomarkers) can be used to reliably and accurately detect a subject with AKI is highly advantageous as it enables simple, quick and non-complex (e.g., not multiplex) assays to be used for the rapid and accurate diagnosis of a subject with AKI.

Accordingly, the present invention is based on the discovery that blood levels of KIM-1 polypeptide can accurately and reliably detect AKI and CKD in subjects, and subjects, (e.g., type I diabetic subjects) at risk of end stage renal disease (ESRD). Importantly, unlike measuring KIM-1 protein in the urine, blood KIM-1 protein levels can be measured in random blood samples and does not require determination of the renal excretion rate of the subject. Accordingly, the invention is directed to methods for diagnosis of AKI by determining and monitoring the levels of KIM-1 in a blood sample from the subject, e.g., where the blood sample can be any of; whole blood, plasma, serum or a fractionated blood sample.

Sensitive assays to measure plasma KIM-1 in mouse, rat and human were developed and validated in the current study. Plasma KIM-1 levels were elevated in a graded fashion with increasing periods of ischemia (10, 20 or 30 min) as early as 6 hr after reperfusion in mice and with gentamicin treatment (50 or 200 mg/kg for 10 days) in rats. In humans, plasma KIM-1 levels were higher in patients with acute kidney injury (AKI) than healthy controls or patients admitted to the ICU without AKI with an area under the curve of receiver operating characteristic curve (AUC-ROC) of 0.96. The inventors discovered that in patients undergoing cardiopulmonary bypass, plasma KIM-1 levels increased within 2 days after surgery only in patients who developed AKI (P=0.008), and that blood KIM-1 levels were also elevated in patients with chronic kidney disease (CKD) of various etiologies, and correlated with stage of CKD. The inventors have also discovered that in a cohort of patients with type 1 diabetes and proteinuria, serum KIM-1 level at baseline strongly predicted rate of eGFR loss and risk of end stage renal disease (ESRD) during 5-15 years of follow-up, after adjustment for baseline urinary albumin-to-creatinine ratio, eGFR, and Hb1Ac. These results showing plasma KIM-1 concentration elevated in both acute and chronic kidney disease demonstrate the inventors discovery that KIM-1 polypeptide can be a blood (e.g, plasma) biomarker with high specificity for kidney injury in mice, rats and humans, and can be used in the diagnosis and prognosis of AKI.

Herein, the inventors have also discovered that KIM-1 in the blood is increased in subjects with ccRCC and papillary RCC, and that increased levels of KIM-1 in the blood of subjects indicates a more severe tumor pathology and/or RCC metastasis. Although KIM-1 levels are increased in the urine in patients with ccRCC (Bonventre (2009), Nephrol Dial Transplant, 24; 3265-3268; Han W K et al., (2005) Human kidney injury molecule-1 is a tissue and urinary tumor marker of renal cell carcinoma. J Am Soc Nephrol;

16: 1126-1134). Circulating KIM-1 is more reliable for general use in detecting metastases and over all burden of tumor mass since the KIM-1 ectodomain may not get adequately filtered by the glomeruli of the kidney due to the size of the polypeptide. Furthermore when the tumor is located in the kidney the architecture of the kidney is distorted and hence KIM-1 may not readily get into the collecting system of the kidney and excreted into the urine. As described herein, it is highly surprising that it is released into the blood, as KIM-1 polypeptide is expressed by tubular epithelium kidney cells and it was previously believed that it was released only into the urine in subjects with RCC.

Accordingly, another aspect of the present invention is directed to methods, kits and compositions for diagnosis of Renal Cell carcinoma (RCC), e.g., ccRCC in a subject by detecting levels of KIM-1 in the blood sample obtained from a subject. Accordingly, aspects of the present invention provides compositions and methods for the diagnosis and prognosis of renal cell carcinoma (RCC) using blood or plasma levels of KIM-1 as a diagnostic test that is sensitive and specific. Plasma KIM-1 levels is useful for diagnosis and/or assessment of prognosis of clear cell RCC in a subject.

Current methods to detect RCC in a subject involve analysis of a biopsy sample, and often result in inaccurate diagnosis of grade of the RCC. The present invention allows for a non-invasive method for diagnosis of RCC in a subject. In particular, in some embodiments, the present invention relates to measuring KIM-1 in the blood of a subject to predict aggressiveness or stage of RCC. In some embodiments, the present invention relates to measuring KIM-1 in the blood of a subject to predict the severity of the RCC and the outcome of survival of a subject with RCC. Importantly, by the time a subject has a symptom of RCC, 50% of the subjects have metastatic RCC. The present invention can be used to detect RCC in a subject when the subject is asymptomatic, as an increase in KIM-1 protein levels in the subject of at least 4-fold above a reference level can be used for very early detection of RCC before the subject has a symptom of RCC.

In alternative embodiments, measuring KIM-1 in the blood of a subject before, and after, and optionally during a treatment for RCC can be used to monitor treatment progression, and the treatment can be adjusted accordingly. As an exemplary example only, a subject identified to have an aggressive RCC (e.g., has a plama KIM-1 level indicating the subject has a grade 3-4 RCC), the subject can be administered an aggressive RCC treatment, and where plasma KIM-1 levels after a period of treatment with the aggressive therapy have not decreased (e.g., stayed the same or increased), a clinican can adjust the dose or switch treatment for the subject, and in alterative embodiments, where plasma KIM-1 levels have decreased after a period of time with the RCC treatment, the subject can continue the treatment or be switched to a maintenance dose. Accordingly, the present invention encompasses methods to monitor effectiveness of a therapeutic treatment for RCC, which is useful for clinical trials. For example, KIM-1 protein in the blood, e.g., plasma is useful in the testing of potential therapeutic strategies for RCC and could serve as surrogate endpoints in clinical trials and help shortening the length of a trial and increasing the accuracy of such clinical trials.

Another aspect of the present invention provides a method for monitoring the progression of renal cell carcinoma (RCC) in a subject having, or a subject likely to develop renal cell carcinoma (RCC), the method comprising: (a) measuring the level of KIM-1 polypeptide in a blood sample obtained from the subject, e.g., a plasma sample or serum sample at a first time point; (b) measuring the level of the level of KIM-1 polypeptide in a blood sample obtained from the subject at a second time point; and comparing the level of KIM-1 polypeptide from the first time point with the level of KIM-1 polypeptide from the second timepoint; wherein a change in the level of the KIM-1 polypeptide at the first time point as compared to the level of KIM-1 polypeptide second timepoint indicates an alteration in the rate of progression of RCC in the subject. In such embodiments, if a decrease in the level of KIM-1 polypeptidefrom the first timepoint as compared to the second timepoint, it indicates in improved prognosis of RCC progression at the second timepoint as compared to the first timepoint. Alternatively, if an increase in the level of the of KIM-1 polypeptide from the first timepoint as compared to the second timepoint indicates in decreased prognosis of RCC progression at the second timepoint as compared to the first timepoint.

Microbead technology or other immunoassays (e.g., dipstick and/or paper-based assays) can be used to measure KIM-1 alone, or in combination with other blood biomarkers or other AKI biomarkers in the blood. Microbead technology can be used to measure KIM-1 polypeptide alone, or with other blood biomarkers, in the same aliquot of blood sample at the same time. An assay that is capable of being tailored or modified to enable detection of other blood biomarkers, and/or total blood protein (e.g., a normalizing protein) in the same aliquot of blood sample at the same time is extremely useful.

Definitions

As used herein, "kidney injury" includes any injury to the proximal tubule of the kidney and includes, but is not limited to, acute kidney injury (AKI), chronic kidney disease (CKD) and kidney fibrosis.

As used herein, "acute kidney injury", also known as "AKI" or "acute renal failure (ARF)" or "acute kidney failure", refers to a disease or condition where a rapid loss of renal function occurs due to damage to the kidneys, resulting in retention of nitrogenous (urea and creatinine) and non-nitrogenous waste products that are normally excreted by the kidney. Depending on the severity and duration of the renal dysfunction, this accumulation is accompanied by metabolic disturbances, such as metabolic acidosis (acidification of the blood) and hyperkalaemia (elevated potassium levels), changes in body fluid balance, and effects on many other organ systems. It can be characterized by oliguria or anuria (decrease or cessation of urine production), although nonoliguric ARF may occur. Acute kidney injury may be a consequence of various causes including a) pre-renal (causes in the blood supply), which includes, but is not limited to, hypovolemia or decreased blood volume, usually from shock or dehydration and fluid loss or excessive diuretics use; hepatorenal syndrome, in which renal perfusion is compromised in liver failure; vascular problems, such as atheroembolic disease and renal vein thrombosis, which can occur as a complication of nephrotic syndrome; infection, usually sepsis, and systemic inflammation due to infection; severe burns; sequestration due to pericarditis and pancreatitis; and hypotension due to antihypertensives and vasodilators; b) intrinsic renal damage, which includes, but is not limited to, toxins or medication (e.g. some NSAIDs, aminoglycoside antibiotics, iodinated contrast, lithium, phosphate nephropathy due to bowel preparation for colonoscopy with sodium phosphates); rhabdomyolysis or breakdown of muscle tissue, where the resultant release of myoglobin in the blood affects the kidney, which can also be caused by injury (especially crush injury and extensive blunt trauma), statins, stimulants and some other drugs; hemolysis or breakdown of red blood cells, which can be caused by various conditions such as sickle-cell disease, and lupus erythematosus; multiple myeloma, either due to hypercalcemia or "cast nephropathy"; acute glomerulonephritis which may be due to a variety of causes, such as anti glomerular basement membrane disease/Goodpasture's syndrome, Wegener's granulomatosis or acute lupus nephritis with systemic lupus erythematosus; and c) post-renal causes (obstructive causes in the urinary tract) which include, but are not limited to, medication interfering with normal bladder emptying (e.g. anticholinergics); benign prostatic hypertrophy or prostate cancer; kidney stones; abdominal malignancy (e.g. ovarian cancer, colorectal cancer); obstructed urinary catheter; or drugs that can cause crystalluria and drugs that can lead to myoglobinuria & cystitis.

As used herein, the term "kidney fibrosis" also known as "renal fibrosis" refers to any condition having kidney fibrosis as a symptom or cause of the condition, or a condition that can be worsened by the development of kidney fibrosis, or a condition the progression of which is linked to the progression of kidney fibrosis. Kidney fibrosis is the formation of excess fibrous connective tissue in kidney characterized by glomerulosclerosis and tubulointerstitial fibrosis. The pathogenesis of kidney fibrosis is a monotonous process that is characterized by an excessive accumulation and deposition of extracellular matrix (ECM) components (see e.g., Y. Liu, Kidney International 2006, 69, 213-217). Kidney fibrosis can be evaluated by methods including, but not limited to, histology, immunohistochemistry, Western blot, and real-time PCR for mRNA and protein expression of extracellular matrix including collagen I and alpha-smooth muscle actin, and activation of TGF beta/Smad signaling. Kidney fibrosis can result from various diseases and insults to the kidneys. Examples of such diseases and insults include chronic kidney disease, metabolic syndrome, vesicoureteral reflux, tubulointerstitial renal fibrosis, diabetes (including diabetic nephropathy), and resultant glomerular nephritis (GN), including, but not limited to, focal segmental glomerulosclerosis and membranous glomerulonephritis, mesangiocapillary GN. Since kidney fibrosis is associated with loss of blood vessels, this results in secondary ischemia which can also result in glomerulare disease with loss of glomerular function. Regardless of the primary cause, insults to the kidneys may result in kidney fibrosis and the concomitant loss of kidney function. (Schena, F. and Gesualdo, L., Pathogenic Mechanisms of Diabetic Nephropathy, J. Am. Soc. Nephrol., 16: S30-33 (2005); Whaley-Connell, A., and Sower, J R., Chronic Kidney Disease and the Cardiometabolic Syndrome, J. Clin. Hypert., 8(8): 546-48 (2006)). Conditions associated with kidney fibrosis include, but are not limited to, diabetic nephropathy, chronic kidney disease, end-stage renal disease, systemic lupus erythematosis, vasculitis, IgA nephropathy, other autoimmune diseases, paraprotein diseases, diabetes. In some embodiments, a condition associated with kidney fibrosis results from persistent KIM-1 expression in kidney cells. Renal Fibrosis has three stages which are inflammation reaction stage, formation of fibrosis stage and cicatricial stage respectively. Symptoms vary depending on the stage. There are no obvious symptoms in the inflammation reaction stage. In the formation stage, symptoms occur such as frequent night urine, high potassium, high blood pressure and itchy skin and so on. In the cicatricial stage, renal failure may occur.

As used herein, a "subject" refers to a mammal, preferably a human. The term "individual", "subject", and "patient" are used interchangeably herein, and refer to an animal, for example a mammal, such as a human. The term "mammal" is intended to encompass a singular "mammal" and plural "mammals," and includes, but is not limited to: humans, non-human primates such as apes, monkeys, orangutans, and chimpanzees; canids such as dogs and wolves; felids such as cats, lions, and tigers; equids such as horses, donkeys, and zebras; food animals such as cows, pigs, and sheep; ungulates such as deer and giraffes; rodents such as mice, rats, hamsters and guinea pigs; and bears.

A "subject in need" of treatment for a particular condition can be a subject having that condition, diagnosed as having that condition, or at risk of developing that condition.

As used herein, the terms "sample", "biological sample" or "blood sample" refers to a sample of blood obtained from the subject. Blood samples include, but are not limited to, whole blood, serum or plasma. In some embodiments, the whole blood sample is further processed into serum or plasma samples. The term also includes a mixture of the above-mentioned samples. The term "sample" also includes untreated or pretreated (or pre-processed) blood samples. In some embodiments, a sample can comprise one or more cells from the subject. In some embodiments, a sample is taken from a human subject, and in alternative embodiments the sample is taken from any mammal, such as rodents, animal models of diseases, commercial animals, companion animals, dogs, cats, sheep, cattle, and pigs, etc. The sample can be pretreated as necessary for storage or preservation, by dilution in an appropriate buffer solution or concentrated, if desired. Any of a number of standard aqueous buffer solutions, employing one of a variety of buffers, such as phosphate, Tris, or the like, at physiological pH can be used. The sample can in certain circumstances be stored for use prior to use in the assays as disclosed herein. Such storage can be at +4° C. or frozen, for example at −20° C. or −80° C.

As used herein, the term "biomarker" or "urinary biomarker" refers to a polypeptide expressed endogenously in an individual or found or sequestered in a blood sample from an individual. The term "acute kidney injury biomarker" is used throughout the specification as an example of a type of biomarker useful with the methods described herein. Acute kidney injury and pyelonephritis are examples of conditions associated with a biomarker as the term "biomarker" is used herein. A blood biomarker or acute kidney injury biomarker can include kidney injury molecule-1 (KIM-1) polypeptide or a fragment thereof, e.g., the ectodomain of KIM-1 polypeptide or a fragment thereof. KIM-1 polypeptide as a biomarker useful for diagnosing AKI also encompasses domains or fragments of KIM-1 polypeptide, as well as species, variants, homologues, allelic forms, mutant forms, and equivalents of KIM-1 polypeptide. In some embodiments, the KIM-1 polypeptide is human KIM-1 polypeptide.

As used herein the term "agent" refers to a protein-binding agent that specifically binds to a target protein and permits detection and/or quantification of levels, concentrations, expression levels, or activity of the total protein in a blood sample, a normalizing protein (e.g., actin), or KIM-1 polypeptide (including the ectodomain of KIM-1 polypeptide) in a blood sample. Such protein-binding agents include, but are not limited to, small molecules, antibodies, antibody fragments (e.g., antigen-binding fragments of antibodies), recombinant antibodies, chimeric antibodies, tribodies, midibodies, protein-binding agents, small molecules, recombinant protein, peptides, aptamers, avimers and protein-binding derivatives or fragments thereof. As used herein, the phrase "agent specific for KIM-1 polypeptide" refers to a protein-binding agent that permits detection and/or quantification of levels, concentrations, or expression levels for the KIM-1 polypeptide (including the ectodomain of KIM-1 polypeptide). Such agents include, but are not limited to, antibodies, recombinant antibodies, chimeric antibodies, tribodies, midibodies, protein-binding agents, small molecules, recombinant protein, peptides, aptamers, avimers and protein-binding derivatives or fragments thereof. As defined herein, an agent upon binding to a KIM-1 polypeptide, normalizing protein, or total protein forms an "agent-biomarker complex," (e.g., agent-KIM-1 complex), "agent-normalizing protein complex," or "agent-total protein complex." As used herein, the term "reporter molecule information" refers to data derived from a signal indicating binding of an agent to or complex formation with the KIM-1 polypeptide biomarker in the blood sample, i.e., formation of an agent-KIM-1 complex," "agent-normalizing protein complex," or "agent-total protein complex." A signal can comprise e.g., light, fluorescence, colorimetric or other detectable signal that indicates agent binding to an acute kidney injury biomarker, a normalizing protein, or total protein.

The terms "protein-binding molecule" refers to a agent or protein which specifically binds to an protein, such as an a protein-binding molecule which specifically binds a RCC biomarker protein, e.g., to KIM-1 polypeptide. Protein-binding molecules are well known in the art, and include antibodies, protein-binding peptide and the like. The region on the protein which binds to the protein-binding molecule is referred to as the epitope, and the protein which is bound to the protein-binding molecule is often referred to in the art as an antigen.

As used herein, the term "antibody" refers to immunoglobulin molecules and immunologically active portions of immunoglobulin molecules, i.e., molecules that contain an antigen binding site that specifically bind an antigen. The terms also refers to antibodies comprised of two immunoglobulin heavy chains and two immunoglobulin light chains as well as a variety of forms besides antibodies; including, for example, Fv, Fab, and F(ab)'2 as well as bifunctional hybrid antibodies (e.g., Lanzavecchia et al., Eur. J. Immunol 17, 105 (1987)) and single chains (e.g., Huston et al., Proc. Natl. Acad. Sci. U.S.A., 85, 5879-5883 (1988) and Bird et al., Science 242, 423-426 (1988), which are incorporated herein by reference). (See, generally, Hood et al., Immunology, Benjamin, N.Y., 2ND ed. (1984), Harlow and Lane, Antibodies. A Laboratory Manual, Cold Spring Harbor Laboratory (1988) and Hunkapiller and Hood, Nature, 323, 15-16 (1986), which are incorporated herein by reference). In some embodiments, antibody reagents, e.g. antibodies, monoclonal and chimeric antibodies useful in the methods as disclosed herein can be manufactured using well-known methods, e. g., as described in Howard and Kaser "Marking and Using Antibodies: A Practical Handbook" CRC Press (2006); which is incorporated by reference herein in its entirety. Antibody fragments or antigen-binding antibody fragments includes any protein or peptide containing molecule that comprises at least a portion of an immunoglobulin molecule, and include, but are not limited to a complementarily determining region (CDR) of a heavy or light chain or a ligand binding portion thereof, a heavy chain or light chain variable region, a heavy chain or light chain constant region, a framework (FR) region, or any portion thereof, or at least one portion of a binding protein, any of which can be incorporated into an antibody of the present invention. The antibodies can be polyclonal or monoclonal and can be isolated from any suitable biological source, e.g., murine, rat, sheep and canine. Additional sources are identified infra.

The term "antibody" is further intended to encompass digestion fragments, specified portions, derivatives and variants thereof, including antibody mimetics or comprising portions of antibodies that mimic the; structure and/or function of an antibody or specified fragment or portion thereof, including single chain antibodies and fragments thereof. Examples of binding fragments encompassed within the term "antigen binding portion" of an antibody include a Fab fragment, a monovalent fragment consisting of the VL, VH, CL and CH, domains; a F(ab') 2 fragment, a bivalent fragment comprising two Fab fragments linked by a disulfide bridge at the hinge region; a Ed fragment consisting of the VH and CH, domains; a Fv fragment consisting of the VL and VH domains of a single arm of an antibody, a dAb fragment (Ward et al. (1989) Nature 341:544-546), which consists of a VH domain; and an isolated complementarily determining region (CDR). Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules (known as single chain Fv (scFv)). Bird et al. (1988) Science 242:423-426 and Huston et al. (1988) Proc. Natl. Acad. Sci. USA 85:5879-5883. Single chain antibodies are also intended to be encompassed within the term "fragment of an antibody." Any of the above-noted antibody fragments are obtained using conventional techniques known to those of skill in the art, and the fragments are screened for binding specificity and neutralization activity in the same manner as are intact antibodies.

The terms "antigen-binding fragment" or "antigen-binding domain", which are used interchangeably herein to refer to one or more fragments of a full length antibody that retain the ability to specifically bind to a target of interest. Examples of binding fragments encompassed within the term "antigen-binding fragment" of a full length antibody include (i) a Fab fragment, a monovalent fragment consisting of the VL, VH, CL and CH1 domains; (ii) a F(ab')2 fragment, a bivalent fragment including two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment (Ward et al., (1989) Nature 341:544-546; which is incorporated by reference herein in its entirety), which consists of a VH or VL domain; and (vi) an isolated complementarity determining region (CDR) that retains specific antigen-binding functionality. Furthermore, although the two domains of the Fv fragment, VL and VH, are coded for by separate genes, they can be joined, using recombinant methods, by a synthetic linker that enables them to be made as a single protein chain in which the VL and VH regions pair to form monovalent molecules known as single chain Fv (scFv). See e.g., U.S. Pat. Nos. 5,260,203, 4,946,778, and 4,881,175; Bird et al. (1988) Science 242:423-426; and Huston et al. (1988) Proc. Natl. Acad. Sci. USA 85:5879-5883. Antibody fragments can be obtained using any appropriate technique including conventional techniques known to those of skill in the art. The term "monospecific antibody" refers to an antibody that displays a single binding specificity and affinity for a particular target, e.g., epitope. This term includes a "monoclonal antibody" or "monoclonal antibody composition," which as used herein refer to a preparation of antibodies or fragments thereof of single molecular composition, irrespective of how the antibody was generated.

The term "epitope" means a protein determinant capable of specific binding to an antibody. Epitopes usually consist of chemically active surface groupings of molecules such as amino acids or sugar side chains and usually have specific three dimensional structural characteristics, as well as specific charge characteristics. Conformational and non-conformational epitopes are distinguished in that the binding to the former but not the latter is lost in the presence of denaturing solvents. The phrase can also refer to continuous or discontinuous epitopes in which the primary sequence (i.e., the amino acid sequence) is not similar but nonetheless the epitopes are still recognized by the same antibody.

The term "antibody variant" is intended to include antibodies produced in a species other than a mouse. It also includes antibodies containing post translational modifications to the linear polypeptide sequence of the antibody or fragment. It further encompasses fully human antibodies. The term "antibody derivative" is intended to encompass molecules that bind an epitope as defined above and which are modifications or derivatives of a native monoclonal antibody of this invention. Derivatives include, but are not limited to, for example, bispecific, multispecific, heterospecific, trispecific, tetraspecific, multispecific antibodies, diabodies, chimeric, recombinant and humanized.

The term "human antibody" as used herein, is intended to include antibodies having variable and constant regions derived from human germline immunoglobulin sequences. The human antibodies of the present invention can include amino acid residues not encoded by human germline immunoglobulin sequences (e.g., mutations introduced by random or site-specific mutagenesis in vitro or by somatic mutation in viva). However, the term "human antibody" as used herein, is not intended to include antibodies in which CDR sequences derived from the germline of another mammalian species, such as a mouse, have been grafted onto human framework sequences. Thus, as used herein, the term "human antibody" refers to an antibody in which substantially every part of the protein (e.g., CDR, framework, CL, CH domains (e.g., CH1, CH2, CH3), hinge, (Via, VH)) is substantially non-immunogenic in humans, with only minor sequence changes or variations. Similarly, antibodies designated primate (monkey, baboon, chimpanzee, etc.), rodent (mouse, rat, rabbit, guinea pig, hamster, and the like) and other mammals designate such species, sub-genus, genus, sub-family, family specific antibodies. Further, chimeric antibodies include any combination of the above. Such changes or variations optionally and preferably retain or reduce the immunogenicity in humans or other species relative to non-modified antibodies. Thus, a human antibody is distinct from a chimeric or humanized antibody. It is pointed out that a human antibody can be produced by a non-human animal or prokaryotic or eukaryotic cell that is capable of expressing functionally rearranged human immunoglobulin (e.g., heavy chain and/or light chain); genes. Further, when a human antibody is a single chain antibody, it can comprise a linker peptide that is not found in native human antibodies. For example, an Fv can comprise a linker peptide, such as two to about eight glycine or other amino acid residues, which connects the variable region of the heavy chain and the variable region of the light chain. Such linker peptides are considered to be of human origin.

As used herein, a human antibody is "derived from" a particular germline sequence if the antibody is obtained from a system using human immunoglobulin sequences, e.g., by immunizing a transgenic mouse carrying human immunoglobulin genes or by screening a human immunoglobulin gene library. A human antibody that is "derived from" a human germline immunoglobulin sequence can be identified as such by comparing the amino acid sequence of the human antibody to the amino acid sequence of human germline immunoglobulins. A selected human antibody typically is at least 90% identical in amino acids sequence to an amino acid sequence encoded by a human germline immunoglobulin gene and contains amino acid residues that identify the human antibody as being human when compared to the germline immunoglobulin amino acid sequences of other species (e.g., murine germline sequences). In certain cases, a human antibody can be at least about 95%, or even at least about 96%, or least about 97%, or least about 98%, or least about 99% identical in amino acid sequence to the amino acid sequence encoded by the germline immunoglobulin gene. Typically, a human antibody derived from a particular human germline sequence will display no more than 10 amino acid differences from the amino acid sequence encoded by the human germline immunoglobulin gene. In certain cases, the human antibody can display no more than 5, or even no more than 4, 3, 2, or 1 amino acid difference from the amino acid sequence encoded by the germline immunoglobulin gene.

The terms "monoclonal antibody" or "monoclonal antibody composition" as used herein refer to a preparation of antibody molecules of single molecular composition. A monoclonal antibody composition displays a single binding specificity and affinity for a particular epitope.

The term "human monoclonal antibody" refers to antibodies displaying a single binding specificity which have variable and constant regions derived from human germline immunoglobulin sequences. The term "recombinant human antibody", as used herein, includes all human antibodies that are prepared, expressed, created or isolated by recombinant means, such as antibodies isolated from an animal (e.g., a mouse) that is transgenic or transchromosomal for human immunoglobulin genes or a hybridoma prepared therefrom, antibodies isolated from a host cell transformed to express the antibody, e.g., from a transfectoma, antibodies isolated from a recombinant, combinatorial human antibody library, and antibodies prepared, expressed, created or isolated by any other means that involve splicing of human immunoglobulin gene sequences to other DNA sequences. Such recombinant human antibodies have variable and constant regions derived from human germline immunoglobulin sequences. In certain embodiments, however, such recombinant human antibodies can be subjected to in vitro mutagenesis (or, when an animal transgenic for human Ig sequences is used, in viva somatic mutagenesis) and thus the amino acid sequences of the VH and VL regions of the recombinant antibodies are sequences that, while derived from and related to human germline VH and VL sequences, can not naturally exist within the human antibody germline repertoire in vivo. As used herein, "isotype" refers to the antibody class (e.g., IgM or IgG1) that is encoded by heavy chain constant region genes.

An "antigen-binding site" or "binding portion" refers to the part of an immunoglobulin molecule that participates in antigen binding. The antigen-binding site is formed by amino acid residues of the N-terminal variable ("V") regions of the heavy ("H") and light ("L") chains. Three highly divergent stretches within the V regions of the heavy and light chains are referred to as "hypervariable regions" which are interposed between more conserved flanking stretches known as "framework regions" or "FRs". Thus, the term "FR" refers to amino acid sequences that are naturally found between and adjacent to hypervariable regions in immunoglobulins. In an antibody molecule, the three hypervariable regions of a light chain and the three hypervariable regions of a heavy chain are disposed relative to each other in three dimensional space to form an antigen binding "surface". This surface mediates recognition and binding of the target antigen. The three hypervariable regions of each of the heavy and light chains are referred to as "complementarity determining regions" or "CDRs" and are characterized, for example by Kabat et al. Sequences of proteins of immunological interest, 4th ed. U.S. Dept. Health and Human Services, Public Health Services, Bethesda, Md. (1987).

As used herein, the term "specific binding" refers to a chemical interaction between two molecules, compounds, cells and/or particles wherein the first entity (e.g., antibody or antigen-binding fragment) binds to the second, target entity (e.g., KIM-1 polypeptide, and/or the ectodomain of KIM-1 polypeptide) with greater specificity and affinity than it binds to a third entity which is a non-target. In some embodiments, specific binding can refer to an affinity of the first entity for the second target entity which is at least 10 times, at least 50 times, at least 100 times, at least 500 times, at least 1000 times or greater than the affinity for the third non-target entity. In particular, the terms "specifically binds," "specific binding affinity" (or simply "specific affinity"), and "specifically recognize," and other related terms when used to refer to binding between a protein and an antibody, refers to a binding reaction that is determinative of the presence of the protein in the presence of a heterogeneous population of proteins and other biologics. Thus, under designated conditions, a specified antibody binds preferentially to a particular protein (e.g., KIM-1) and does not bind in a significant amount to other proteins present in the sample. An antibody that specifically binds to a protein has an association constant of at least $10^3 M^{-1}$ or $10^4 M^{-1}$, sometimes $10^5 M^{-1}$ or $10^6 M^{-1}$, in other instances $10^6 M^{-1}$ or $10^{10} M^{-1}$, preferably $10^8 M^{-1}$ to $10^9 M^{-1}$, and more preferably, about $10^{10} M^{-1}$ to $10^{11} M^{-1}$ or higher. Protein-binding molecules with affinities greater than $10^8 M^{-1}$ are useful in the methods of the present invention. A variety of immunoassay formats can be used to select antibodies specifically immunoreactive with a particular protein. For example, solid-phase ELISA immunoassays are routinely used to select monoclonal antibodies specifically immunoreactive with a protein. See, e.g., Harlow and Lane (1988) Antibodies, A Laboratory Manual, Cold Spring Harbor Publications, New York, for a description of immunoassay formats and conditions that can be used to determine specific immunoreactivity.

An "array" broadly refers to an arrangement of agents (e.g., proteins, antibodies, replicable genetic packages) in positionally distinct locations on a substrate. In some instances the agents on the array are spatially encoded such that the identity of an agent can be determined from its location on the array. A "microarray" generally refers to an array in which detection requires the use of microscopic detection to detect complexes formed with agents on the substrate. A "location" on an array refers to a localized area on the array surface that includes agents, each defined so that it can be distinguished from adjacent locations (e.g., being positioned on the overall array, or having some detectable characteristic, that allows the location to be distinguished from other locations). Typically, each location includes a single type of agent but this is not required. The location can have any convenient shape (e.g., circular, rectangular, elliptical or wedge-shaped). The size or area of a location can vary significantly. In some instances, the area of a location is greater than 1 cm2, such as 2 cm2, including any area within this range. More typically, the area of the location is less than 1 cm2, in other instances less than 1 mm2, in still other instances less than 0.5 mm$^2$, in yet still other instances less than 10,000 mm$^2$, or less than 100 mm$^2$.

A "label" refers to an agent that can be detected by using physical, chemical, optical, electromagnetic and/or other methods. Examples of detectable labels that can be utilized include, but are not limited to, radioisotopes, fluorophores, chromophores, mass labels, electron dense particles, magnetic particles, spin labels, molecules that emit chemiluminescence, electrochemically active molecules, enzymes, cofactors, and enzyme substrates.

As used herein, the terms "proteins" and "polypeptides" are used interchangeably to designate a series of amino acid residues connected to each other by peptide bonds between the alpha-amino and carboxy groups of adjacent residues. The terms "protein", and "polypeptide" refer to a polymer of amino acids, including modified amino acids (e.g., phosphorylated, glycated, glycosylated, etc.) and amino acid analogs, regardless of its size or function. "Protein" and "polypeptide" are often used in reference to relatively large polypeptides, whereas the term "peptide" is often used in reference to small polypeptides, but usage of these terms in the art overlaps. The terms "protein" and "polypeptide" are used interchangeably herein when referring to a gene product and fragments thereof. Thus, exemplary polypeptides or proteins include gene products, naturally occurring proteins, homologs, orthologs, paralogs, fragments and other equivalents, variants, fragments, and analogs of the foregoing.

The terms "disease", "disorder", or "condition" are used interchangeably herein, refer to any alternation in state of the body or of some of the organs, interrupting or disturbing the performance of the functions and/or causing symptoms such as discomfort, dysfunction, distress, or even death to the person afflicted or those in contact with a person. A disease or disorder can also related to a distemper, ailing, ailment, malady, disorder, sickness, illness, complaint, affectation.

The term "cancer" or "malignancy" are used interchangeably herein, refers to diseases that are characterized by uncontrolled, abnormal growth of cells which results in an increase in a particular cell type or increase in a tissue growth or tissue mass. Cancer cells can spread locally or through the bloodstream and lymphatic system to other parts of the body. The term is also intended to include any disease of an organ or tissue in mammals characterized by poorly controlled or uncontrolled multiplication of normal or abnormal cells in that tissue and its effect on the body as a whole. Cancer diseases within the scope of the definition comprise benign neoplasms, dysplasias, hyperplasias as well as neoplasms showing metastatic growth or any other transformations like e.g. leukoplakias which often precede a breakout of cancer.

As used herein, the term "tumor" refers to a mass of transformed cells that are characterized, at least in part, by containing angiogenic vasculature. The transformed cells are characterized by neoplastic uncontrolled cell multiplication which is rapid and continues even after the stimuli that initiated the new growth has ceased. The term "tumor" is used broadly to include the tumor parenchymal cells as well as the supporting stroma, including the angiogenic blood vessels that infiltrate the tumor parenchymal cell mass. Although a tumor generally is a malignant tumor, i.e., a cancer having the ability to metastasize (i.e. a metastatic tumor), a tumor also can be nonmalignant (i.e. non-metastatic tumor). Tumors are hallmarks of cancer, a neoplastic disease the natural course of which is fatal. Cancer cells exhibit the properties of invasion and metastasis and are highly anaplastic.

As used herein, the term "metastases" or "metastatic tumor" refers to a secondary tumor that grows separately elsewhere in the body from the primary tumor and has arisen from detached, transported cells, wherein the primary tumor is a solid tumor. The primary tumor, as used herein, refers to a tumor that originated in the location or organ in which it is present and did not metastasize to that location from another location. As used herein, a "malignant tumor" is one having the properties of invasion and metastasis and showing a high degree of anaplasia. Anaplasia is the reversion of cells to an immature or a less differentiated form, and it occurs in most malignant tumors.

The term "renal cell carcinoma" and "RCC" are used interchangeably herein, refers to a tumor of the kidney. Tumors of the kidney can be malignant or benign and are the most common primary malignant kidney tumor. RCC usually begins in the cells that line the small tubes of each nephron. Renal cell tumors can grow as a single mass, and can multiple RCC tumors can develop on a single kidney or both kidneys. The term RCC encompasses different sub-types of RCC, such as, but not limited to epithelial renal cell carcinoma (RCC), clear cell (conventional), papillary RCC (chromophil), chromophobe RCC, collecting duct RCC (<1%) and unclassified RCC subtypes.

The term "clear cell RCC" also referred to as "ccRCC" refers to the most common renal neoplasm seen in adults (70% of tumors derived from tubular epithelium). Clear cell RCC can be as small as 1 cm or less and discovered incidentally, or it can be as bulky as several kilograms, and often presents pain, as a palpable mass or with hematuria, but a wide variety of paraneoplastic syndromes have been described. Clear cell RCC might be clinically silent for years and may present with symptoms of metastasis. Clear cell RCC has a characteristic gross appearance; the tumor is solid, lobulated, and yellow, with variegation due to necrosis and hemorrhage, with in some instances, the tumor circumscribed, or invade the perirenal fat or the renal vein.

As used herein, the terms "treat" "treatment," "treating," or "amelioration" refer to therapeutic treatments, wherein the object is to reverse, alleviate, ameliorate, inhibit, slow down or stop the progression or severity of a condition associated with kidney injury, e.g., AKI, chronic kidney disease or RCC. The term "treating" is not intended to cure disease or condition associated with AKI or chronic kidney disease. The term "treating" includes reducing or alleviating at least one adverse effect or symptom of a condition, disease or disorder, e.g., a condition associated with AKI or chronic kidney disease. Treatment is generally "effective" if one or more symptoms or clinical markers are reduced. Alternatively, treatment is "effective" if the progression of a disease is reduced or halted. That is, "treatment" includes not just the improvement of symptoms or markers (e.g., a decrease in blood levels of KIM-1 polypeptide), but also a cessation of, or at least slowing of, progress or worsening of symptoms compared to what would be expected in the absence of treatment. Beneficial or desired clinical results include, but are not limited to, alleviation of one or more symptom(s), diminishment of extent of disease, stabilized (i.e., not worsening) state of disease, delay or slowing of disease progression, amelioration or palliation of the disease state, remission (whether partial or total), and/or decreased mortality, whether detectable or undetectable. For example, treatment is considered effective if the extent or amount of AKI or chronic kidney disease or RCC tumor or metastases is reduced, or the progression of AKI or chronic kidney disease or RCC is halted. In another example, treatment is considered effective if renal function is improved. The term "treatment" of a disease also includes providing relief from the symptoms or side-effects of the disease (including palliative treatment).

As used herein, the term "treating" with respect to treatment of RCC includes reducing or alleviating at least one adverse effect or symptom of a condition, disease or disorder associated with RCC. As used herein, the term treating is used to refer to the reduction of a symptom and/or a biochemical marker of cancer by at least 10%. As a non-limiting example, a treatment can be measured by a decrease in KIM-1 protein levels in the blood as disclosed herein, for example a decrease in blood KIM-1 protein levels by at least 10% as compared to the blood KIM-1 protein levels measured in a blood sample obtained from the subject at an earlier timepoint. In some embodiments, the terms "treat" and "treatment" is administration of an appropriate therapy to the subject identified with RCC for a beneficial or desired clinical results include, but are not limited to, alleviation of symptoms, diminishment of extent of disease, stabilized (i.e., not worsening) state of disease, delay or slowing of disease progression, amelioration or palliation of the disease state, and remission (whether partial or total). "Treatment" can also mean prolonging survival as compared to expected survival if not receiving treatment. Those in need of treatment include those already diagnosed with cancer as well as those likely to develop secondary tumors due to metastasis.

The term "effective amount" as used herein refers to the amount of therapeutic agent or pharmaceutical composition to reduce or stop at least one symptom or marker of the disease or disorder, for example a symptom of AKI or cancer. For example, an effective amount using the methods as disclosed herein would be considered as the amount sufficient to reduce a symptom or marker of the disease or disorder or cancer by at least 10%. An effective amount as used herein would also include an amount sufficient to prevent or delay the development of a symptom of the disease, alter the course of a symptom disease (for example but not limited to, slowing the progression of a symptom of the disease), or reverse a symptom of the disease.

As used herein, the term "pharmaceutical composition" refers to the one or more active agents in combination with a pharmaceutically acceptable carrier e.g. a carrier commonly used in the pharmaceutical industry. The phrase "pharmaceutically acceptable" is employed herein to refer to those compounds, materials, compositions, and/or dosage forms which are, within the scope of sound medical judgment, suitable for use in contact with the tissues of human beings and animals without excessive toxicity, irritation, allergic response, or other problem or complication, commensurate with a reasonable benefit/risk ratio.

As used herein, the term "administering," refers to the placement of a compound as disclosed herein into a subject by a method or route which results in at least partial delivery of the agent at a desired site. Pharmaceutical compositions comprising the compounds disclosed herein can be administered by any appropriate route which results in an effective treatment in the subject, e.g. parenteral, intravenous, intralesional, or intratumoral. Exemplary modes of administration include, but are not limited to, injection, infusion, instillation, inhalation, or ingestion. "Injection" includes, without limitation, intravenous, intramuscular, intraarterial, intrathecal, intraventricular, intracapsular, intraorbital, intracardiac, intradermal, intraperitoneal, transtracheal, subcutaneous, subcuticular, intraarticular, sub capsular, subarachnoid, intraspinal, intracerebro spinal, and intrasternal injection and infusion. In preferred embodiments, the compositions are administered by intravenous infusion or injection. The administration can be systemic or local.

As used herein the term "comprising" or "comprises" is used in reference to compositions, methods, and respective component(s) thereof, that are essential to the invention, yet open to the inclusion of unspecified elements, whether essential or not. The term "comprises" means "includes." The abbreviation, "e.g." is derived from the Latin exempli gratia, and is used herein to indicate a non-limiting example. Thus, the abbreviation "e.g." is synonymous with the term "for example." As used herein the term "consisting essentially of" refers to those elements required for a given embodiment. The term permits the presence of elements that do not materially affect the basic and novel or functional characteristic(s) of that embodiment of the invention. The term "consisting of" refers to compositions, methods, and respective components thereof as described herein, which are exclusive of any element not recited in that description of the embodiment.

The term "statistically significant" or "significantly" refers to statistical significance and generally means a two standard deviation (2SD) difference.

As used in this specification and the appended claims, the singular forms "a," "an," and "the" include plural references unless the context clearly dictates otherwise. Thus for example, references to "the method" includes one or more methods, and/or steps of the type described herein and/or which will become apparent to those persons skilled in the art upon reading this disclosure and so forth. Similarly, the word "or" is intended to include "and" unless the context clearly indicates otherwise.

Other than in the operating examples, or where otherwise indicated, all numbers expressing quantities of ingredients or reaction conditions used herein should be understood as modified in all instances by the term "about." The term "about" when used in connection with percentages may mean±1% of the value being referred to. For example, about 100 means from 99 to 101.

All patents and other publications identified are expressly incorporated herein by reference for the purpose of describing and disclosing, for example, the methodologies described in such publications that might be used in connection with the present invention. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

Unless defined otherwise, all technical and scientific terms used herein have the same meaning as those commonly understood to one of ordinary skill in the art to which this invention pertains. Unless otherwise stated, the present invention was performed using standard procedures, as described, for example in Sambrook et al., Molecular Cloning: A Laboratory Manual (3 ed.), Cold Spring Harbor Laboratory Press, Cold Spring Harbor, N.Y., USA (2001); Davis et al., Basic Methods in Molecular Biology, Elsevier Science Publishing, Inc., New York, USA (1995); Current Protocols in Protein Science (CPPS) (John E. Coligan, et. al., ed., John Wiley and Sons, Inc.), Current Protocols in Cell Biology (CPCB) (Juan S. Bonifacino et. al. ed., John Wiley and Sons, Inc.), and Culture of Animal Cells: A Manual of Basic Technique by R. Ian Freshney, Publisher: Wiley-Liss; 5th edition (2005), Animal Cell Culture Methods (Methods in Cell Biology, Vol. 57, Jennie P. Mather and David Barnes editors, Academic Press, 1st edition, 1998) which are all incorporated by reference herein in their entireties.

KIM-1 Polypeptide

Kidney injury molecule-1 (KIM-1), also known as hepatitis A virus cellular re-ceptor 1 and T-cell immunoglobulin mucin [1], is a transmembrane glycopro-tein originally discovered using representational difference analysis in an effort to identify molecules that are significantly upregulated after acute ischemic kidney injury.[1] The ectodomain of KIM-1 (approximately 90 kD) is cleaved by matrix metalloproteinases and is present in the urine in rodents and humans after kidney proximal tubular injury.[2,3]

KIM-1, originally identified as hepatitis A virus receptor (HAVCR1, also known as Tim-1), is a type 1 transmembrane protein strongly induced by ischemic and toxic insults to kidney. The sequence of KIM-1 for a number of species is well known in the art, e.g. human KIM-1 (e.g. SEQ ID NO: 1, NCBI Ref Seq: NP_036338; NCBI Gene ID: 26762). Is encoded by 3 mRNA variants (SEQ ID NO: 2; NCBI Ref Seq: NM_012206 and SEQ ID NO: 3; NCBI Ref Seq: NM_001099414 and SEQ ID NO: 4; NCBI Ref Seq: NM_001173393)

The ectodomain of KIM-1, comprising amino acids 1 to about 295 of SEQ ID NO: 1 can be cleaved from the full-length transmembrane polypeptide, generating a soluble peptide. The ectodomain is known to comprise glycosylation, both N-linked and O-linked, which can vary by cell type or in response to stimuli (for further discussion of KIM-1 structure, see, e.g. Zhang et al. JASN 2007 18:2704-14; which is incorporated by reference herein in its entirety).

The ectodomain of KIM-1, comprising amino acids 1-295 of SEQ ID NO: 1 is as follows:

```
                                              (SEQ ID NO: 6)
mhpqvvilsl  ilhladsvag  svkvggeagp  svtlpchysg avtsmcwnrg  scslftcqng  ivwtngthvt  yrkdtrykll gdlsrrdvsl  tientavsds  gvyccrvehr  gwfndmkitv sleivppkvt  ttpivttvpt  vttvrtsttv  pttttvpmtt vptttvpttm  sipttttvlt  tmtvstttsv  ptttsipttt svpvtttvst  fvppmplprq  nhepvatsps  spqpaethpt tlqgairrep  tssplysytt  dgndtvtess  dglwnnnqtq lflehsllta  nttkg
```

KIM-1 also plays diverse roles in T and B cell biology (Rennert P D Immunol Lett.2011; 141(1):28-35). In healthy kidney, KIM-1 is undetectable, but after injury, it is induced more than any other protein, in which case it localizes to the apical surface of surviving proximal tubule epithelial cells (Ichimura T, et al. J Biol Chem. 1998; 273(7):4135-4142). The extracellular KIM-1 Ig variable domain binds and internalizes oxidized lipid as well as phosphatidylserine exposed on the outer leaflet of luminal apoptotic cells (Kobayashi N, et al. Immunity 2007; 27(6):927-940; Miyanishi et al. Nature. 2007; 450(7168):435-439), thereby aiding in nephron repair and tissue remodeling through phagocytosis of cells and debris (Ichimura et al., J Clin Invest. 2008; 118(5):1657-1668).

In one aspect, the invention provides a method of detecting kidney injury in a subject by detecting the levels of KIM-1 polypeptide in the blood of the subject.

Determining the Levels and Concentrations of KIM-1 Polypeptide in the Blood

In one aspect, the invention provides a method for diagnosing kidney injury, e.g., acute kidney injury (AKI) in a subject by measuring KIM-1 polypeptide in a blood sample obtained from the subject. In some embodiments, the methods and assays and kits as disclosed herein measure the amount of the ectodomain of KIM-1 (e.g., amino acids of SEQ ID NO: 6) in the blood obtained in the subject.

In one embodiment, the method comprises measuring the concentration of a normalizing protein, such as creatinine, and obtained from a subject; and comparing the concentration of the KIM-1 polypeptide to the concentration of normalizing protein in the sample to determine whether the subject has AKI. In one embodiment, the blood sample is a whole blood sample, a plasma sample, a serum sample or otherwise fractionated blood sample. In all such embodiments, a 5 fold increase in the concentration of KIM-1 polypeptide as compared to a reference level of blood KIM-1 polypeptide indicates the subject has AKI.

The reference level of KIM-1 polypeptide is the level of KIM-1 polypeptide in the same type of blood sample obtained from a healthy individual or the average level of KIM-1 polypeptide in blood samples obtained from a plurality of healthy subjects. Alternatively, a reference level of KIM-1 polypeptide is the level of KIM-1 polypeptide in the same type of blood sample (e.g. whole blood, plasma, serum) obtained from a subject identified not to have AKI, or the average (i.e., mean) level of KIM-1 polypeptide in the same type of blood samples obtained from a plurality of subjects identified not to have AKI. As disclosed herein in Table 1, the average plasma KIM-1 levels for normal healthy subjects was 64.4 pg/ml and the average plasma KIM-1 polypeptide levels for ICU subjects identified not to have AKI (e.g., post-cardiac surgery (CS) subjects in ICU (referred to as CS/ICS (non-AKI) subjects)) was 205.7 pg/ml. Thus, subjects with AKI (who had an average of 1458 pg/ml KIM-1 protein plasma levels) have at least a 22-fold higher level of KIM-1 polypeptide in the plasma as compared to healthy subjects, and about a 7-fold higher level of KIM-1 polypeptide in the plasma as compared to CS/ICS (non-AKI) subjects.

In some embodiments, the reference blood level of KIM-1 polypeptide is 97 pg/ml in a serum sample. Accordingly, in some embodiments, where the level of KIM-1 polypeptide in a serum sample from the subject is at or above 97 pg/ml, the subject is identified as having AKI. In some embodiments, where the level of KIM-1 polypeptide in a serum sample from the subject is at or above 97 pg/ml, the subject is administered an appropriate treatment for kidney injury or AKI or kidney disease. In some embodiments, where the level of KIM-1 polypeptide in a serum sample from the subject is at, or above 97 pg/ml, the subject is identified as being at risk of developing end stage renal disease (ESRD) during their lifetime, and sometimes within the next 5-10 years of performing the assay. Accordingly, where a subject is identified as being at risk of developing end stage renal disease (ESRD), the subject can be administered an appropriate treatment for kidney injury or AKI or kidney disease.

In some embodiments, an increase in the level of KIM-1 polypeptide that is at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 21-fold, or at least 22-fold, or at least 23-fold, or at least 24-fold, or at least 25-fold, at least about 30-fold, or at least about 40-fold, or at least about 50-fold, or more higher than a reference blood KIM-1 protein level indicates the subject has AKI.

In some embodiments, where the level of KIM-1 measured in the blood obtained from the subject is at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 21-fold, or at least 22-fold, or at least 23-fold, or at least 24-fold, or at least 25-fold, at least about 30-fold, or at least about 40-fold, or at least about 50-fold, or more higher than a reference blood KIM-1 protein level, the subject is administered an appropriate treatment for kidney injury or AKI or kidney disease, e.g., CKD.

In some embodiments, where the level of KIM-1 measured in the blood obtained from a subject is at least at or above 70 pg/ml, or at or above 80 pg/ml, or at or above 90 pg/ml, or at or above 100 pg/ml, or at or above 110 pg/ml, or at or above 120 pg/ml, or at or above 130 pg/ml, or at or above 140 pg/ml, or at or above 150 pg/ml, or above 150 pg/ml, the subject is identified as having AKI and can optionally be administered an appropriate treatment for kidney injury or AKI or kidney disease. In some embodiments, where the level of KIM-1 measured in the blood obtained from a subject is at least at or above 210 pg/ml, or at or above 250 pg/ml, or at or above 300 pg/ml, or at or above 400 pg/ml, or at or above 500 pg/ml, or at or above 600 pg/ml, or at or above 700 pg/ml, or at or above 800 pg/ml, or at or above 900 pg/ml, or above 1000 pg/ml, or above 1200 pg/ml, or above 1400 pg/ml, or above 1600 pg/ml, the subject is identified as having AKI and can optionally be administered an appropriate treatment for kidney injury or AKI or kidney disease. In some embodiments, where the level of KIM-1 measured in the blood obtained from a subject is between about 210 pg/ml-500 pg/ml, or between about 300-600 pg/ml, or between about 400-700 pg/ml, or between about 500-800 pg/ml, or between about 600-900 pg/ml, or between about 700-1000 pg/ml, or between about 800-1200 pg/ml, or between about 1000-1400 pg/ml, or between about 1200-1600 pg/ml, or at or above 900 pg/ml, or above 1000 pg/ml, or above 1200 pg/ml, or above 1400 pg/ml, or above 1600 pg/ml, the subject is identified as having AKI and can optionally be administered an appropriate treatment for kidney injury or AKI or kidney disease.

In some embodiments as disclosed herein, the level of KIM-1 polypeptide measured in the blood of a subject can be used to determine stage or progression of chronic kidney disease (CKD). In particular, in some embodiments, blood levels of KIM-1 protein, e.g., plasma levels of KIM-1 polypeptide of at least about 80 pg/ml, or at least about 83 pg/ml or at least about 85 pg/ml, but less than 94 pg/ml, or anywhere between about 80-94 pg/m indicate that the subject has stage 1 CKD, and should be monitored for CKD disease progression and/or administered an appropriate treatment for Stage 1 CKD. In particular, in some embodiments, blood levels of KIM-1 protein, e.g., plasma levels of KIM-1 polypeptide of at least about 90 pg/ml, or at least about 95 pg/ml or at least about 100 pg/ml, but less than 160 pg/ml, or anywhere between 90-160 pg/ml indicates that the subject has Stage 2 CKD, and should be monitored for CKD disease progression and/or administered an appropriate treatment for Stage 2 CKD. In some embodiments, blood levels of KIM-1 protein, e.g., plasma levels of KIM-1 polypeptide of at least about 160 pg/ml, or at least about 180 pg/ml or at least about 200 pg/ml, but less than 220 pg/ml, or between about 160-220 pg/ml, indicate that the subject has Stage 3 CKD, and should be monitored for CKD disease progression and/or administered an appropriate treatment for stage 3 CKD. In some embodiments, blood levels of KIM-1 protein, e.g., plasma levels of KIM-1 polypeptide of at least about 230 pg/ml, or at least about 240 pg/ml or at least about 250 pg/ml, or at least about 260 pg/ml, but less than 330 pg/ml, or between about 230-330 pg/ml indicate that the subject has Stage 4 CKD, and should be monitored for CKD disease progression and/or administered an appropriate treatment for stage 4 CKD. In some embodiments, blood levels of KIM-1 protein, e.g., plasma levels of KIM-1 polypeptide of at least about 340 pg/ml, or at least about 360 pg/ml or at least about 380 pg/ml or between about 340-380 pg/ml or greater than 380 pg/ml indicate that the subject has Stage 5 CKD, and should be monitored for CKD disease progression and/or administered an appropriate treatment for stage 5 CKD, e.g., a more aggressive therapy for CKD.

In some embodiments, where the level of KIM-1 measured in the blood obtained from a subject with diabetes (e.g., type I diabetes) is at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 21-fold, or at least 22-fold, or at least 23-fold, or at least 24-fold, or at least 25-fold, at least about 30-fold, or at least about 40-fold, or at least about 50-fold, or more higher than a reference blood KIM-1 protein level, the subject is identified as being at risk of developing end stage renal disease (ESRD) during their lifetime, and sometimes within the next 5-10 years of performing the assay. Accordingly, where a subject is identified as being at risk of developing end stage renal disease (ESRD), the subject can be administered an appropriate treatment for kidney injury or AKI or kidney disease.

In some embodiments, where the level of KIM-1 measured in the blood obtained from a subject with diabetes (e.g., type I diabetes) is at least at or above 70 pg/ml, or at or above 80 pg/ml, or at or above 90 pg/ml, or at or above 100 pg/ml, or at or above 110 pg/ml, or at or above 120 pg/ml, or at or above 130 pg/ml, or at or above 140 pg/ml, or at or above 150 pg/ml, or above 150 pg/ml, the subject is identified as being at risk of developing end stage renal disease (ESRD) during their lifetime, and sometimes within the next 5-10 years of performing the assay. In some embodiments, where the level of KIM-1 measured in the blood obtained from a subject with diabetes (e.g., type I diabetes) is at least, or above 97 pg/ml, the subject is identified as being at risk of developing end stage renal disease (ESRD) during their lifetime, and sometimes within the next 5-10 years of performing the assay, and the subject is administered with an appropriate treatment for kidney injury or AKI. Accordingly, where a subject is identified as being at risk of developing end stage renal disease (ESRD), the subject can be administered an appropriate treatment for kidney injury or AKI or kidney disease.

In some embodiments as disclosed herein, the level of KIM-1 polypeptide measured in the blood obtained from a subject with diabetes, e.g. a subject with type I diabetes can be used to determine stage or progression of chronic kidney disease (CKD) in the subject. In particular, in some embodiments, blood levels of KIM-1 protein, e.g., serum levels of KIM-1 polypeptide in a diabetic subject of at least about 80 pg/ml, or at least about 85 pg/ml or at least about 89 pg/ml, but less than 125 pg/ml, or anywhere between about 80-125 pg/ml, indicates that the diabetic subject has stage 1 CKD, and should be monitored for CKD disease progression and/or administered an appropriate treatment for Stage 1 CKD. In some embodiments, blood levels of KIM-1 protein, e.g., serum levels of KIM-1 polypeptide in a diabetic subject of at least about 130 pg/ml, or at least about 140 pg/ml or at least about 150 pg/ml, or at least about 158 pg/ml, but less than 165 pg/ml, or anywhere between 130-165 pg/ml, indicates that the diabetic subject has Stage 2 CKD, and should be monitored for CKD disease progression and/or administered an appropriate treatment for Stage 2 CKD. In some embodiments, blood levels of KIM-1 protein, e.g., serum levels of KIM-1 polypeptide in a diabetic subject of at least about 170 pg/ml, or at least about 175 pg/ml or at least about 181 pg/ml, but less than 250 pg/ml, or anywhere between about 170-250 pg/ml, indicates that the diabetic subject has Stage 3 CKD, and should be monitored for CKD disease progression and/or administered an appropriate treatment for stage 3 CKD. In some embodiments, blood levels of KIM-1 protein, e.g., serum levels of KIM-1 polypeptide in the diabetic subject of at least about 260 pg/ml, or at least about 270 pg/ml or at least about 280 pg/ml, but less than 280 pg/ml, or anywhere between about 260-280 pg/ml, indicates that the diabetic subject has Stage 4 CKD, and should be monitored for CKD disease progression and/or administered an appropriate treatment for stage 4 CKD, e.g., a more aggressive therapy for CKD. In some embodiments, blood levels of KIM-1 protein, e.g., serum levels of KIM-1 polypeptide in the diabetic subject of at least about 500 pg/ml, or at least about 600 pg/ml or at least about 700/m1 or between about 450-800 pg/ml or greater than 800 pg/ml indicate that the diabetic subject has Stage 5 CKD, and should be monitored for CKD disease progression and/or administered an appropriate treatment for stage 4 CKD, e.g., a more aggressive therapy for CKD.

In some embodiments as disclosed herein, the level of KIM-1 polypeptide measured in the blood obtained from a subject with, or suspected to have RCC, e.g. a subject with a predisposition of RCC or a symptom of RCC can be used to determine the stage or progression of RCC in the subject. In some embodiments, where the level of KIM-1 measured in the blood obtained from the subject is at least 4-fold, or at least 5-fold, or at least 6-fold, or at least 7-fold, or at least 8-fold, or at least 9-fold, or at least 10-fold, or at least 11-fold, or at least 12-fold, or at least 13-fold, or at least 14-fold, or at least 15-fold, or at least 16-fold, or at least 17-fold, or at least 18-fold, or at least 19-fold, or at least 20-fold, or at least 21-fold, or at least 22-fold, or at least 23-fold, or at least 24-fold, or at least 25-fold, at least about 30-fold, or at least about 40-fold, or at least about 50-fold, or more higher than a reference blood KIM-1 protein level, the subject is identified as having RCC, e.g., ccRCC and can be administered an appropriate treatment for RCC.

In some embodiments, where the level of KIM-1 measured in the blood obtained from a subject with RCC is at least at or above 400 pg/ml, or at or above 450 pg/ml, or at or above 500 pg/ml, or at or above 550 pg/ml, or at or above 600 pg/ml, or above 600 pg/ml, the subject with RCC is identified as being at risk of having a more aggressive RCC, or severe RCC progression and/or an increased risk of reduced survival as compared to a subject with RCC having a KIM-1 plasma level similar to a reference level, or less than about 400 pg/ml. In some embodiments, where the level of KIM-1 measured in the blood obtained from a subject with RCC is at least, or above 550 pg/ml, the subject is identified as having a more aggressive RCC disease and more severe RCC progression and increased risk of reduced survival as compared to a subject with RCC having a KIM-1 plasma level similar to a reference level, or less than about 550 pg/ml. Accordingly, where a subject is identified as having a more aggressive RCC, or severe RCC progression and/or an increased risk of reduced survival, the subject can be administered an aggressive therapy for RCC.

In some embodiments as disclosed herein, the level of KIM-1 polypeptide measured in the blood of a subject can be used to determine stage or progression of RCC in a subject and can be used to determine the appropriate treatment regimen, e.g., an a more aggressive treatment for subject identified with a high level of KIM-1 plasma levels. In particular, in some embodiments, blood levels of KIM-1 protein, e.g., plasma levels of KIM-1 polypeptide of at least about 100 pg/ml, or at least about 110 pg/ml or at least about 120 pg/ml, but less than 145 pg/ml, or anywhere between about 100-145 pg/ml indicate that the subject has grade 1 (G1) RCC, and should be monitored for RCC disease progression and/or administered an appropriate treatment for grade 1 RCC. In some embodiments, blood levels of KIM-1 protein, e.g., plasma levels of KIM-1 polypeptide of at least about 150 pg/ml, or at least about 200 pg/ml or at least about 400 pg/ml, but less than 900 pg/ml, or anywhere between 150-900 pg/ml indicates that the subject has grade 2 (G2) RCC, and should be monitored for RCC disease progression and/or administered an appropriate treatment for grade 2 RCC. In some embodiments, blood levels of KIM-1 protein, e.g., plasma levels of KIM-1 polypeptide of at least about 950 pg/ml, or at least about 1000 pg/ml or at least about 1100 pg/ml, but less than 1200 pg/ml, or between about 950-1200 pg/ml, indicate that the subject has grade 3 (G3) RCC, and should be monitored for RCC disease progression and/or administered an appropriate treatment for grade 3 RCC. In some embodiments, blood levels of KIM-1 protein, e.g., plasma levels of KIM-1 polypeptide of at least about 1200 pg/ml, or at least about 1300 pg/ml or at least about 1400 pg/ml, or at least about 1500 pg/ml, or more than 1500 pg/ml indicate that the subject has grade 4 (G4) RCC, and should be monitored for RCC disease progression and/or administered an appropriate treatment for grade 4 RCC.

In another embodiment, the method comprises contacting a blood sample obtained from a subject in need thereof with at least one agent that specifically binds to KIM-1 polypeptide, e.g., the ectodomain of KIM-1 polypeptide. In some embodiment, the method further comprises also contacting the blood sample obtained from a subject in need thereof with at least one agent specific for a normalizing protein, such as creatinine, where the agents specific for KIM-1 and the normalizing protein are used in an assay to determine the level or concentration of the KIM-1 polypeptide and the level or concentration of the normalizing protein; and diagnosing a subject with AKI based on the level or concentration of the blood KIM-1 polypeptide. In some embodiments, the method further comprises determining a therapeutic treatment for the subject.

In one embodiment, the concentration or level of the blood KIM-1 polypeptide from the subject is compared with a reference concentration or level of blood KIM-1 polypeptide (e.g., the concentration or level of blood KIM-1 polypeptide from a healthy individual or plurality of healthy individuals, or a subject or plurality of subjects who are confirmed not to have AKI), and where there is a >5 fold increase in the concentration or level of KIM-1 polypeptide in the blood obtained from the subject as compared to a reference blood level or concentration of KIM-1 polypeptide indicates the subject has AKI. In one embodiment, the concentration of the blood KIM-1 polypeptide is compared with the concentration of the normalizing protein (e.g., creatinine and/or albumin as the normalizing protein), where at least a 4-fold increase in the KIM-1 polypeptide over the normalizing protein is indicative of AKI in the subject. In other embodiments, the level or concentration of the KIM-1 polypeptide is measured by measuring the activity of the KIM-1 protein, but methods commonly known to persons of ordinary skill in the art.

In some embodiments, the reference blood level or concentration of KIM-1 is obtained from an individual subject or plurality of subjects that do not have AKI. Blood levels of KIM-1 polypeptide higher than blood levels for KIM-1 that are observed in the normal control indicates the subject has AKI or is at risk for AKI. The blood levels of KIM-1 can be represented in protein amount/volume (e.g., pg/ml, pg/μl, ng/ml, ng/μl, or g/ml etc.) or by arbitrary units, for example as units obtained from a densitometer, luminometer, or an ELISA plate reader.

In one embodiment of the aspect, a secondary diagnostic step can be performed. For example, if a level of KIM-1 in the blood is found to indicate the presence of AKI, then an additional method of detecting the injury can be performed to confirm the injury or further assess the extent of injury. Any of a variety of additional diagnostic steps can be used, such as ultrasound, PET scanning, MRI, or any other imaging techniques, biopsy, clinical examination, ductogram, or any other method.

The present invention further provides for methods of prognostic evaluation of a patient suspected of having, or having, AKI. The method comprises measuring the level of KIM-1 protein in the blood obtained from a patient and comparing the observed level with a range of KIM-1 protein levels normally found in blood samples (of the same type, e.g., whole blood, plasma, serum etc.) of healthy individuals. A high level for example, corresponds to a poor prognosis, while lower levels indicate that the injury is less severe and corresponds to a better prognosis. In some embodiments, where there is about a 4-fold increase in the level of KIM-1 protein in the blood sample from the subject as compared to the level found in healthy subjects indicates that the AKI is less severe than a subject who has AKI and is identified as having, for example, a >4-fold, or >5-fold, or >6-fold, or >10-fold, or a >15-fold, or a >20-fold increase in the level of KIM-1 protein in the blood sample as compared to the KIM-1 protein levels normally found in blood samples from healthy individuals.

Additionally, resolution of the kidney injury can be assessed by following the blood levels or concentrations of KIM-1 protein in an individual patient. For example, changes in the patients condition can be monitored by comparing changes in the blood level of KIM-1 in the patient over time. Progressive increases in the levels or concentrations of KIM-1 protein is indicative of increased potential for adverse outcome (e.g., mortality).

Measuring levels or concentrations of KIM-1 polypeptide, can be measured by any means known to those skilled in the art. See., e.g., U.S. patent application Ser. No. 11/829,323, including ELISA, multiplex bead, mass spectrometry, and PCR assays. The antibodies for use in the present invention can be obtained from a commercial source, or prepared by well-known methods.

The terms "increased concentration", "increase in the level", "higher level", or "higher concentration" of a KIM-1 protein refers to a level or concentration of KIM-1 polypeptide biomarker that is statistically significant or significantly above the level or concentration of that biomarker found in a control or reference sample, in a sample from the same subject at a different timepoint, or relative to a reference concentration or level. As used herein, the phrase "higher level" or "increase in the level" can be for example 3.9-fold, or 4.0-fold or higher, for example, 4.5-fold or 5.0-fold higher or higher than 5-fold. Similarly, an AUC value of about 0.78 may be considered statistically significant. For purposes of comparison, the test sample and control sample are from the same sample type, that is, obtained from the same biological source (e.g., plasma, serum or whole blood).

As used herein, the term "normalizing protein" or "normalizing factor" refers to a protein against which the amounts of a biomarker of interest are normalized to, to permit comparison of amounts of the protein of interest in different biological samples. In some embodiments, the normalizing protein is creatinine or albumin. In some embodiments, the different biological samples are from different subjects. In other embodiments, the different biological samples are from the same subject, but after different timepoints. Generally, a normalizing protein is constitutively expressed and is not differentially regulated between at least two physiological states or conditions from which samples will be analyzed, e.g., given disease and non-disease states. Thus, for example, a normalizing protein does not vary substantially (i.e., <15%, preferably <10%, <7%, <5%, <4%, <3%, <2%, <1% or less) in the presence and absence of e.g., acute kidney disease. In one embodiment, a normalizing protein is selected based on the degree of correlation (e.g., lowest amount of scatter or lowest standard deviation among replicates) of the protein measured over a series of sample dilutions, compared to the predicted relationship of the dilution series (e.g., predicted by linear regression). In this embodiment, a normalizing protein is selected that has the highest degree of correlation (e.g., as compared to another protein in a protein sample subjected to the same measurement) for measured protein levels assessed over the dilution series. The term "highest degree of correlation" refers to a standard deviation for protein measurements (e.g., replicate measurements) over a dilution series of less than 2 compared to the predicted relationship over the dilution series; preferably the standard deviation is less than 1.5, less than 1, less than 0.5, less than 0.1, less than 0.01, less than 0.001 or more, including a standard deviation of zero (e.g., measured and predicted values are the same). In some embodiments, the normalizing protein is the product of a "housekeeping gene". As referred to herein, the term "housekeeping gene" refers to a gene encoding a protein that is constitutively expressed, and is necessary for basic maintenance and essential cellular functions. A housekeeping gene generally is not expressed in a cell- or tissue-dependent manner, most often being expressed by all cells in a given organism. Some examples of normalizing proteins encoded by housekeeping genes include e.g., actin, tubulin, GAPDH, among others. In one embodiment, a housekeeping gene product is used as a normalizing protein.

Measuring Protein Levels of KIM-1 in a Blood Sample

The invention provides, in part, a variety of assay formats that can be used to determine the concentration or level of KIM-1 protein, and optionally, a normalizing protein. Examples of assay formats include known techniques such as Western blot analysis, radioimmunoassay (hereinafter referred to as "RIA"), Immunoradiometric assay (IRMA), chemiluminescent immunoassays, such as enzyme-linked immunosorbent assay (hereinafter referred to as "ELISA"), multiplex bead assays, a fluorescence antibody method, passive haemagglutination, mass spectrometry (such as MALDI/TOF (time-of-flight), SELDI/TOF), liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, and tandem mass spectrometry HPLC. Some of the immunoassays can be easily automated by the use of appropriate instruments such as the IM x™ (Abbott, Irving, Tex.) for a fluorescent immunoassay and Ciba Corning ACS 180™ (Ciba Corning, Medfield, Mass.) for a chemiluminescent immunoassay.

In some embodiments, an agent which specifically binds to KIM-1 is an antibody or antibody fragment (e.g., an antigen-binding Ab fragment), or a protein-binding molecule which specifically binds an expression product of KIM-1. In some embodiments, an agent which specifically binds to KIM-1 is an antibody or antibody fragment (e.g., an antigen-binding Ab fragment), or a protein-binding molecule which a KIM-1 polypeptide.

In some embodiments, an agent which specifically binds to KIM-1 is an antibody or antibody fragment (e.g., an antigen-binding Ab fragment), or a protein-binding molecule which can specifically bind the KIM-1 ectodomain, either cleaved or uncleaved. In some embodiments, an agent which specifically binds to KIM-1 is an antibody or antibody fragment (e.g., an antigen-binding Ab fragment), or a protein-binding molecule can bind glycosylated or partially glycosylated KIM-1 polypeptide. In some embodiments, an agent which specifically binds to KIM-1 is an antibody or antibody fragment (e.g., an antigen-binding Ab fragment), or a protein-binding molecule can bind unglycosylated KIM-1 polypeptide. In some embodiments, an agent which specifically binds to KIM-1 is an antibody or antibody fragment (e.g., an antigen-binding Ab fragment), or a protein-binding molecule can bind to glycosylated, or partially glycosylated, or unglycosylated ectodomain of KIM-1 polypeptide, e.g., to glycosylated, or partially glycosylated, or unglycosylated protein or fragment of SEQ ID NO: 6.

In some embodiments, an agent which specifically binds to KIM-1 is small or large organic or inorganic molecule. As used herein, the term "small molecule" refers to natural or synthetic molecules having a molecular weight less than about 10,000 grams per mole, organic or inorganic compounds having a molecular weight less than about 5,000 grams per mole, than about 1,000 grams per mole, or less than about 500 grams per mole.

In some embodiments, an agent which specifically binds to KIM-1 is an antibody or antibody fragment (e.g., an antigen-binding Ab fragment), or a protein-binding molecule. Suitable antibodies include, but are not limited to, polyclonal, monoclonal, chimeric, humanized, recombinant, single chain, $F_{ab}$, $F_{ab'}$, $F_{sc}$, $R_v$, and $F_{(ab')2}$ fragments, and an $F_{ab}$ expression library. In some embodiments, neutralizing antibodies can be used an agent which specifically binds to KIM-1. Antibodies are readily raised in animals such as rabbits or mice by immunization with the antigen. Immunized mice are particularly useful for providing sources of B cells for the manufacture of hybridomas, which in turn are cultured to produce large quantities of monoclonal antibodies. In general, an antibody molecule obtained from humans can be classified in one of the immunoglobulin classes IgG, IgM, IgA, IgE and IgD, which differ from one another by the nature of the heavy chain present in the molecule. Certain classes have subclasses as well, such as $IgG_1$, $IgG_2$, and others. Furthermore, in humans, the light chain may be a kappa chain or a lambda chain. Reference herein to antibodies includes a reference to all such classes, subclasses and types of human antibody species.

Antibodies provide high binding avidity and unique specificity to a wide range of target antigens and haptens. Monoclonal antibodies useful in the practice of the methods disclosed herein include whole antibody and fragments thereof and are generated in accordance with conventional techniques, such as hybridoma synthesis, recombinant DNA techniques and protein synthesis.

The extracellular domain of the KIM-1 polypeptide, or a portion or fragment thereof, can serve as an antigen, and additionally can be used as an immunogen to generate antibodies that immunospecifically bind the antigen, using standard techniques for polyclonal and monoclonal antibody preparation. Preferably, the antigenic peptide comprises at least 10 amino acid residues, or at least 15 amino acid residues, or at least 20 amino acid residues, or at least 30 amino acid residues. In some embodiments, an agent which specifically binds to KIM-1 is an antibody or antibody fragment (e.g., an antigen-binding Ab fragment), or a protein-binding molecule binds to an epitope within, overlapping, or in close proximity to the amino acid sequence SSDGLWNNNQTQLFLEHS (SEQ ID NO: 5) in KIM-1.

Useful monoclonal antibodies and fragments can be derived from any species (including humans) or can be formed as chimeric proteins which employ sequences from more than one species. Human monoclonal antibodies or "humanized" murine antibody are also used in accordance with the present invention. For example, murine monoclonal antibody can be "humanized" by genetically recombining the nucleotide sequence encoding the murine Fv region (i.e., containing the antigen binding sites) or the complementarily determining regions thereof with the nucleotide sequence encoding a human constant domain region and an Fc region. Humanized targeting moieties are recognized to decrease the immunoreactivity of the antibody or polypeptide in the host recipient, permitting an increase in the half-life and a reduction the possibly of adverse immune reactions in a manner similar to that disclosed in European Patent Application No. 0,411,893 A2. The murine monoclonal antibodies should preferably be employed in humanized form. Antigen binding activity is determined by the sequences and conformation of the amino acids of the six complementarily determining regions (CDRs) that are located (three each) on the light and heavy chains of the variable portion (Fv) of the antibody. The 25-kDa single-chain Fv (scFv) molecule, composed of a variable region (VL) of the light chain and a variable region (VH) of the heavy chain joined via a short peptide spacer sequence, is the smallest antibody fragment developed to date. Techniques have been developed to display scFv molecules on the surface of filamentous phage that contain the gene for the scFv. scFv molecules with a broad range of antigenic-specificities can be present in a single large pool of scFv-phage library. Some examples of high affinity monoclonal antibodies and chimeric derivatives thereof, useful in the methods of the present invention, are described in the European Patent Application EP 186,833; PCT Patent Application WO 92/16553; and U.S. Pat. No. 6,090,923.

Chimeric antibodies are immunoglobin molecules characterized by two or more segments or portions derived from different animal species. Generally, the variable region of the chimeric antibody is derived from a non-human mammalian antibody, such as murine monoclonal antibody, and the immunoglobin constant region is derived from a human immunoglobin molecule. Preferably, both regions and the combination have low immunogenicity as routinely determined.

Exemplary antibodies which can be used to detect KIM-1 polypeptide are disclosed in U.S. Pat. No. 7,300,652 (e.g., ABE3, AKG7, or ACA12), U.S. Pat. No. 7,696,321 (e.g., ABE3, AKG7, or ACA12), U.S. Pat. Nos. 7,597,887, 7,041,290 (e.g., ABE3, AKG7, or ACA12), US20050084449 (e.g., 1.29, 2.56.2, 2.59.2, and 2.45.1), WO2013078089, and US20130202527 (e.g., 1.29, 2.56.2, 2.59.2, and 2.45.1), the contents of each of which are incorporated herein by reference for its teachings of anti-KIM-1 antibodies.

KIM-1 antibodies are also commercially available from vendors such as Biorbyt (Cambridge, UK), GeneTex (Irvine, USA), Aviva Systems Biology (Beijing, CN), Bioss Inc. (Woburn, USA), Sino Biological (Beijing CN), Acris Antibodies GmbH (San Diego, USA), Raybiotech, Inc. (Norcross, USA), OriGene Technologies (Rockville, USA), Enzo Life Sciences (Farmingdale, USA), and Abcam (Cambridge, UK).

Furthermore, KIM-1 polypeptide in the blood can be detected using assays as disclosed Sabbisetti et al., Novel Assays for Detection of Urinary KIM-1 in mouse models of Kidney injury (Technological sciences, 2013; 131(1); 13-25 (which is incorporated herein in its entirety by reference), which can be adapted by one of ordinary skill in the art to detect KIM-1 polypeptide in a blood sample, such as, e.g., a whole blood sample, a plasma sample, serum sample or other fractionated blood sample.

An agent which specifically binds to KIM-1 polypepdie, e.g., an antibody or antibody fragment (e.g., an antigen-binding Ab fragment), or a protein-binding molecule which specifically binds an expression product of KIM-1

RIA and ELISA provide the benefit of detection sensitivity, rapidity, accuracy, possible automation of procedures, and the like, for the determination of the concentration or level of KIM-1 polypeptide biomarker (Modern Rheumatology 13: 22-26 (2003)), Ohkuni et al., (International Congress Series 1289: 71-74 (2006)), and Mitchell et al., (Mol Microbiol. 5: 1883-8 (1991)). Radioimmunoassay (Kashyap, M. L. et al., J. Clin. Invest., 60:171-180 (1977)) is a technique in which detection antibody can be used after labeling with a radioactive isotope such as 125I. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

The most common enzyme immunoassay is the "Enzyme-Linked Immunosorbent Assay (ELISA). There are different forms of ELISA which are well known to those skilled in the art, e.g. standard ELISA, competitive ELISA, and sandwich ELISA. The standard techniques for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904. ELISA is a technique for detecting and measuring the concentration of an antigen, such as an acute kidney injury biomarker, using a labeled (e.g. enzyme linked) form of the antibody. In a "sandwich ELISA", an antibody is linked to a solid phase (i.e. a microtiter plate) and exposed to a biological sample containing antigen (e.g. an acute kidney injury biomarker). The solid phase is then washed to remove unbound antigen. A labeled antibody (e.g. enzyme linked) is then bound to the plate bound-antigen (if present) forming an antibody-antigen-antibody sandwich.

Examples of enzymes that can be linked to the antibody are alkaline phosphatase, horseradish peroxidase, luciferase, urease, and B-galactosidase. The enzyme linked antibody reacts with a substrate to generate a colored reaction product that can be measured. In a "competitive ELISA", a specific concentration of an antibody specific for KIM-1 polypeptide is incubated with a blood sample. The KIM-1-antibody mixture is then contacted with a solid phase (e.g. a microtiter plate) that is coated with KIM-1 protein biomarker. The more KIM-1 biomarker present in the sample, the less free antibody that will be available to bind to the solid phase. A labeled (e.g., enzyme linked) secondary antibody is then added to the solid phase to determine the amount of primary antibody bound to the solid phase.

In some embodiments, the concentration of KIM-1 biomarkers can be determined simultaneously, in a multiplex fashion, by ELISA (enzyme-linked immunosorbent assay). The blood sample can be, for example, one of a plurality of blood samples obtained at one of the various timepoints from a subject in need. In some embodiments, the blood sample is a human blood sample from a subject, to be tested for determining the concentration of KIM-1 protein according to the methods described herein. The blood sample (e.g., plasma, serum etc.) from the individual may further be serially diluted, according to the needs of the assay, and as known to one of ordinary skill in the art. In some embodiments, one or more of a plurality of antibodies or antigen-binding fragments specific for KIM-1 being assayed in a sample is contacted with the blood sample to bind KIM-1 protein present in the sample, thus forming a KIM-1-antibody complex or KIM-1-antigen-binding fragment complex. In some embodiments, each antibody or antigen-binding fragment specific for KIM-1 is labeled with a different label. In some embodiments, each different label is a fluorescent label. In all such embodiments, each different label has a unique emission spectra, such that each antibody can be detected individually. The levels or concentrations of KIM-1 can then be determined by calculating changes in the emission spectrum, wherein the relative intensity of signal from each of the fluorescent labels correlates with the number of antibodies against the particular biomarker being assayed. For example, a well that displays a more intense signal of the label on the antibody against KIM-1 will have a greater concentration of KIM-1 than a well with a weak signal for that particular label. The wells can be normalized to a well comprising all of the necessary ELISA reagents with the exception of the sample. A series of standards having known concentrations of each of the various biomarkers being assayed permits actual quantification of the concentration of each of the biomarkers in the sample.

In some aspects, the concentration or level of KIM-1 can be determined alone, or in combination with other blood biomarkers (e.g., other blood biomarkers for AKI such as for example, albumin or serum creatinine, or other disease pathologies, or a normalizing protein biomarker) simultaneously, in a multiplex fashion, using a multiplex bead assay. For example, in one embodiment, beads of different sizes or colors (emission spectra) are used for multiplexed immunoassays to determine the concentration of KIM-1 and optionally, one or more other blood biomarkers. In some embodiments of this aspect, a plurality of beads of different sizes are coated with different antibodies, wherein each bead of a specific size is conjugated to an antibody specific for a single biomarker (e.g., a bead of one size is conjugated to an antibody for KIM-1 and beads of different sizes are conjugated to different antibodies specific to different blood biomarkers, or antibodies specific to normalizing proteins).

Accordingly, each bead can be differentiated by its unique light scatter characteristics. A blood sample, such as a plasma or serum sample, to be assayed for the presence of KIM-1 protein and optionally at least one other blood biomarker is then contacted with a plurality of beads of different sizes, forming a bead-biomarker conjugate, and the concentrations of KIM-1 and the other blood biomarker can then be ascertained by, for example, performing flow cytometric analyses on the bead bound-sample. In some embodiments, one of the other blood biomarkers assessed in a multiplex bead assay is a normalizing protein to detect the level of protein in the blood sample. In some embodiments, a blood biomarker assessed with KIM-1 biomarker is selected from any of albuiminura or creatinine or a combination of albuiminura and creatinine.

In some embodiments of this aspect, such bead-based technology can be employed wherein bead populations are identified by one type of fluorescence, while the biomarker-dependent signal is generated by detection reagents carrying a second type of fluorescent signal, thus creating a bead set specific for KIM-1 and one or more other biomarkers (e.g., normalizing proteins and/or albuiminura and/or creatinine). In preferred embodiments, the distinguishable bead populations are prepared by staining the beads with two or more fluorescent dyes at various ratios. Each bead having a specific ratio of the two or more fluorescent dyes is conjugated to an antibody specific for one of a plurality of biomarkers, thus assigning each bead a unique fluorescent signature. The immunoassay signal is generated by detection reagents, coupled to a third type of fluorescent dye. A sample to be assayed for the presence of KIM-1 and optionally at least one other biomarker, is then contacted with the plurality of beads with unique fluorescent signatures and biomarker specificity, forming a bead-biomarker conjugate for KIM-1 or other biomarker present in the sample. The concentrations of KIM-1 and each of other proteins or biomarkers can be ascertained by flow cytometric analyses on the bead bound-sample. For example, in some embodiments, beads are dyed with fluorochromes having different fluorescence intensities. In some embodiments, the beads are 7.5 μm in diameter. In some embodiments, the fluorescent dye incorporated in the beads fluoresces strongly at 650 nm upon excitation with an argon laser. Each bead population of a given fluorescence intensity represents a discrete population for constructing an immunoassay for a single biomarker. Each bead population having a given fluorescence intensity upon excitation is covalently coupled with an antibody directed against a specific biomarker, e.g., an antibody directed against KIM-1. These antibody-bound bead populations, each of which are unique in their fluorescence emission intensity, serve as capture beads for KIM-1 and optionally, a combination of other proteins or biomarkers (e.g., albuiminura and/or creatinine) in a sample.

Accordingly, as defined herein a "capture bead" is a bead having a unique fluorescence emission intensity conjugated to an antibody specific for a biomarker, e.g., KIM-1. When these capture beads specific for different biomarkers are used as a mixture, the levels of individual biomarkers, such as KIM-1 and albuiminura and/or creatinine, can be simultaneously measured within a given blood sample. In some embodiments, detection is further mediated by the binding of a specific detection antibody, for example, an antibody that detects any bead-biomarker complex present in a sample, that is directly conjugated with phycoerythrin (PE), to each of the corresponding capture bead-biomarker complexes present in the sample, thus providing a second fluorescent signal for each capture bead. The fluorescent signal is proportional to the concentration of the biomarker in the sample. Separately established calibration curves can be used to determine the concentration of each biomarker in the test sample, using dedicated analysis software, such as CBA software. The data collected using a flow cytometer include information about the physical and spectral parameters of the beads, such as size and the fluorescence emission characteristics of each bead population. These fluorescence emission characteristics include the fluorescent emission of the dyed beads, and the potential fluorescent emissions of the detection fluorochrome (for example, phycoerythrin). When samples are analyzed using a flow cytometer in conjunction with a typical data acquisition and analysis package (for e.g., BD CellQuest™ software), a list-mode data file is saved using a flow cytometry standard file format, FCS. The data stored in the FCS files can be reanalyzed to determine the median fluorescence intensities (MFI) of the various bead populations, defined by their unique physical and spectral characteristics, to then compare reference samples with unknowns. The level of the biomarkers, e.g., KIM-1 being assayed within individual blood samples can then be calculated from calibration curves generated by serial dilutions of standard analyte solutions of known concentration. An automated or semiautomated analysis method can be used for rapid reanalysis of the data stored in each FCS file. For example, BD CBA Software is written in the Microsoft® Excel Visual Basic for Applications (VBA) programming language. The CBA Software can recognize FCS 2.0 and 3.0 format data files and automates the identification of CBA bead populations and the determination of detector fluorochrome MFI values for each bead population within the data file for a single sample. Using this data analysis function of the CBA Software for multiple standard files, the MFI values for standards are then determined and plotted. From the plotted standard curve and complex mathematical interpolation, values for unknown samples can be rapidly determined in comparison to known standards using the software.

Other techniques can be used to detect blood levels of KIM-1 protein as required to practice the methods described herein, according to a practitioner's preference, and based upon the present disclosure. The suitability of a given method for measuring KIM-1 levels will depend on the ability of that method or assay to distinguish between KIM-1 and other proteins in the blood sample. Thus, an immunoassay can distinguish on the basis of selective binding to KIM-1 and not another agent or protein in the blood sample. Spectrometric approaches can be applied when a given agent will have a distinct spectrum or profile in the assay relative to others. One such technique is Western blotting (Towbin et at., Proc. Nat. Acad. Sci. 76:4350 (1979)), wherein a suitably treated sample is run on an SDS-PAGE gel before being transferred to a solid support, such as a nitrocellulose filter. Detectably labeled antibodies that specifically bind to the KIM-1 can then be used to detect KIM-1 levels or concentrations, where the intensity of the signal from the detectable label corresponds to the amount of KIM-1 protein present. Levels can be quantitated, for example by densitometry.

The prognostic methods of the invention also are useful for determining a proper course of treatment for a patient having AKI. A course of treatment refers to the therapeutic measures taken for a patient after diagnosis or after treatment for injury.

The present invention is also directed to commercial kits for the detection and prognostic evaluation of AKI. The kit can be in any configuration well known to those skilled in the art and is useful for performing one or more of the methods described herein for the detection of KIM-1 polypeptide in the blood. The kits are convenient in that they supply many, if not all, of the essential reagents for conducting an assay for the detection of KIM-1 polypeptide in a blood test sample, such as described herein. In addition, the assay may be performed simultaneously with a standard or multiple standards included in the kit, such as a predetermined amount of a KIM-1 polypeptide, so that the results of the test can be quantified or validated.

In one embodiment, the kit comprises a means for detecting levels of a KIM-1 polypeptide in a sample of blood, or sample of plasma or sample of serum obtained from the subject. The kit may comprise a "dipstick" with at least one KIM-1 polypeptide binding agent immobilized thereon, which specifically binds to KIM-1 protein. Specifically bound KIM-1 protein can then be detected using, for example, a second antibody that is detectably labeled with a calorimetric agent or radioisotope.

In some embodiments, a kit comprises a paper-based assay to determine levels of KIM-1 polypeptide in a blood sample. Such paper-based assays are well known in the art, e.g., as disclosed in International Application WO 2011097412 and U.S. Pat. No. 8,821,810 and US application US 2014/0193840 and published documents by Martinez et al., (2007), Patterned Paper as a Platform for Inexpensive, Low-Volume, Portable Bioassays. Angewandte Chemie International Edition. 2007; 46(8):1318-1320, and Chung et al., (2010) Paper-Based ELISA. Angewandte Chemie International Edition; 2010; 49(28):4771-4774, which are all incorporated herein in their entireties by reference.

In other embodiments, the assay kits may contain components for competitive and non-competitive assays, radioimmunoassay (RIA), multiplex bead assays, bioluminescence and chemiluminescence assays, fluorometric assays, sandwich assays, immunoradiometric assays, dot blots, enzyme linked assays including ELISA, microtiter plates, or immunocytochemistry. For each kit the range, sensitivity, precision, reliability, specificity, and reproducibility of the assay are established by means well known to those skilled in the art.

In one embodiment, methods to detect the RCC proteins and fragments and functional variants thereof as disclosed herein include ELISA (enzyme linked immunosorbent assay), western blot, immunoprecipitation, immunofluorescence using detection reagents such as an antibody or protein binding molecules or protein-binding agents. Alternatively, a RCC protein biomarker can be detected in a subject by introducing into a subject a labeled anti-RCC biomarker antibody and other types of detection agent. For example, the antibody can be labeled with a radioactive marker whose presence and location in the subject is detected by standard imaging techniques, particularly useful are methods that detect a RCC protein or fragment thereof expressed in a subject or in a biological sample.

Methods to detect level the KIM-1 polypeptide in a blood sample are well known to persons skilled in the art, and are encompassed for use in this invention. Commercially available antibodies and/or ELISA kits for detection of the expression of the KIM-1 polypeptide in a blood sample are also useful in the methods of this invention. Some examples of such protein-binding molecules useful to detect the the KIM-1 polypeptide are commercially available, and include, but are not limited to, commercially available antibodies from Cell Signalling Technologies (MA, USA), which can be found at world wide web site: "cellsignal-dot-com". In some embodiments, antibodies from other antibody companies, such as for example, Abnova corporation, Anogen, Alpco Diagnostics, Ray Biotech, alphagenix, autogen, R&D Systems, Pepro Tech EC Ltd, cytolab, Bender MedSystems GmbH, Biovision Research Products, EBD biosciences, Chemicon, Axxora Platform, Promo Cell Distrubuters, Cell Science, Santa Cruz Biotechnology, Sigma etc. can be used. In alternative embodiments, antibodies directed against the KIM-1 polypeptide and/or its ectodomain can also be used in disease diagnostics and prognostics.

In another embodiment, immunohistochemistry ("IHC") and immunocytochemistry ("ICC") techniques can be used. IHC is the application of immunochemistry to tissue sections, whereas ICC is the application of immunochemistry to cells or tissue imprints after they have undergone specific cytological preparations such as, for example, liquid-based preparations Immunochemistry is a family of techniques based on the use of a antibody, wherein the antibodies are used to specifically target molecules inside or on the surface of cells. The antibody typically contains a marker that will undergo a biochemical reaction, and thereby experience a change color, upon encountering the targeted molecules. In some instances, signal amplification can be integrated into the particular protocol, wherein a secondary antibody, that includes the marker stain or marker signal, follows the application of a primary specific antibody.

In some embodiments, the methods as described herein can be performed, for example, by utilizing pre-packaged diagnostic kits, such as those described above, comprising at least one probe which can be conveniently used, e.g., to determine whether a subject has or is at risk of developing disease such as AKI, CKD, ESRD and/or renal cell carcinoma (RCC), in particular clear cell renal cell carcinoma.

The term "protein-binding molecule" or "antibody-based binding moiety" or "antibody" includes immunoglobulin molecules and immunologically active determinants of immunoglobulin molecules, e.g., molecules that contain an antigen binding site which specifically binds (i.e. immunoreacts with) to the Psap proteins. The term "antibody-based binding moiety" is intended to include whole antibodies, e.g., of any isotype (IgG, IgA, IgM, IgE, etc), and includes fragments thereof which are also specifically reactive with the Psap proteins. Antibodies can be fragmented using conventional techniques. Thus, the term includes segments of proteolytically-cleaved or recombinantly-prepared portions of an antibody molecule that are capable of selectively reacting with a certain protein. Non limiting examples of such proteolytic and/or recombinant fragments include Fab, F(ab')2, Fab', Fv, dAbs and single chain antibodies (scFv) containing a VL and VH domain joined by a peptide linker. The scFv's can be covalently or non-covalently linked to form antibodies having two or more binding sites. Thus, "antibody-base binding moiety" includes polyclonal, monoclonal, or other purified preparations of antibodies and recombinant antibodies. The term "antibody-base binding moiety" is further intended to include humanized antibodies, bispecific antibodies, and chimeric molecules having at least one antigen binding determinant derived from an antibody molecule. In a preferred embodiment, the antibody-based binding moiety detectably labeled.

The term "labeled antibody", as used herein, includes antibodies that are labeled by a detectable means and include, but are not limited to, antibodies that are enzymatically, radioactively, fluorescently, and chemiluminescently labeled. Antibodies can also be labeled with a detectable tag, such as c-Myc, HA, VSV-G, HSV, FLAG, V5, or HIS. The detection and quantification of Psap or Tsp-1 present in the tissue samples correlate to the intensity of the signal emitted from the detectably labeled antibody.

In one embodiment, the antibody-based binding moiety is detectably labeled by linking the antibody to an enzyme. The enzyme, in turn, when exposed to it's substrate, will react with the substrate in such a manner as to produce a chemical moiety which can be detected, for example, by spectrophotometric, fluorometric or by visual means. Enzymes which can be used to detectably label the antibodies of the present invention include, but are not limited to, malate dehydrogenase, staphylococcal nuclease, delta-V-steroid isomerase, yeast alcohol dehydrogenase, alpha-glycerophosphate dehydrogenase, triose phosphate isomerase, horseradish peroxidase, alkaline phosphatase, asparaginase, glucose oxidase, beta-galactosidase, ribonuclease, urease, catalase, glucose-VI-phosphate dehydrogenase, glucoamylase and acetylcholinesterase.

Detection can also be accomplished using any of a variety of other immunoassays. For example, by radioactively labeling an antibody, it is possible to detect the antibody through the use of radioimmune assays. The radioactive isotope can be detected by such means as the use of a gamma counter or a scintillation counter or by audioradiography. Isotopes which are particularly useful for the purpose of the present invention are $^3$H, $^{131}$I, $^{35}$S, $^{14}$C, and preferably $^{125}$I.

It is also possible to label an antibody with a fluorescent compound. When the fluorescently labeled antibody is exposed to light of the proper wavelength, its presence can then be detected due to fluorescence. Among the most commonly used fluorescent labeling compounds are CYE dyes, fluorescein isothiocyanate, rhodamine, phycoerytherin, phycocyanin, allophycocyanin, o-phthaldehyde and fluorescamine.

An antibody can also be detectably labeled using fluorescence emitting metals such as 152Eu, or others of the lanthanide series. These metals can be attached to the antibody using such metal chelating groups as diethylenetriaminepentaacetic acid (DTPA) or ethylenediaminetetraacetic acid (EDTA).

An antibody also can be detectably labeled by coupling it to a chemiluminescent compound. The presence of the chemiluminescent-antibody is then determined by detecting the presence of luminescence that arises during the course of a chemical reaction. Examples of particularly useful chemiluminescent labeling compounds are luminol, luciferin, isoluminol, theromatic acridinium ester, imidazole, acridinium salt and oxalate ester.

As mentioned above, levels of enzyme protein can be detected by immunoassays, such as enzyme linked immunoabsorbant assay (ELISA), radioimmunoas say (RIA), Immunoradiometric assay (IRMA), Western blotting, immunocytochemistry or immunohistochemistry, each of which are described in more detail below Immunoassays such as ELISA or RIA, which can be extremely rapid, are more generally preferred. Antibody arrays or protein chips can also be employed, see for example U.S. Patent Application Nos: 20030013208A1; 20020155493A1; 20030017515 and U.S. Pat. Nos. 6,329,209; 6,365,418, which are herein incorporated by reference in their entirety.

Immunoassays

The most common enzyme immunoassay is the "Enzyme-Linked Immunosorbent Assay (ELISA)." ELISA is a technique for detecting and measuring the concentration of an antigen using a labeled (e.g. enzyme linked) form of the antibody. There are different forms of ELISA, which are well known to those skilled in the art. The standard techniques known in the art for ELISA are described in "Methods in Immunodiagnosis", 2nd Edition, Rose and Bigazzi, eds. John Wiley & Sons, 1980; Campbell et al., "Methods and Immunology", W. A. Benjamin, Inc., 1964; and Oellerich, M. 1984, J. Clin. Chem. Clin. Biochem., 22:895-904.

In a "sandwich ELISA", an antibody (e.g. anti-enzyme) is linked to a solid phase (i.e. a microtiter plate) and exposed to a biological sample containing antigen (e.g. enzyme). The solid phase is then washed to remove unbound antigen. A labeled antibody (e.g. enzyme linked) is then bound to the bound-antigen (if present) forming an antibody-antigen-antibody sandwich. Examples of enzymes that can be linked to the antibody are alkaline phosphatase, horseradish peroxidase, luciferase, urease, and B-galactosidase. The enzyme linked antibody reacts with a substrate to generate a colored reaction product that can be measured.

In a "competitive ELISA", antibody is incubated with a sample containing antigen (i.e. enzyme). The antigen-antibody mixture is then contacted with a solid phase (e.g. a microtiter plate) that is coated with antigen (i.e., enzyme). The more antigen present in the sample, the less free antibody that will be available to bind to the solid phase. A labeled (e.g., enzyme linked) secondary antibody is then added to the solid phase to determine the amount of primary antibody bound to the solid phase.

In an "immunohistochemistry assay" a section of tissue is tested for specific proteins by exposing the tissue to antibodies that are specific for the protein that is being assayed. The antibodies are then visualized by any of a number of methods to determine the presence and amount of the protein present. Examples of methods used to visualize antibodies are, for example, through enzymes linked to the antibodies (e.g., luciferase, alkaline phosphatase, horseradish peroxidase, or beta-galactosidase), or chemical methods (e.g., DAB/Substrate chromagen). The sample is then analysed microscopically, most preferably by light microscopy of a sample stained with a stain that is detected in the visible spectrum, using any of a variety of such staining methods and reagents known to those skilled in the art.

Alternatively, "Radioimmunoassays" can be employed. A radioimmunoassay is a technique for detecting and measuring the concentration of an antigen using a labeled (e.g. radioactively or fluorescently labeled) form of the antigen. Examples of radioactive labels for antigens include 3H, 14C, and 1251. The concentration of antigen enzyme in a biological sample is measured by having the antigen in the biological sample compete with the labeled (e.g. radioactively) antigen for binding to an antibody to the antigen. To ensure competitive binding between the labeled antigen and the unlabeled antigen, the labeled antigen is present in a concentration sufficient to saturate the binding sites of the antibody. The higher the concentration of antigen in the sample, the lower the concentration of labeled antigen that will bind to the antibody.

In a radioimmunoassay, to determine the concentration of labeled antigen bound to antibody, the antigen-antibody complex must be separated from the free antigen. One method for separating the antigen-antibody complex from the free antigen is by precipitating the antigen-antibody complex with an anti-isotype antiserum. Another method for separating the antigen-antibody complex from the free antigen is by precipitating the antigen-antibody complex with formalin-killed S. aureus. Yet another method for separating the antigen-antibody complex from the free antigen is by performing a "solid-phase radioimmunoas say" where the antibody is linked (e.g., covalently) to Sepharose beads, polystyrene wells, polyvinylchloride wells, or microtiter wells. By comparing the concentration of labeled antigen bound to antibody to a standard curve based on samples having a known concentration of antigen, the concentration of antigen in the biological sample can be determined.

An "immunoradiometric assay" (IRMA) is an immunoassay in which the antibody reagent is radioactively labeled. An IRMA requires the production of a multivalent antigen conjugate, by techniques such as conjugation to a protein e.g., rabbit serum albumin (RSA). The multivalent antigen conjugate must have at least 2 antigen residues per molecule and the antigen residues must be of sufficient distance apart to allow binding by at least two antibodies to the antigen. For example, in an IRMA the multivalent antigen conjugate can be attached to a solid surface such as a plastic sphere. Unlabeled "sample" antigen and antibody to antigen which is radioactively labeled are added to a test tube containing the multivalent antigen conjugate coated sphere. The antigen in the sample competes with the multivalent antigen conjugate for antigen antibody binding sites. After an appropriate incubation period, the unbound reactants are removed by washing and the amount of radioactivity on the solid phase is determined. The amount of bound radioactive antibody is inversely proportional to the concentration of antigen in the sample.

Other techniques can be used to detect the KIM-1 polypeptide in a blood sample 1 sample according to a practitioner's preference, and based upon the present disclosure and the type of biological sample (i.e. plasma, urine, tissue sample etc). One such technique is Western blotting (Towbin et al., Proc. Nat. Acad. Sci. 76:4350 (1979)), wherein a suitably treated sample is run on an SDS-PAGE gel before being transferred to a solid support, such as a nitrocellulose filter. Detectably labeled anti-enzyme antibodies can then be used to assess enzyme levels, where the intensity of the signal from the detectable label corresponds to the amount of enzyme present. Levels can be quantified, for example by densitometry.

In other embodiments, the levels of KIM-1 polypeptide present in a blood sample (e.g., whole blood, plasma or serum etc) can be determined by mass spectrometry such as MALDI/TOF (time-of-flight), SELDI/TOF, liquid chromatography-mass spectrometry (LC-MS), gas chromatography-mass spectrometry (GC-MS), high performance liquid chromatography-mass spectrometry (HPLC-MS), capillary electrophoresis-mass spectrometry, nuclear magnetic resonance spectrometry, or tandem mass spectrometry (e.g., MS/MS, MS/MS/MS, ESI-MS/MS, etc.). See for example, U.S. Patent Application Nos: 20030199001, 20030134304, 20030077616, which are herein incorporated by reference in their entirety.

The terms "mass spectrometry" or "MS" as used herein refer to methods of filtering, detecting, and measuring ions based on their mass-to-charge ratio, or "m/z." In general, one or more molecules of interest are ionized, and the ions are subsequently introduced into a mass spectrographic instrument where, due to a combination of magnetic and electric fields, the ions follow a path in space that is dependent upon mass ("m") and charge ("z"). See, e.g., U.S. Pat. No. 6,204,500, entitled "Mass Spectrometry From Surfaces;" U.S. Pat. No. 6,107,623, entitled "Methods and Apparatus for Tandem Mass Spectrometry;" U.S. Pat. No. 6,268,144, entitled "DNA Diagnostics Based On Mass Spectrometry;" U.S. Pat. No. 6,124,137, entitled "Surface-Enhanced Photolabile Attachment And Release For Desorption And Detection Of Analytes;" Wright et al., "Proteinchip surface enhanced laser desorption/ionization (SELDI) mass spectrometry: a novel protein biochip technology for detection of prostate cancer biomarkers in complex protein mixtures," Prostate Cancer and Prostatic Diseases 2: 264-76

(1999); and Merchant and Weinberger, "Recent advancements in surface-enhanced laser desorption/ionization-time of flight-mass spectrometry," Electrophoresis 21: 1164-67 (2000), each of which is hereby incorporated by reference in its entirety, including all tables, figures, and claims. Mass spectrometry methods are well known in the art and have been used to quantify and/or identify biomolecules, such as proteins and hormones (see, e.g., Li et al., (2000), Tibtech. 18:151-160; Starcevic et. al., (2003), J. Chromatography B, 792: 197-204; Kushnir M M et. al. (2006), Clin. Chem. 52:120-128; Rowley et al. (2000), Methods 20: 383-397; and Kuster and Mann (1998), Curr. Opin. Structural Biol. 8: 393-400). Further, mass spectrometric techniques have been developed that permit at least partial de novo sequencing of isolated proteins. Chait et al., (1993), Science, 262:89-92; Keough et al., (1999), Proc. Natl. Acad. Sci. USA. 96:7131-6; reviewed in Bergman (2000), EXS 88:133-44. Various methods of ionization are known in the art. For examples, Atmospheric Pressure Chemical Ionisation (APCI) Chemical Ionisation (CI) Electron Impact (EI) Electrospray Ionisation (ESI) Fast Atom Bombardment (FAB) Field Desorption/Field Ionisation (FD/FI) Matrix Assisted Laser Desorption Ionisation (MALDI) and Thermospray Ionisation (TSP) In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait). In SELDI, the substrate surface is modified so that it is an active participant in the desorption process. In one variant, the surface is derivatized with adsorbent and/or capture reagents that selectively bind the biomarker of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material. For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094. Detection and quantification of the biomarker will typically depend on the detection of signal intensity. For example, in certain embodiments, the signal strength of peak values from spectra of a first sample and a second sample can be compared (e.g., visually, by computer analysis etc.), to determine the relative amounts of particular biomarker. Software programs such as the Biomarker Wizard program (Ciphergen Biosystems, Inc., Fremont, Calif.) can be used to aid in analyzing mass spectra. The mass spectrometers and their techniques are well known to those of skill in the art. The various assays are described herein in terms of the detection of KIM-1 polypeptide levels in the blood. It is understood that the assays can be readily adapted to detect other analytes as needed e.g., for various other embodiments and or to detect protein levels and depending on the sample type, such as whole blood, plasma or serum.

Mass spectrometry methods are well known in the art and have been used to quantify and/or identify biomolecules, such as proteins (see, e.g., Li et al. (2000) Tibtech 18:151-160; Rowley et al. (2000) Methods 20: 383-397; and Kuster and Mann (1998) Curr. Opin. Structural Biol. 8: 393-400). Further, mass spectrometric techniques have been developed that permit at least partial de novo sequencing of isolated proteins. Chait et al., Science 262:89-92 (1993); Keough et al., Proc. Natl. Acad. Sci. USA. 96:7131-6 (1999); reviewed in Bergman, EXS 88:133-44 (2000).

In certain embodiments, a gas phase ion spectrophotometer is used. In other embodiments, laser-desorption/ionization mass spectrometry is used to analyze the sample. Modern laser desorption/ionization mass spectrometry ("LDI-MS") can be practiced in two main variations: matrix assisted laser desorption/ionization ("MALDI") mass spectrometry and surface-enhanced laser desorption/ionization ("SELDI"). In MALDI, the analyte is mixed with a solution containing a matrix, and a drop of the liquid is placed on the surface of a substrate. The matrix solution then co-crystallizes with the biological molecules. The substrate is inserted into the mass spectrometer. Laser energy is directed to the substrate surface where it desorbs and ionizes the biological molecules without significantly fragmenting them. See, e.g., U.S. Pat. No. 5,118,937 (Hillenkamp et al.), and U.S. Pat. No. 5,045,694 (Beavis & Chait).

In SELDI, the substrate surface is modified so that it is an active participant in the desorption process. In one variant, the surface is derivatized with adsorbent and/or capture reagents that selectively bind the protein of interest. In another variant, the surface is derivatized with energy absorbing molecules that are not desorbed when struck with the laser. In another variant, the surface is derivatized with molecules that bind the protein of interest and that contain a photolytic bond that is broken upon application of the laser. In each of these methods, the derivatizing agent generally is localized to a specific location on the substrate surface where the sample is applied. See, e.g., U.S. Pat. No. 5,719,060 and WO 98/59361. The two methods can be combined by, for example, using a SELDI affinity surface to capture an analyte and adding matrix-containing liquid to the captured analyte to provide the energy absorbing material.

For additional information regarding mass spectrometers, see, e.g., Principles of Instrumental Analysis, 3rd edition., Skoog, Saunders College Publishing, Philadelphia, 1985; and Kirk-Othmer Encyclopedia of Chemical Technology, 4.sup.th ed. Vol. 15 (John Wiley & Sons, New York 1995), pp. 1071-1094.

Detection of the presence of the KIM-1 polypeptide in a blood sample will typically depend on the detection of signal intensity. This, in turn, can reflect the quantity and character of a polypeptide bound to the substrate. For example, in certain embodiments, the signal strength of peak values from spectra of a first sample and a second sample can be compared (e.g., visually, by computer analysis etc.), to determine the relative amounts of particular biomolecules. Software programs such as the Biomarker Wizard program (Ciphergen Biosystems, Inc., Fremont, Calif.) can be used to aid in analyzing mass spectra. The mass spectrometers and their techniques are well known to those of skill in the art.

Methods of Optimizing Treatments for Subjects Identified to have Acute Kidney Injury Other aspects of the present invention relate to a method of monitoring the progression of a kidney injury in a subject, and/or alternatively, monitoring the progress of a treatment (e.g., treatment for kidney disease and/or kidney injury) in a subject, by determining blood levels of KIM-1 in a subject at multiple timepoints, e.g., a first time point and a second, and/or $3^{rd}$, and/or $4^{th}$, and/or $5^{th}$ or more timepoints.

Other aspects of the invention provide methods for improving the efficacy of treatment for acute kidney injury, by determining the levels or concentrations of KIM-1 polypeptide.

One aspect of the present invention provides for a method for monitoring progression of kidney injury in a subject with a level of KIM-1 polypeptide in the blood at least 4-fold higher than a reference blood KIM-1 polypeptide level, comprising: (a) measuring, at a first timepoint, a first level of KIM-1 polypeptide in a first blood sample obtained from the subject; (b) measuring, at a second timepoint, a second level of KIM-1 polypeptide in a second blood sample obtained from the subject; wherein the second timepoint is later than the first timepoint; (c) comparing the level of the KIM-1 polypeptide in the first blood sample with the level of the KIM-1 polypeptide in the first blood sample; and (d) identifying the subject as (a) having a more severe kidney injury at the second timepoint as compared to the first timepoint, where the level of KIM-1 polypeptide in the blood sample obtained at the second timepoint is above the level of KIM-1 polypeptide in the blood sample obtained at the first timepoint; or (b) having a less severe kidney at the second timepoint as compared to the first timepoint where the level of KIM-1 polypeptide in the blood sample obtained at the second timepoint is below the level of KIM-1 polypeptide in the blood sample obtained at the first timepoint. In some embodiments, the subject can be admininstered an appropriate treatment for kidney disease where the subject is identified to have a more severe kidney injury at the second or subsequent timepoint.

In some embodiments, aspects of the invention relate to a method for monitoring treatment progress in a subject with kidney injury, the method comprising: (a) measuring, at a first timepoint, a first level of KIM-1 polypeptide in a first blood sample obtained from the subject; (b) administering to the subject an appropriate therapeutic agent for treating kidney injury; and (c) measuring, at a second timepoint, a second level of KIM-1 polypeptide in a second blood sample obtained from the subject; wherein the second timepoint is later than the first timepoint and after said administering; and wherein if the second level of KIM-1 polypeptide is significantly lower than the first level, then the treatment is considered effective.

Another aspect of the present invention relates to a method for treating a subject with kidney disease comprising administering an appropriate therapy for kidney disease to the subject determined to have a level of KIM-1 polypeptide in the blood at least 4-fold above a reference blood KIM-1 polypeptide level.

In another embodiment of this aspect, the method comprises contacting a blood sample (e.g., whole blood sample, plasma sample, serum sample etc.) obtained from a subject with at least one agent that specifically binds to KIM-1 polypeptide; (b) measuring the level or concentration of the KIM-1 polypeptide using an assay specific for the at least one agent; and (c) comparing the level or concentration of the KIM-1 polypeptide with a reference level or concentration of KIM-1 polypeptide, wherein if the level of KIM-1 polypeptide in the blood sample is at least 4-fold higher than the reference level or concentration of KIM-1 polypeptide it indicates a need to administer to the subject a therapeutic treatment for acute kidney injury.

In another embodiment of this aspect, a method for monitoring treatment efficacy of a subject with acute kidney injury is provided, the method comprising: (a) determining, from a blood sample obtained from a subject at a first time point, a level or concentration of kidney injury molecule-1 (KIM-1); (b) determining a level or concentration of KIM-1 polypeptide in the blood sample obtained from said subject at a second time point; and (c) comparing the level or concentration of the KIM-1 polypeptide the second time point to the level or concentration of the KIM-1 polypeptide at the first time point, wherein a decrease in the level or concentration of the KIM-1 polypeptide at the second time point indicates the treatment is efficacious for said subject, and wherein the level of KIM-1 polypeptide has stayed the same, or an increase in the level or concentration of KIM-1 polypeptide at the second time point indicates the treatment is not efficacious for said subject.

In some embodiments, a method for monitoring treatment efficacy of a subject is performed on a blood sample which is obtained from a subject who has a blood KIM-1 polypeptide level of at least 4-fold higher than a reference KIM-1 blood polypeptide level.

Appropriate Therapy for the Treatment of Kidney Disease or Kidney Injury

In some embodiments, the methods and assays further comprise providing an appropriate treatment to the subject for kidney injury, e.g., where the subject is identified to have a blood level of KIM-1 polypeptide at, or above 4-fold a reference KIM-1 level. The management of acute kidney injury hinges, in part, on identification and treatment of the underlying cause. In addition to treatment of the underlying disorder, management of acute kidney injury can include the avoidance of substances that are toxic to the kidneys, or "nephrotoxins," which include, but are not limited to, non-steroidal anti inflammatory drugs (NSAIDs), such as ibuprofen, iodinated contrasts, such as those used for CT scans, and others. Therefore, in some embodiments, an appropriate treatment for kidney injury or disease is to avoid nephrotoxins, including the subject reducing or stopping alcohol consumption and administration of drugs e.g., NSAIDS and/or other non-necessary pharmaceutical compounds.

The choice of a specific therapeutic treatment for acute kidney injury is dependent, in part, on the cause of the acute renal injury, i.e., whether the cause of the acute kidney injury is pre-renal, renal instrinsic, or post-renal. For example, in pre-renal acute kidney injury in the absence of fluid overload, administration of intravenous fluids is typically the first step to improve renal function. Fluid administration may be monitored, for example, with the use of a central venous catheter to avoid over- or under-replacement of fluid. In situations where low blood pressure is a persistent problem in the fluid replete patient, inotropes, such as norepinephrine and dobutamine, may be given to improve cardiac output and hence renal perfusion. In some embodiments, dopamine may be administered. In cases of prerenal acute kidney injury induced by toxins, discontinuation of the offending agent, such as aminoglycoside, penicillin, NSAIDs, or acetaminophen, can be an effective treatment. If the cause of acute kidney injury is obstruction of the urinary tract, relief of the obstruction (with a nephrostomy or urinary catheter) may be necessary.

In cases where the acute kidney injury has renal intrinsic causes, specific therapies and treatment regimens are administered based on the nature of the renal intrinsic cause. For example, intrinsic acute kidney injury due to Wegener's granulomatosis may respond to steroid medication.

Renal replacement therapy, such as hemodialysis or continuous venovenous hemofiltration (CVVH), may be instituted in some cases of acute kidney injury. Metabolic acidosis and hyperkalemia, the two most serious biochemical manifestations of acute renal failure, may require medical treatment with sodium bicarbonate administration and antihyperkalemic measures, unless dialysis is required.

In some cases of acute kidney injury, lack of improvement after treatment with fluid resuscitation, therapy-resistant hyperkalemia, metabolic acidosis, or fluid overload may necessitate artificial support in the form of dialysis or hemofiltration.

Accordingly, in some embodiments, an appropriate treatment for kidney injury or disease is any of, or a combination of; intravenous fluid administration (e.g. fluid resuscitation or fluid overload), hyperkalemia, metabolic acidosis, administration of inotropes (e.g., norepinephrine and dobutamine), administration of dopamine, discontinuation of an offending agent, e.g., aminoglycoside, penicillin, NSAIDs, or acetaminophen and/or alcohol, dialysis, administration of steroids, hemodialysis or continuous venovenous hemofiltration (CVVH), administration of sodium bicarbonate administration, and/or antihyperkalemic measures.

In some cases of acute kidney injury, in which end-stage renal failure has occurred, an appropriate treatment involves a kidney transplant. As defined herein, a "kidney transplant" or "renal transplant" is the organ transplant of a kidney into a patient with end-stage renal disease. Kidney transplantation is typically classified as deceased-donor (formerly known as cadaveric) or living-donor transplantation depending on the source of the recipient organ. Living-donor renal transplants are further characterized as genetically related (living-related) or non-related (living-unrelated) transplants, depending on whether a biological relationship exists between the donor and recipient.

In some embodiments, an appropriate treatment for kidney injury can comprise administration of a treatment to the subject, e.g., alone or as part of a combinatorial therapy. For example, TGF-β inhibitors can be administered to hamper the progression of kidney fibrosis. Non-limiting examples of agents and/or therapies which can be used to treat chronic kidney disease, end-stage renal disease, or diabetic nephropathy include any, or any combination of angiotensin converting enzyme inhibitors (ACEIs), angiotensin II receptor antagonists (ARBs), bardoxolone methyl, olmesartan medoxomil, sulodexide, avosentan, and renal replacement therapy.

The efficacy of a given treatment for acute kidney injury can be determined by the skilled clinician, for example, using the criteria discussed herein. However, a treatment is considered "effective treatment," as the term is used herein, if any one or all of the signs or symptoms of acute kidney injury, such as in one example, urine creatinine levels, are altered in a beneficial manner, other clinically accepted symptoms or markers of disease are improved, or even ameliorated, e.g., by at least 10% following treatment. Efficacy can also be measured by a failure of an individual to worsen as assessed by hospitalization or need for medical interventions (i.e., progression of the disease is halted or at least slowed). Methods of measuring these indicators are known to those of skill in the art and/or are described herein. Treatment includes any treatment of a acute kidney injury disease in an individual or an animal (some non-limiting examples include a human, or a mammal) and includes: (1) inhibiting the disease, e.g., arresting, or slowing the progression of acute kidney injury or acute kidney injury complications; or (2) relieving the disease, e.g., causing regression of symptoms, e.g., normalizing or reducing urine creatinine levels; and (3) preventing or reducing the likelihood of the development of a further acute kidney injury complication, or the need for administration of a further treatment, such as for example, a renal transplant.

An effective amount for the treatment of a disease means that amount which, when administered to a mammal in need thereof, is sufficient to result in effective treatment as that term is defined herein, for that disease.

Appropriate Therapy for the Treatment of Subjects with RCC

In some embodiments, the methods and assays further comprise providing an appropriate treatment to the subject for treatment of RCC, e.g., where the subject is identified to have a blood level of KIM-1 polypeptide at, or above 4-fold a reference KIM-1 level.

The invention further provides methods of treating subjects identified, using the methods of the present invention, to be at risk of developing or afflicted with RCC, wherein where the subject is identified to have a blood level of KIM-1 polypeptide at, or above 4-fold a reference KIM-1 level.

Accordingly, one aspect of the invention also provides a method for selecting a therapeutic regimen or determining if a certain therapeutic regimen is more appropriate for a subject identified as having RCC or at increased risk of developing RCC as identified by the methods as disclosed herein. For example, an aggressive anti-cancer therapeutic regime can be persued in which a subject identified with RCC, where the subject is administered a therapeutically effective amount of an anti-cancer agent to treat the RCC. In alternative embodiments, a prophylactic anti-cancer therapeutic regimen can be pursued in a subject identified to have increased likelihood of developing RCC, where the subject is administered a prophylactic dose or maintenance dose of an anti-cancer agent to prevent the development of RCC. In alternative embodiments, a subject can be monitored for RCC using the methods to measure KIM-1 protein in a blood sample obtained from the subject as disclosed herein, and if on a first (i.e. initial) testing the subject is identified as having RCC, the subject can be administered an anti-cancer therapy, and on a second (i.e. follow-up testing), the subject is identified as not having RCC or having decreased levels of KIM-1 polypeptide in the blood as compared to the levels in the first testing, the subject can be administered an anti-cancer therapy at a maintenance dose.

In general, a therapy is considered to "treat" RCC if it provides one or more of the following treatment outcomes: reduce or delay recurrence of the RCC after the initial therapy; increase median survival time or decrease metastases. The method is particularly suited to determining which subjects will be responsive or experience a positive treatment outcome to a chemotherapeutic regimen. In some embodiments, an anti-cancer therapy is, for example but not limited to administration of a chemotherapeutic agents such as fluoropyrimidine drug such as 5-FU or a platinum drug such as oxaliplatin or cisplatin. Alternatively, the chemotherapy includes administration of a topoisomerase inhibitor such as irinotecan. In a yet further embodiment, the therapy comprises administration of an antibody (as broadly defined herein), ligand or small molecule that binds the Epidermal Growth Factor Receptor (EGFR).

In some embodiments, the anti-cancer therapy is a chemotherapeutic agent, radiotherapy etc. Such anti-cancer therapies are disclosed herein, as well as others that are well known by persons of ordinary skill in the art and are encompassed for use in the present invention. In some embodiments the anti-cancer therapy, or cancer prevention strategy is targets the EGF/EGFR pathway, and in other embodiments, the anti-cancer therapy or cancer prevention strategy does not target the EGF/EGFR pathway.

The term "anti-cancer agent" or "anti-cancer drug" is any agent, compound or entity that would be capably of negatively affecting the cancer in the subject, for example killing cancer cells, inducing apoptosis in cancer cells, reducing the growth rate of cancer cells, reducing the number of mestatic cells, reducing tumor size, inhibiting tumor growth, reducing blood supply to a tumor or cancer cells, promoting an immune response against cancer cells or a tumor, preventing or inhibiting the progression of cancer, or increasing the lifespan of the subject with cancer. Anti-cancer therapy includes biological agents (biotherapy), chemotherapy agents, and radiotherapy agents. The combination of chemotherapy with biological therapy is known as biochemotherapy.

Treatment can include prophylaxis, including agents which slow or reduce the risk of RCC in a subject. In other embodiments, the treatments are any means to prevent the proliferation of RCC cancerous cells. In some embodiments, the treatment is an agent which suppresses the EGF-EGFR pathway, for example but not limited to inhibitors and agents of EGFR. Inhibitors of EGFR include, but are not limited to, tyrosine kinase inhibitors such as quinazolines, such as PID 153035, 4-(3-chloroanilino) quinazoline, or CP-358,774, pyridopyrimidines, pyrimidopyrimidines, pyrrolopyrimidines, such as CGP 59326, CGP 60261 and CGP 62706, and pyrazolopyrimidines, 4-(phenylamino)-7H-pyrrolo[2,3-d] pyrimidines (Traxler et al., (1996) J. Med Chem 39:2285-2292), curcumin (diferuloyl methane) (Laxmin arayana, et al., (1995), Carcinogen 16:1741-1745), 4,5-bis(4-fluoroanilino)phthalimide (Buchdunger et al. (1995) Clin. Cancer Res. 1:813-821; Dinney et al. (1997) Clin. Cancer Res. 3:161-168); tyrphostins containing nitrothiophene moieties (Brunton et al. (1996) Anti Cancer Drug Design 11:265-295); the protein kinase inhibitor ZD-1 839 (AstraZeneca); CP-358774 (Pfizer, Inc.); PD-01 83805 (Warner-Lambert), EKB-569 (Torrance et al., Nature Medicine, Vol. 6, No. 9, September 2000, p. 1024), HKI-272 and HKI-357 (Wyeth); or as described in International patent application WO05/018677 (Wyeth); WO99/09016 (American Cyanamid); WO098/43960 (American Cyanamid); WO 98/14451; WO 98/02434; WO97/38983 (Warener Labert); WO99/06378 (Warner Lambert); WO99/06396 (Warner Lambert); WO96/30347 (Pfizer, Inc.); WO96/33978 (Zeneca); WO96/33977 (Zeneca); and WO96/33980 (Zeneca), WO 95/19970; U.S. Pat. App. Nos. 2005/0101618 assigned to Pfizer, 2005/0101617, 20050090500 assigned to OSI Pharmaceuticals, Inc.; all herein incorporated by reference. Further useful EGFR inhibitors are described in U.S. Pat. App. No. 20040127470, particularly in tables 10, 11, and 12, and are herein incorporated by reference.

In another embodiment, the anti-cancer therapy includes a chemotherapeutic regimen further comprises radiation therapy. In an alternate embodiment, the therapy comprises administration of an anti-EGFR antibody or biological equivalent thereof. In some embodiments, the anti cancer treatment comprises the administration of a chemotherapeutic drug selected from the group consisting of fluoropyrimidine (e.g., 5-FU), oxaliplatin, CPT-11, (e.g., irinotecan) a platinum drug or an anti EGFR antibody, such as the cetuximab antibody or a combination of such therapies, alone or in combination with surgical resection of the tumor. In yet a further aspect, the treatment compresses radiation therapy and/or surgical resection of the tumor masses. In one embodiment, the present invention encompasses administering to a subject identified as having, or increased risk of developing RCC an anti-cancer combination therapy where combinations of anti-cancer agents are used, such as for example Taxol, cyclophosphamide, cisplatin, gancyclovir and the like. Anti-cancer therapies are well known in the art and are encompassed for use in the methods of the present invention. Chemotherapy includes, but is not limited to an alkylating agent, mitotic inhibitor, antibiotic, or antimetabolite, anti-angiogenic agents etc. The chemotherapy can comprise administration of CPT-11, temozolomide, or a platin compound. Radiotherapy can include, for example, x-ray irradiation, w-irradiation, .gamma.-irradiation, or microwaves.

The term "chemotherapeutic agent" or "chemotherapy agent" are used interchangeably herein and refers to an agent that can be used in the treatment of cancers and neoplasms, for example brain cancers and gliomas and that is capable of treating such a disorder. In some embodiments, a chemotherapeutic agent can be in the form of a prodrug which can be activated to a cytotoxic form. Chemotherapeutic agents are commonly known by persons of ordinary skill in the art and are encompassed for use in the present invention. For example, chemotherapeutic drugs for the treatment of tumors and gliomas include, but are not limited to: temozolomide (Temodar), procarbazine (Matulane), and lomustine (CCNU). Chemotherapy given intravenously (by IV, via needle inserted into a vein) includes vincristine (Oncovin or Vincasar PFS), cisplatin (Platinol), carmustine (BCNU, BiCNU), and carboplatin (Paraplatin), Mexotrexate (Rheumatrex or Trexall), irinotecan (CPT-11); erlotinib; oxalipatin; anthracyclins-idarubicin and daunorubicin; doxorubicin; alkylating agents such as melphalan and chlorambucil; cisplatinum, methotrexate, and alkaloids such as vindesine and vinblastine.

In another embodiment, the present invention encompasses combination therapy in which subjects identified as having, or increased risk of developing RCC using the methods as disclosed herein are administered an anti-cancer combination therapy where combinations of anti-cancer agents are used are used in combination with cytostatic agents, anti-VEGF and/or p53 reactivation agent. A cytostatic agent is any agent capable of inhibiting or suppressing cellular growth and multiplication. Examples of cytostatic agents used in the treatment of cancer are paclitaxel, 5-fluorouracil, 5-fluorouridine, mitomycin-C, doxorubicin, and zotarolimus. Other cancer therapeutics include inhibitors of matrix metalloproteinases such as marimastat, growth factor antagonists, signal transduction inhibitors and protein kinase C inhibitors.

Some examples of anti-VEGF agents include bevacizumab (Avastin™), VEGF Trap, CP-547,632, AG13736, AG28262, SU5416, SU11248, SU6668, ZD-6474, ZD4190, CEP-7055, PKC 412, AEE788, AZD-2171, sorafenib, vatalanib, pegaptanib octasodium, IM862, DC101, angiozyme, Sirna-027, caplostatin, neovastat, ranibizumab, thalidomide, and AGA-1470, a synthetic analog of fumagillin (alternate names: Amebacilin, Fugillin, Fumadil B, Fumadil) (A. G. Scientific, catalog # F1028), an angio-inhibitory compound secreted by *Aspergillus fumigates*. As used herein the term "anti-VEGF agent" refers to any compound or agent that produces a direct effect on the signaling pathways that promote growth, proliferation and survival of a cell by inhibiting the function of the VEGF protein, including inhibiting the function of VEGF receptor proteins. The term "agent" or "compound" as used herein means any organic or inorganic molecule, including modified and unmodified nucleic acids such as antisense nucleic acids, RNAi agents such as siRNA or shRNA, peptides, peptidomimetics, receptors, ligands, and antibodies. Preferred VEGF inhibitors, include for example, AVASTIN™ (bevacizumab), an anti-VEGF monoclonal antibody of Genentech, Inc. of South San Francisco, Calif., VEGF Trap (Regeneron/Aventis). Additional VEGF inhibitors include CP-547,632 (3-(4-Bromo-2, 6-difluoro-benzyloxy)-5-[3-(4-pyrrolidin 1-yl-butyl)-ureido]-isothiazole-4-carboxylic acid amide hydrochloride; Pfizer Inc., NY), AG13736, AG28262 (Pfizer Inc.), SU5416, SU11248, & SU6668 (formerly Sugen Inc., now Pfizer, New York, N.Y.), ZD-6474 (AstraZeneca), ZD4190 which inhibits VEGF-R2 and -R1 (AstraZeneca), CEP-7055 (Cephalon Inc., Frazer, Pa.), PKC 412 (Novartis), AEE788 (Novartis), AZD-2171), NEXAVAR™ (BAY 43-9006, sorafenib; Bayer Pharmaceuticals and Onyx Pharmaceuticals), vatalanib (also known as PTK-787, ZK-222584: Novartis & Schering: AG), MACUGEN™ (pegaptanib octasodium, NX-1838, EYE-001, Pfizer Inc./Gilead/Eyetech), IM862 (glufanide disodium, Cytran Inc. of Kirkland, Wash., USA), VEGFR2-selective monoclonal antibody DC101 (ImClone Systems, Inc.), angiozyme, a synthetic ribozyme from Ribozyme (Boulder, Colo.) and Chiron (Emeryville, Calif.), Sirna-027 (an siRNA-based VEGFR1 inhibitor, Sirna Therapeutics, San Francisco, Calif.) Caplostatin, soluble ectodomains of the VEGF receptors, Neovastat (AEterna Zentaris Inc; Quebec City, Calif.) and combinations thereof.

The compounds used in connection with the treatment methods of the present invention are administered and dosed in accordance with good medical practice, taking into account the clinical condition of the individual subject, the site and method of administration, scheduling of administration, patient age, sex, body weight and other factors known to medical practitioners. The pharmaceutically "effective amount" for purposes herein is thus determined by such considerations as are known in the art. The amount must be effective to achieve improvement including, but not limited to, improved survival rate or more rapid recovery, or improvement or elimination of symptoms and other indicators as are selected as appropriate measures by those skilled in the art.

The methods of the present invention are useful for the early detection of subjects susceptible to developing RCC. Thus, treatment may be initiated early, e.g. before or at the beginning of the onset of symptoms, for example before the onset of RCC, based on the subject having a level of KIM-1 in the blood at least about 4-fold above a reference level for blood KIM-1. In alternative embodiments, the treatment may be administered to a subject that has, or is at risk of developing RCC. In alternative embodiments, the treatment may be administered prior to, during, concurrent or post the development of RCC. The effective amount or dosage required at these early stages will typically be lower than those needed at later stages of disease where the symptoms of RCC are severe. Such dosages are known to those of skill in the art and can be determined by a physician.

In some embodiments, where a subject is identified as having increased risk of having or developing RCC where the subject is identified to have a blood level of KIM-1 polypeptide at, or above 4-fold a reference KIM-1 level, a clinician can recommended a treatment regimen to reduce or lower the expression levels of the RCC biomarkers in the subject.

In another embodiment, the levels of KIM-1 protein in the blood can be measured in a subject with RCC before, during and after a anti-cancer therapy or treatment regimen, and where if there is no decrease in blood KIM-1 levels in the subject after a period of time of being administered such a treatment regimen, then the treatment regimen could be modified, for example the subject could be administered (i) a different anti-cancer therapy or anti-cancer drug (ii) a different amount such as in increased amount or dose of a anti-cancer therapy or anti-cancer drug or (iii) a combination of anti-cancer therapies etc.

Selection of Blood Samples for Processing in the Assays and Methods

In all aspects of the invention, the assays, kits and methods, e.g., methods for monitoring progression of kidney injury in a subject, or methods for monitoring the effectiveness of a treatment (e.g., method to monitor treatment progress) is performed on a blood sample obtained from a subject who is suspected to have, or has been previously diagnosed with or identified as suffering from or having a kidney injury, e.g., AKI, or injury to the proximal tubule of the kidney. In some embodiments, the method is performed on a blood sample obtained from a subject diagnosed with, or suspected to have a condition in need of treatment (e.g. acute kidney injury, chronic kidney disease, end-stage renal disease, or diabetic nephropathy) or one or more complications related to such a condition, or optionally, having undergone, or to undergo a cardiopulmonary bypass (CBP), or have already undergone treatment for such a condition. The subject can also be one who is at risk of developing a condition associated with kidney fibrosis. For example, acute kidney injury is now appreciated to be significantly associated with increased risk of future chronic kidney disease and end-stage renal disease.

In some embodiments, the blood sample used in the assays, methods and kits as disclosed herein is from a subject selected to be assessed, where the subject has been identified to suffer from an insult or injury to the kidney, e.g., an injury to the proximal tube of the kidney.

In some embodiments, the blood sample used in the assays, methods and kits as disclosed herein is from a subject selected to be assessed, where the subject has been identified to suffer from acute kidney injury, and the methods described herein are used to treat the subject from developing chronic kidney disease. In some embodiments, the method as used herein are used to prevent the worsening of a symptom of AKI, and/or monitoring the progression of AKI.

In some embodiments, the blood sample used in the assays, methods and kits as disclosed herein is from a subject selected to be assessed, where the subject has been identified to suffer from chronic kidney disease or after a cardiopulmonary bypass (CBP) operation, and the methods described herein are used to prevent the subject from progressing to end-stage renal disease.

Common symptoms of chronic kidney disease include tiredness, nausea, urine-like odor to the breath, bone pain, abnormally dark or light skin, itching, restless leg syndrome, blood in stools, bruising easily, pedal edema, and peripheral edema. Chronic kidney disease can be diagnosed through, e.g., medical history, a blood test that measures complete blood count, BUN level, or creatinine level, renal flow and scan, and renal ultrasound.

In some embodiments, the blood sample used in the assays, methods and kits as disclosed herein is from a subject selected to be assessed, where the subject has been identified to have diabetes, e.g., type 1 diabetes. In some embodiments, the methods described herein are used to monitor the kidney injury in such a subject, and to monitor and optionally treat the subject prevent the subject from progressing to end-stage renal disease.

When the kidneys are clearly beginning to shut down, it is called end stage renal disease. Symptoms of end-stage renal disease include, but are not limited to, a decrease in urine output, inability to urinate, fatigue, headaches, unexplained weight loss, loss of appetite, nausea and vomiting, dry skin and itching, changes in skin color, bone pain, confusion and difficulty concentrating, bruising easily, numbness in hands and feet, bad breath, excessive thirst, and frequent hiccups. End-stage renal disease can be diagnosed through, e.g., a physical examination and blood tests to check kidney function.

In some embodiments, the blood sample used in the assays, methods and kits as disclosed herein is from a subject selected to be assessed, where the subject has been identified to have diabetic neuropathy. Symptoms of diabetic nephropathy include, but are not limited to, lomerular hypertrophy, basement membrane thickening, and mesangial expansion. Diabetic nephropathy can be diagnosed and/or monitored using blood or urine tests, as well as by kidney biopsy. Such tests may be used to monitor improvement of symptoms during or following treatment. By way of example, diabetic nephropathy can be diagnosedand/or assessed by evaluating blood and/or protein content in the urine. Diabetic nephropathy can also be diagnosed and/or assessed by evaluating creatinine and/or urea level in blood, and/or by estimates of glomerular filtration rate based on creatinine score.

In some embodiments, the blood sample used in the assays, methods and kits as disclosed herein is from a subject selected to be assessed, where the subject has been identified to have kidney fibrosis or is at risk of developing kidney fibrosis. For example, the risk of developing kidney fibrosis is increased if the kidney suffers from an injury or insult. A condition associated with kidney fibrosis can be diagnosed by a blood test that measures the level of waste products such as creatinine and urea, a urine test that looks for abnormalities, an imaging test using ultrasound to assess kidney's structure and size, or a kidney biopsy.

The present invention can further be defined in any of the following numbered paragraphs:

1. An assay comprising: (i) measuring in a blood sample obtained from a subject, a level of KIM-1 polypeptide; (ii) comparing the level of the KIM-1 polypeptide in the blood sample with a reference blood level of KIM-1 polypeptide; and (iii) identifying the subject as (a) having a kidney injury if the level of KIM-1 polypeptide is higher by a statistically significant amount than reference level; or (b) not having a kidney injury if the level of KIM-1 polypeptide not higher by a statistically significant amount than the reference level.
2. The assay of paragraph 1, comprising identifying the subject as (a) having a kidney injury if the level of KIM-1 polypeptide is at least 4-fold above than reference level; or (b) not having a kidney injury if the level of KIM-1 polypeptide less than 4-fold above the reference level.
3. The assay of paragraph 2, the assay further comprises selecting the subject for an appropriate treatment for kidney disease.
4. The assay of paragraph 3, wherein when the level of KIM-1 polypeptide is at least 4-fold above the reference level, the assay further comprises providing a treatment appropriate for treating kidney disease. 5. The assay of any of paragraphs 1 to 4, wherein the kidney injury is injury to the proximal tubule of the kidney or acute kidney injury (AKI)
6. The assay of any of paragraphs 1 to 5, wherein the kidney injury is chronic kidney disease (CKD) or where the kidney injury is early kidney injury which will progress into chronic kidney disease (CKD).
7. The assay of any of paragraphs 1 to 5, wherein the blood sample is obtained from a subject suspected to have a kidney disease or who has undergone a cardiopulmonary bypass (CBP).
8. The assay of paragraph 1, wherein the blood sample is obtained from a subject who has type-1 diabetes or from a subject who has diabetic nephropathy.
9. The assay of paragraph 8, wherein when the level of KIM-1 polypeptide is at least 5-fold above the reference level, the assay further comprises identifying the subject (c) at risk of developing end stage renal disease (ESRD) within 10 years; or (d) not at risk of developing end stage renal disease (ESRD).
10. An assay comprising: (i) measuring in a blood sample obtained from a subject, a level of KIM-1 polypeptide; (ii) comparing the level of the KIM-1 polypeptide in the blood sample with a reference blood level of KIM-1 polypeptide; and (iii) identifying the subject as (a) having renal cell carcinoma (RCC) if the level of KIM-1 polypeptide is higher by a statistically significant amount than a reference level; or (b) not having RCC if the level of KIM-1 polypeptide is not higher by a statistically significant amount than the reference level.
11. The assay of paragraph 10, comprising identifying the subject as (a) having a kidney injury if the level of KIM-1 polypeptide is at least 4-fold above than reference level; or (b) not having a kidney injury if the level of KIM-1 polypeptide less than 4-fold above the reference level.
12. An assay for selecting a therapy for a subject with kidney disease or kidney injury, comprising:
   (a) contacting a plasma or blood sample obtained from the subject with at least one agent which specifically binds to the KIM-1 polypeptide, wherein binding of the agent to the KIM-1 polypeptide results in a detectable signal which indicates the level of KIM-1 polypepide; and (b) detecting the level of the detectable signal in the plasma or blood sample which indicates the level of the KIM-1 polypeptide, and (c) selecting a therapy for a subject if the detected level of the KIM-1 polypeptide in the plasma or blood sample is at least 4-fold higher than a threshold plasma KIM-1 polypeptide level.
13. An assay to determine if a subject with diabetes or proteinura has a risk of end stage renal disease (EDRD), comprising:
   (a) contacting a plasma or blood sample obtained from the subject with at least one agent which specifically binds to the KIM-1 polypeptide, wherein binding of the agent to the KIM-1 polypeptide results in a detectable signal which indicates the level of KIM-1 polypepide; and
   (b) detecting the level of the detectable signal in the plasma or blood sample which indicates the level of the KIM-1 polypeptide, and (c) selecting the subject for treatment if the detected level of the KIM-1 polypeptide in the plasma or blood sample is at least 4-fold higher than a threshold plasma KIM-1 polypeptide level.

14. The assay of any of paragraphs 1 to 13, wherein the level of KIM-1 polypeptide is measured using an agent which specifically binds to the KIM-1 polypeptide.

15. The assay of paragraph 14, wherein the agent which specifically binds to the KIM-1 polypeptide is selected from an antibody, antibody fragment, or antigen-binding fragment of an antibody, or a protein-binding molecule.

16. The assay of paragraph 15, wherein the antibody or is a polyclonal antibody, a chimeric antibody, an Fab, fragment, an F(ab')2 fragment, an Fab' fragment, an F sc fragment, or an Fv fragment.

17. The assay of any of paragraphs 1 to 16, wherein the agent which specifically binds to the KIM-1 polypeptide is immobilized on, or attached to, the surface of a solid support.

18. The assay of any of paragraphs 1 to 17, wherein the solid support surface is in the format of a dipstick, a test strip, paper-based assay, a latex bead, a microsphere, or a multi-well plate.

19. The assay of any of paragraphs 1 to 18, wherein the assay is automated or a high-throughput assay.

20. The assay of any of paragraphs 1 to 19, wherein the agent which specifically binds to the KIM-1 polypeptide comprises a detectable label, or wherein the agent can be bound by a secondary agent which comprises a detectable label.

21. The assay of paragraph 20, wherein the detectable label is a fluorescent label.

22. The assay of any of paragraphs 1 to 21, wherein the assay is selected from an immunoassay, mass spectrometry, nuclear magnetic resonance spectrometry, and tandem mass spectrometry HPLC.

23. The assay of paragraph 22, wherein the immunoassay is an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

24. The assay of any of paragraphs 1 to 23, wherein the KIM-1 polypeptide is human KIM-1 polypeptide.

25. The assay of any of paragraphs 1 to 24, wherein the blood sample is any of; a whole blood sample, a plasma sample, a serum sample or a fractionated blood sample.

26. A method for selecting a subject for treatment for kidney disease or kidney injury comprising:
(a) assaying a blood sample obtained from the subject for the level of kidney injury molecule-1 (KIM-1) polypeptide;
(b) selecting the subject for treatment for kidney disease or kidney injury where the level of KIM-1 polypeptide in the plasma or blood sample is at least 4-fold higher than a reference plasma KIM-1 polypeptide level.

27. A method to assess kidney injury over a period of time, comprising:
(a) assaying a plasma or blood sample obtained from the subject at a first timepoint for the level of kidney injury molecule-1 (KIM-1) polypeptide;
(b) assaying a plasma or blood sample obtained from the subject at a second timepoint for the level of kidney injury molecule-1 (KIM-1) polypeptide;
(c) selecting the subject for treatment for kidney disease or kidney injury where the level of KIM-1 polypeptide in the plasma from the second timepoint is increased by a statistically significant amount as compared the level of KIM-1 polypeptide assayed at the first timepoint.

28. The method of any of paragraphs 24-25, wherein assaying a plasma or blood sample for the level of KIM-1 polypeptide comprises contacting the plasma or blood sample with an antibody or antibody fragment that specifically binds to KIM-1 polypeptide and measuring the binding of the antibody to the KIM-1 polypeptide, wherein the binding of the antibody to the KIM-1 polypeptide is indicative of the level of the KIM-1 polypeptide in the plasma or blood sample.

29. The method of paragraph 24, wherein the subject is selected for treatment for kidney disease or kidney injury where the level of KIM-1 polypeptide in the plasma or blood sample is at least between about 4-fold, or 4-fold to 15-fold higher than a reference plasma or blood KIM-1 polypeptide level.

30. The method of paragraph 24, wherein the subject is selected for treatment for kidney disease or kidney injury where the level of KIM-1 polypeptide in the plasma or blood sample is 15-fold higher, or greater than 15-fold higher than a reference plasma KIM-1 polypeptide level.

31. The method of paragraph 24, further comprising administering a treatment to the subject identified as having the level of KIM-1 polypeptide in the plasma sample at least 15-fold above a reference KIM-1 polypeptide level.

32. The method of any of paragraphs 24 to 29, wherein the reference plasma KIM-1 polypeptide level is the level of KIM-1 polypeptide in the plasma obtained from a healthy subject or a subject without acute kidney injury (AKI).

33. A method for monitoring progression of kidney injury in a subject with a level of KIM-1 polypeptide in the blood at least 4-fold higher than a reference blood KIM-1 polypeptide level, the method comprising:
(a) measuring, at a first timepoint, a first level of KIM-1 polypeptide in a first blood sample obtained from the subject;
(b) measuring, at a second timepoint, a second level of KIM-1 polypeptide in a second blood sample obtained from the subject; wherein the second timepoint is later than the first timepoint;
(c) comparing the level of the KIM-1 polypeptide in the first blood sample with the level of the KIM-1 polypeptide in the first blood sample;
(d) identifying the subject as (a) having a more severe kidney injury at the second timepoint as compared to the first timepoint, where the level of KIM-1 polypeptide in the blood sample obtained at the second timepoint is above the level of KIM-1 polypeptide in the blood sample obtained at the first timepoint; or (b) having a less severe kidney at the second timepoint as compared to the first timepoint where the level of KIM-1 polypeptide in the blood sample obtained at the second timepoint is below the level of KIM-1 polypeptide in the blood sample obtained at the first timepoint.

34. The method of paragraph 33, further comprising administering an appropriate treatment for kidney disease where the subject is identified to have a more severe kidney injury at the second timepoint.

35. A method for monitoring treatment progress in a subject with kidney injury, the method comprising:

(a) measuring, at a first timepoint, a first level of KIM-1 polypeptide in a first blood sample obtained from the subject;
(b) administering to the subject an appropriate therapeutic agent for treating kidney injury or RCC; and
(c) measuring, at a second timepoint, a second level of KIM-1 polypeptide in a second blood sample obtained from the subject; wherein the second timepoint is later than the first timepoint and after said administering; and wherein if the second level of KIM-1 polypeptide is significantly lower than the first level, then the treatment is considered effective.

36. The method of paragraph 35, wherein the subject has a level of KIM-1 polypeptide in the blood at least 4-fold higher than a reference blood KIM-1 polypeptide level.

37. A method for treating a subject with kidney disease comprising administering an appropriate therapy for kidney disease to the subject determined to have a level of KIM-1 polypeptide in the blood at least 4-fold above a reference blood KIM-1 polypeptide level.

38. A method for treating a subject with RCC comprising administering an appropriate therapy for RCC to the subject determined to have a level of KIM-1 polypeptide in the blood at least 4-fold above a reference blood KIM-1 polypeptide level.

39. The method of any of paragraphs 26 to 38, wherein the first blood sample and second blood sample is whole blood, plasma, serum or fractionated blood.

40. The method of any of paragraphs 26 to 39, wherein the kidney injury is injury to the proximal tubule of the kidney, acute kidney injury (AKI), kidney disease or chronic kidney disease (CKD).

41. The method of any of paragraphs 26 to 40, wherein the subject is suspected to have a kidney disease or who has undergone a cardiopulmonary bypass (CBP).

42. The method of any of paragraphs 26 to 41, wherein the subject has type-1 diabetes.

43. The method of any of paragraphs 26 to 42, wherein the level of KIM-1 polypeptide is measured using an agent which specifically binds to the KIM-1 polypeptide.

44. The method of paragraph 43, wherein the agent which specifically binds to the KIM-1 polypeptide is selected from an antibody, antibody fragment, or antigen-binding fragment of an antibody, or a protein-binding molecule.

45. The method of paragraph 44, wherein the antibody or is a polyclonal antibody, a chimeric antibody, an Fab, fragment, an F(ab')2 fragment, an Fab' fragment, an F sc fragment, or an Fv fragment.

46. The method of any of paragraphs 26 to 45, wherein the agent which specifically binds to the KIM-1 polypeptide is immobilized on, or attached to, the surface of a solid support.

47. The method of any of paragraphs 26 to 46, wherein the solid support surface is in the format of a dipstick, a test strip, paper-based assay, a latex bead, a microsphere, or a multi-well plate.

48. The method of any of paragraphs 26 to 47, wherein the assay is automated or a high-throughput assay.

49. The method of any of paragraphs 26 to 48, wherein the agent which specifically binds to the KIM-1 polypeptide comprises a detectable label, or wherein the agent can be bound by a secondary agent which comprises a detectable label.

50. The method of paragraph 49, wherein the detectable label is a fluorescent label.

51. The method of any of paragraphs 26 to 50, wherein the assay is selected from an immunoassay, mass spectrometry, nuclear magnetic resonance spectrometry, and tandem mass spectrometry HPLC.

52. The method of paragraph 51, wherein the immunoassay is an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

53. The method of any of paragraphs 26 to 52, wherein the KIM-1 polypeptide is human KIM-1 polypeptide.

54. The method of any of paragraphs 26 to 53, wherein the subject is a mammal

55. The method of any of paragraphs 26 to 54, wherein the subject is a human.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow. Further, to the extent not already indicated, it will be understood by those of ordinary skill in the art that any one of the various embodiments herein described and illustrated can be further modified to incorporate features shown in any of the other embodiments disclosed herein.

All patents and other publications; including literature references, issued patents, published patent applications, and co-pending patent applications; cited throughout this application are expressly incorporated herein by reference for the purpose of describing and disclosing, for example, the methodologies described in such publications that might be used in connection with the technology disclosed herein. These publications are provided solely for their disclosure prior to the filing date of the present application. Nothing in this regard should be construed as an admission that the inventors are not entitled to antedate such disclosure by virtue of prior invention or for any other reason. All statements as to the date or representation as to the contents of these documents is based on the information available to the applicants and does not constitute any admission as to the correctness of the dates or contents of these documents.

The description of embodiments of the disclosure is not intended to be exhaustive or to limit the disclosure to the precise form disclosed. While specific embodiments of, and examples for, the disclosure are disclosed herein for illustrative purposes, various equivalent modifications are possible within the scope of the disclosure, as those skilled in the relevant art will recognize. For example, while method steps or functions are presented in a given order, alternative embodiments may perform functions in a different order, or functions may be performed substantially concurrently. The teachings of the disclosure provided herein can be applied to other procedures or methods as appropriate. The various embodiments disclosed herein can be combined to provide further embodiments. Aspects of the disclosure can be modified, if necessary, to employ the compositions, functions and concepts of the above references and application to provide yet further embodiments of the disclosure.

Specific elements of any of the foregoing embodiments can be combined or substituted for elements in other embodiments. Furthermore, while advantages associated with certain embodiments of the disclosure have been described in the context of these embodiments, other embodiments may also exhibit such advantages, and not all embodiments need necessarily exhibit such advantages to fall within the scope of the disclosure.

The present invention is further illustrated by the following Examples. These Examples are provided to aid in the understanding of the invention and are not construed as a limitation thereof.

EXAMPLES

The following examples illustrate some embodiments and aspects of the invention. It will be apparent to those skilled in the relevant art that various modifications, additions, substitutions, and the like can be performed without altering the spirit or scope of the invention, and such modifications and variations are encompassed within the scope of the invention as defined in the claims which follow. The following examples do not in any way limit the invention.

The technology disclosed herein is further illustrated by the following examples which in no way should be construed as being further limiting.

Materials and Methods

Bilateral Ischemia Reperfusion Injury in Mice

Ischemia was induced in male BALB/c mice using a retroperitoneal approach by clamping both renal pedicles for 10, 20, or 30 minutes and then releasing the clamps according to published techniques from our laboratory.[19] Sham operations were also performed, manipulating the pedicles without induction of ischemia. Twenty-four hours after reperfusion, mice were euthanized, and urine, plasma, and tissue samples were collected and analyzed. In another set of animals, ischemia was induced for 30 minutes; urine and plasma specimens were collected before the surgery and 3, 6, 12, 24, 48, 72, 96, 120, and 144 hours after the reperfusion. The institutional animal care committee approved all animal protocols.

Unilateral Ureteral Obstruction in Mice

Unilateral ureteral obstruction was induced in male BALB/C mice, age 8-10 weeks, as described previously.[20] Mice were anesthetized and the ureter of the left kidney was ligated with 6-0 silk at two points proximal to the kidney. In sham animals, flank incisions were made and the kidney exposed, but the ureter was not tied.

Liver Injury in Mice

As controls, male BALB/c mice were injected intraperitoneally once with 0.5 ml/kg of 10% $CCl_4$ in vegetable oil (n=5) or vegetable oil alone (vehicle, n=5), as previously de-scribed.[21] Forty-eight hours after $CCl_4$ administration, mice were euthanized and urine, plasma, and tissue samples were collected and analyzed.

Gentamicin-Induced Nephrotoxicity

Male Sprague-Dawley rats weighing approximately 230-260 g were administrated 0.9% saline, 50 mg/kg gentamicin, or 200 mg/kg gentamicin intraperitoneally daily for 10 days. Rats were provided with free access to food and water and subjected to a 12-hour light and dark cycle. Rats were euthanized on day 11, and urine, plasma, and tissue samples were collected and analyzed. Tissue samples were fixed in 10% neutral buffered formalin or snap frozen. For histologic assessment, 3- to 5-mm paraffin sections were prepared and stained with hematoxylin and eosin. The rat studies were undertaken in accordance with criteria outlined in a license granted under the Animals (Scientific Procedures) Act 1986 and approved by the University of Liverpool Animal Ethics Committee.

Selection of Patient Study Groups

Single spot urine samples and corresponding plasma samples were obtained from healthy individuals, patients undergoing cardiac surgery, and patients admitted to the surgical intensive care unit. Healthy volunteers (n=48) who are self-reported to be free of chronic inflammatory diseases, chronic infectious diseases, and metabolic disease were participants in the Brigham and Women's Hospital Pheno-Genetic Project, a large-scale tissue bank that provides a sample archive and longitudinal biosampling from its cohort. Cardiac surgery and ICU patients were participants in prospective AKI bio-marker studies conducted at Brigham and Women's Hospital. Urine and plasma samples were obtained in 16 patients post cardiac surgery to serve as a complementary non-AKI cohort and in 28 patients with AKI (15 patients met KDIGO stage 1 criteria and 13 met stage 2 criteria) 22 patients following cardiac surgery and 6 non-cardiac surgery ICU patients. For prospective studies to determine the time course of biomarker changes, we collected plasma and urine samples before surgery; at the end of CPB; and then at 4 hours, 12 hours (urine only), and then daily for 5 days after CPB. The primary outcome variable was development of AKI, defined as a 50% increase in plasma creatinine from baseline within 7 days or a 0.3 mg/dl increase within 2 days according to the KDIGO criteria.[22]

CKD urine and plasma samples were collected from outpatients attending a general nephrology clinic at Brigham and Women's Hospital. Urine and plasma samples were collected at approximately the same time. Plasma samples from patients with CKD were also obtained at University of Liverpool. Diagnoses included glomerular diseases (39.1%), diabetic nephropathy in type 2 diabetes (17.4%), and other causes of CKD (43.4%).

To examine the potential value of plasma concentration of KIM-1 as a predictor of progressive renal decline, we studied a subgroup of patients with type 1 diabetes and proteinuria who were previously included in the Joslin Proteinuria Cohort.[15] Of 423 patients participating in the cohort, a random subgroup of 124 patients with a sufficient amount of baseline serum was selected for the current study. The baseline characteristics of the selected patients are shown in Table 6. These patients were followed for 5-15 years (median follow-up, 10 years). During follow-up they had serial serum creatinine measurements to estimate the rate of renal decline rate of eGFR loss (eGFR slopes) according to methods previously described.[23] All human studies were approved by institutional review boards.

KIM-1 Measurement

Microbead-based assays for rodent and human plasma and serum KIM-1 were developed, and extensive validation of the assays were performed using previously described approaches.[24] Urinary KIM-1 in rodents and humans was measured using microbead based assays as described previously.5,7,25,26 Capture antibodies (MAB 1817 for mouse, AF1750 for human [R&D Systems]), MARKE[25] antibody for rat (developed at Brigham and Women's Hospital) were conjugated with COOH polystyrene beads (Bio-Rad) with an amine coupling kit (Bio-Rad) using N-hydroxysuccinamide-1-ethyl-3-(3-dimethylaminopropyl) carbodiimide chemistry according to the manufacturer's protocol. Approximately 6000 beads in 50 ml of sample diluent buffer (0.1M HEPES, 0.1M NaCl, 0.1% Tween-20, and 1% BSA; pH, 7.4; filter sterilized) were incubated with 30 ml of sample or recombinant KIM-1 protein (1817-TM-050-CF for mice, 1750-TM for humans [R&D systems]), and KIM-FC for rats [developed at Brigham and Women's Hospital]) for 45 minutes. After incubation, beads were washed three times with PBS with Tween and incubated with biotinylated anti-KIM-1 detection antibody (BAF 1817 for mice, BAF 1750 for humans [R&D Systems]) and MARKE-2 for rats

[developed at Brigham and Women's Hospital]) for 30 minutes. Beads were washed again with PBS with Tween and incubated for 15 minutes with the streptavidin-phycoerythrin solution (Invitrogen). The signal from the fluorochrome, which is directly proportional to the amount of antigen bound at the microbead surface, is captured using the Bio-Plex system (Bio-Rad). Data were interpreted using a five parametric logistic regression analysis.

Western Blot Analysis

Plasma and urine specimens from healthy volunteers and patients with AKI and CKD were precleared with protein A agarose beads for 30 minutes (Sigma-Aldrich), and 10 ml of the precleared specimens were analyzed using SDS-PAGE electrophoresis (4%-12% NuPage Gel, Invitrogen), transferred to a nitrocellulose membrane, and probed with goat anti-KIM-1 antibody (AF1750, R&D Systems). The membrane was washed three times with PBS with Tween-20, incubated with horseradish peroxidase-conjugated secondary antibody (Cell Signaling Technology), and developed using a chemiluminescence kit (PerkinElmer).

Statistical Analyses

Scatterplots were used to graphically display log-transformed normalized biomarker levels in the clinical samples. Continuous variables were compared using the Wilcoxon rank-sum test and the Spearman correlation coefficient. Diagnostic performance (i.e., the ability of a biomarker to identify AKI) was assessed by using the ROC curve. The area under the ROC curve (AUC) and 95% CIs were calculated using the nonparametric method of De-Long.[27] The eGFR was calculated using the Modification of Diet in Renal Disease equation. P values <0.05 were considered to represent statistically significant differences. Statistical analyses were performed using MedCalc for Windows, version 12.1.4.0 (MedCalc Software, Mariakerke, Belgium). For animal studies, all results are expressed as mean±SEM. One-way ANOVA and t test were performed on control samples and treated samples to evaluate the difference in these groups. The level of significance was set at P<0.05 in all cases. The statistical methods used to analyze the follow-up data from the Joslin proteinuria cohort have been described previously.[23]

Example 1

Kidney injury molecule-1 (KIM-1), also known as hepatitis A virus cellular re-ceptor 1 and T-cell immunoglobulin mucin[1], is a transmembrane glycoprotein originally discovered using representational difference analysis in an effort to identify molecules that are significantly upregulated after acute ischemic kidney injury.[1] The ectodomain of KIM-1 (approximately 90 kD) is cleaved by matrix metalloproteinases and is present in the urine in rodents and humans after kidney proximal tubular injury.[2,3] Since its discovery, KIM-1 has emerged as a sensitive and specific urinary biomarker of kidney injury in both rodent models and humans.[4-7] Recognizing its importance, the US Food and Drug Administration and the European Medicines Agency qualified KIM-1 as a urinary biomarker in the context of drug-induced nephrotoxicity in rat models and in clinical studies on a case-by-case basis.[8,9]

The inventors assessed herein if KIM-1 is released into the circulation after kidney proximal tubule injury. With injury, tubular cell polarity is lost, such that KIM-1 may be released directly into the interstitium. Further, increased transepithelial permeability after tubular injury leads to backleak of tubular contents into the circulation.[10] Also, altered microvascular permeability is an important contributor to the pathophysiology of kidney injury.[11] The actin cytoskeleton architecture is disrupted in renal microvascular endothelial cells, with loss of cell-cell and cell-matrix adhesion junctions, and endothelial cells are detached from the basement membrane; this facilitates KIM-1 movement into the circulation.[11,12] In the present study, in both rodent and human AKI and mouse and human CKD, we show that increased levels of KIM-1 can be detected in the blood and serve as a bio-marker of kidney injury.

Figure 1B:
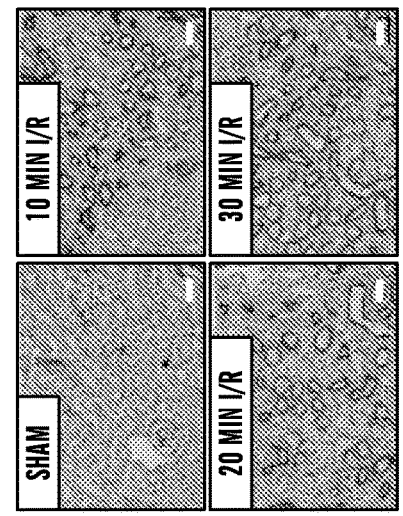
Figure 1C:
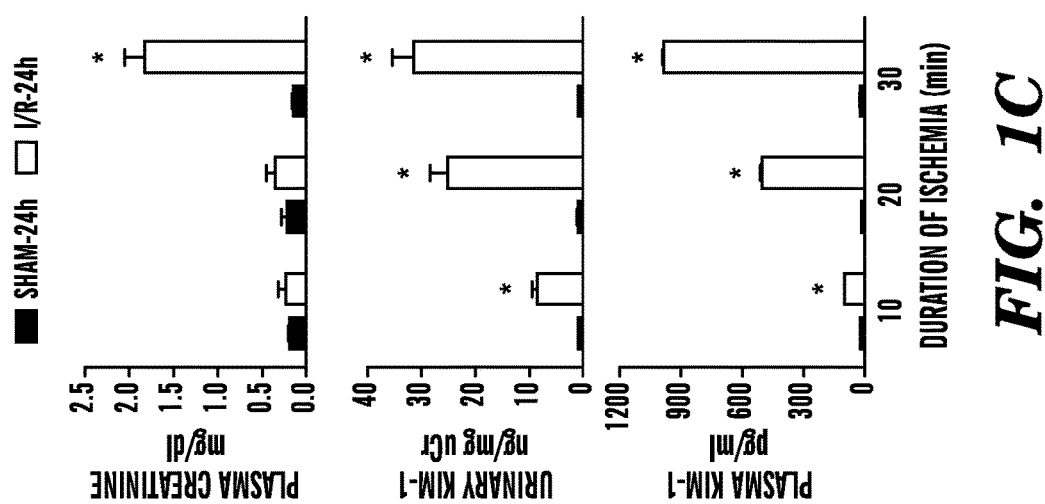

First, the inventors first evaluated whether KIM-1 was elevated in the mouse model of ischemic kidney injury. KIM-1 was quantitated in plasma and urine specimens collected from mice challenged with incremental periods (10, 20, and 30 minutes) of bilateral ischemia, followed by 24 hours of reperfusion. The extent of kidney damage was assessed by histologic analysis and changes in serum creatinine. At 24 hours, after 10 minutes of ischemia, kidney tissues showed focal tubular injury with apoptosis and necrosis, along with brush border loss in the S3 segment of the proximal tubule. These features were more prominent in mice that were subjected to longer periods of ischemia (20 or 30 minutes), where damage included tubular necrosis, intra-tubular casts, and brush border loss (FIG. 1A) Immunohistochemical analysis revealed an increase in KIM-1 protein expression in injured tubular cells, which correlated with increased bilateral ischemic time (FIG. 1B). Plasma creatinine was significantly increased by more than 10-fold in mice subjected to 30 minutes of ischemia/reperfusion but did not significantly change in mice subjected to 10 or 20 minutes ischemia/reperfusion (FIG. 1C). Urinary KIM-1 levels were significantly elevated after 10, 20, or 30 minutes of ischemia by >16-fold (8.5±3.3 ng/mg urinary creati-nine), >48-fold (25.1±10.7 ng/mg urinary creatinine), and >60-fold (31.4±9.5 ng/mg urinary creatinine), respectively, compared with sham-operated mice (0.52±3.3 ng/mg urinary creatinine), consistent with a high sensitivity of urinary KIM-1 levels to detect renal injury in mice (FIG. 1C).[7]

Example 2

KIM-1 Protein Levels in the Blood in Rodent Models of AKI

To measure KIM-1 in serum and plasma specimens, we first established an appropriate assay for rodents and humans. Accurate measurement of blood biomarkers poses several technical challenges because blood contains a high content of potentially interfering proteins and different dynamic ranges of biomarker levels compared with urine. To this end, the inventors have rigorously re-evaluated and validated both rodent and human KIM-1 assays that they had previously developed.[5,7] for the quantitation of serum and plasma KIM-1 levels by characterizing reproducibility, assay range, spike-recovery, interference, and linearity of dilution (Table 3). As shown in FIG. 1C, compared with plasma KIM-1 levels in sham-operated mice (15±2.1 pg/ml), KIM-1 levels were significantly elevated in rodents by >7-fold (112±18 pg/ml), >33-fold (502±17 pg/ml), and >65-fold (987±15 pg/ml) 24 hours after reperfusion and after 10, 20, or 30 minutes of ischemia, respectively.

TABLE 3

Characteristics of microbead-based plasma KIM-1 sandwich ELISA in various species.

| Parameters | Human | Mouse | Rat |
|---|---|---|---|
| Lower limit of quantitation | 4.4 pg/mL | 12.1 pg/mL | 39 ng/mL |
| Assay range | 0.012-50 ng/mL | 0.012-50 ng/mL | 0.039-50 ng/mL |
| Infra assay % CV | <11.45% | <10.15% | <11.4% |
| Inter assay % CV | <12.3% | <9.8% | <13.7% |
| Recovery | 87-115% | 84-110% | 85-125% |
| Linearity | Linear dilutions: 1:8-1:32 | Linear dilutions: 1:4-1:32 | Linear dilutions: 1:5-1:20 |

(CV = coefficient of variation.)

Figure 1D:
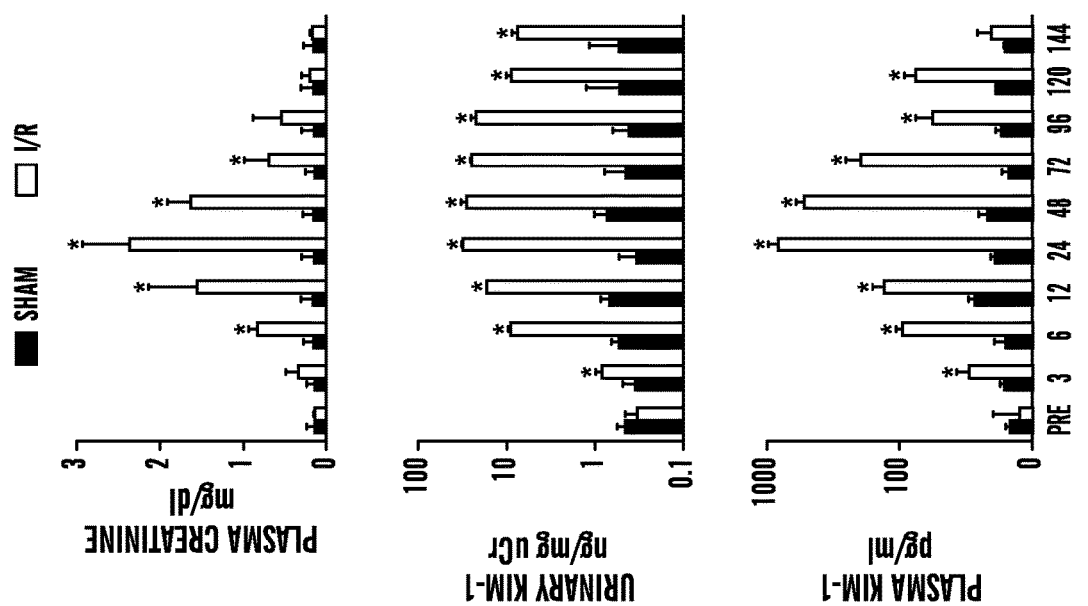

Next the inventors evaluated the sensitivity of plasma KIM-1 in detecting injury at earlier time periods. Mice were challenged with 30 minutes of bilateral ischemia and plasma and urine samples collected 3, 6, 12, 24, 48, 72, 96, 120, and 144 hours after reperfusion. Plasma creatinine levels were increased within 6 hours compared with their preoperative levels or sham-operated mice (FIG. 1D). Urinary KIM-1 and plasma KIM-1 levels were significantly elevated within 3 hours compared with their preoperative levels or 3-hour values in sham-operated mice, and the levels remained elevated at 12, 24, 48, and 96 hours after reperfusion (FIG. 1D).

Figure 1G:
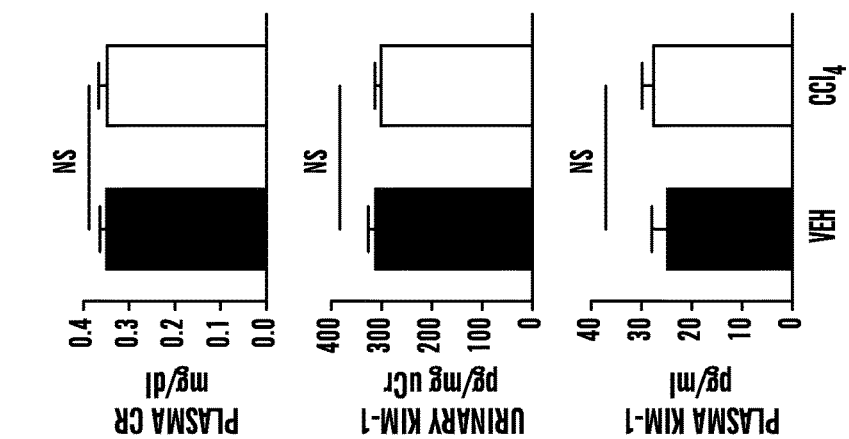
Figure 1F:
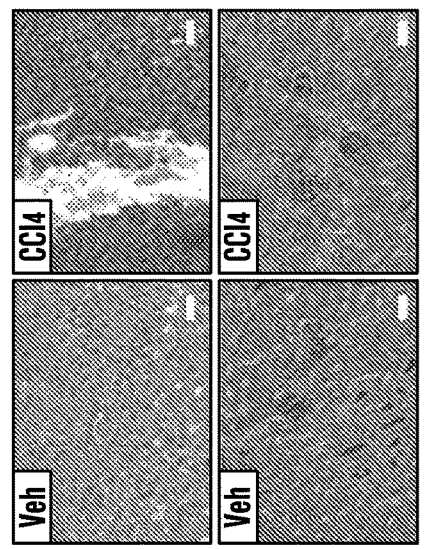
Figure 1H:
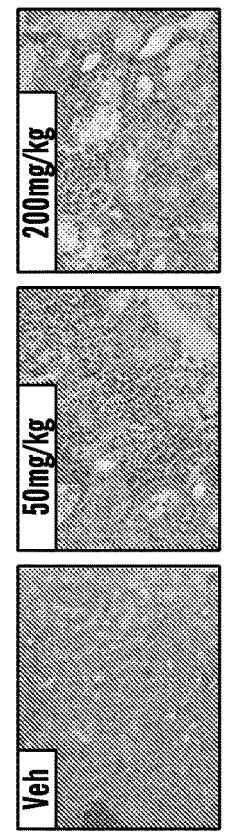
Figure 1E:
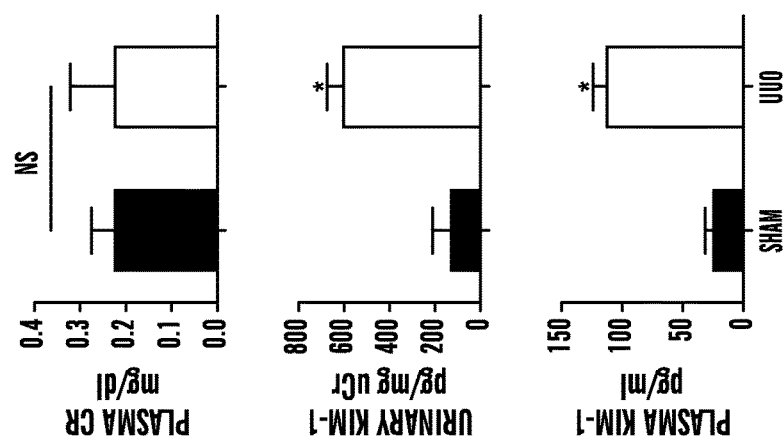
Figure 1I:
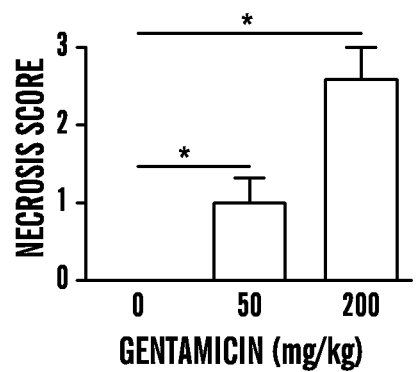

Further, the inventors evaluated the utility of plasma KIM-1 levels in detecting kidney injury in a mouse model of chronic kidney injury. Mice were subjected to unilateral ureteral obstruction and plasma and urine samples were collected on day 7. Plasma and urinary KIM-1 levels increased in these mice but plasma creatinine did not change (FIG. 1E).

To evaluate the specificity of plasma KIM-1 to renal injury, mice were treated with carbon tetrachloride (CCl4), a known hepatotoxicant. A single dose of CCl4 (10% $CCl_4$, 0.5 ml/kg) resulted in liver necrosis, whereas no liver damage was observed in vehicle-treated mice (FIG. 1F, upper panels). No histopathologic changes in kidney morphology (FIG. 1F, lower panels) and no significant alterations in plasma creatinine, urinary KIM-1, or plasma KIM-1 occurred in CCl4-treated mice (FIG. 1G). Thus, plasma KIM-1 was not affected by liver injury.

Figure 1J:
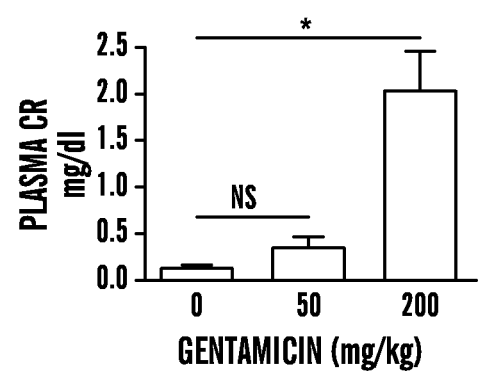
Figure 1K:
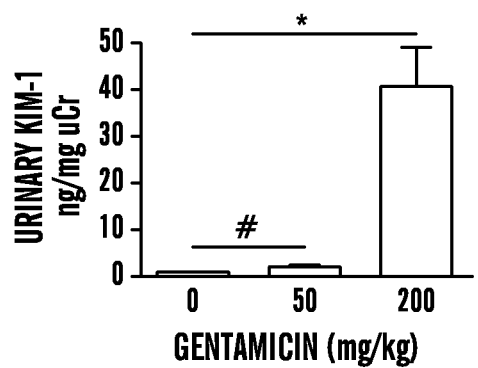
Figure 1L:
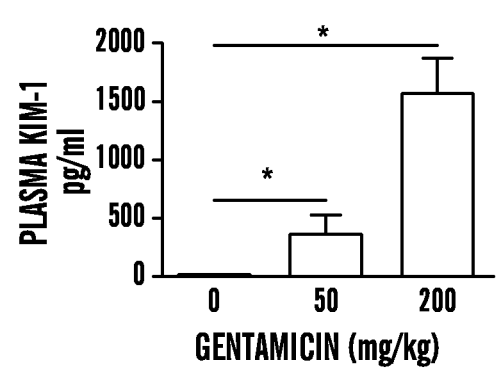

The inventors also investigated whether plasma KIM-1 levels can serve as a biomarker in gentamicin-induced kidney injury in a different rodent species, rats. Rats were injected with gentamicin, 50 or 200 mg/kg per day, for 10 continuous days. Plasma, urine, and kidney tissue were collected on day 11. The extent of kidney damage was assessed by histo-pathologic analysis and changes in plasma creatinine. After 10 days of treatment with 50 mg/kg gentamicin per day, kidney tissues showed brush border loss, focal tubular necrosis, and interstitial inflammation (FIG. 1H). In rats treated with daily doses of 200 mg/kg gentamicin, there was extensive diffuse cell necrosis (FIGS. 1, H and I). The lumens of the tubules were filled with casts and dead cells. Plasma creatinine was significantly elevated in rats treated with 200 mg/kg but not those treated with 50 mg/kg gentamicin (FIG. 1J). Consistent with the histopathologic changes, both urinary (FIG. 1K) and plasma (FIG. 1L) KIM-1 levels were significantly increased after 10 daily doses of 50 or 200 mg/kg gentamicin in rats. Thus, plasma KIM-1 is a sensitive marker of ischemia and toxin-induced injury to the proximal tubule in mice and rats.

Example 3

KIM-1 Protein Levels in the Blood of Human Subjects with AKI

The inventors extended the animal model studies to humans to evaluate whether plasma KIM-1 is elevated in patients with AKI. Plasma and urine samples were obtained from 48 healthy volunteers, 16 post-cardiac surgery (CS) patients without AKI who were admitted to the intensive care unit (ICU), and 28 patients who developed AKI following cardiac surgery (n=22) or after admission to the ICU due to other causes (n=6). AKI samples were chosen to be close in time to peak serum creatinine values. AKI was defined using KidneyDisease Improving Global Outcomes (KDIGO) criteria as a $50% increase in plasma creatinine over baseline within 7 days or an increase in serum creatinine by 0.3 mg/dl within 2 days.[13] An increase in serum creatinine concentration is currently used for the diagnosis of functional AKI, although it has limited sensitivity and specificity.[4,14]

Figure 2E:
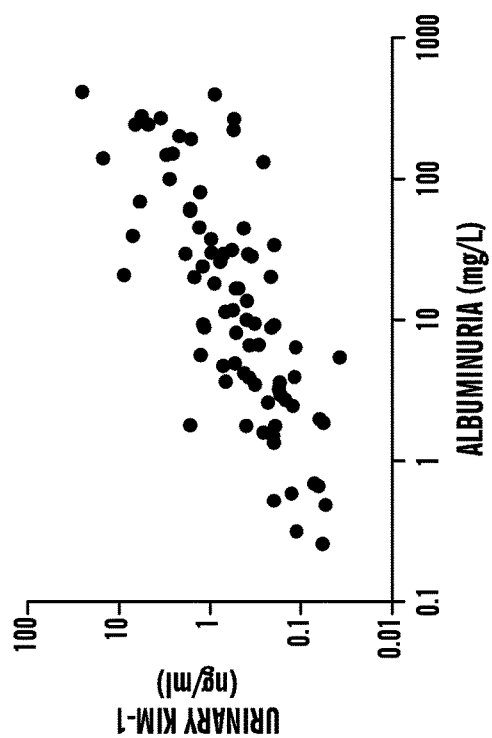
Figure 2F:
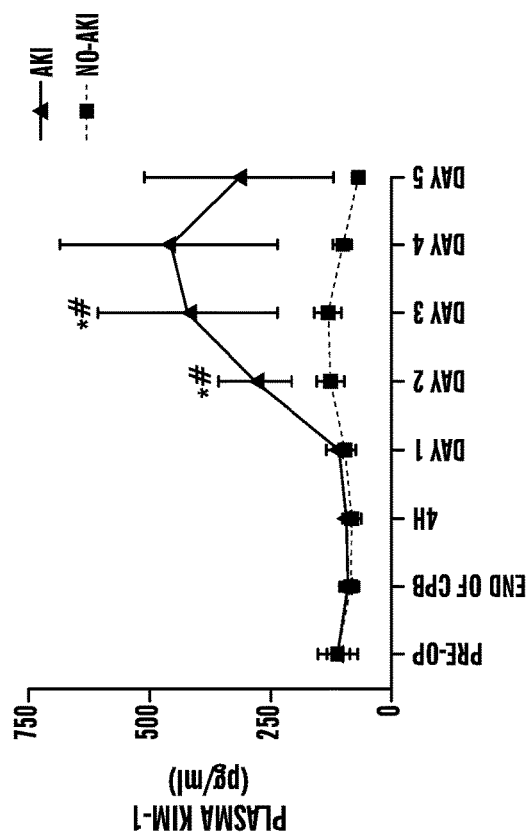
Figure 2G:
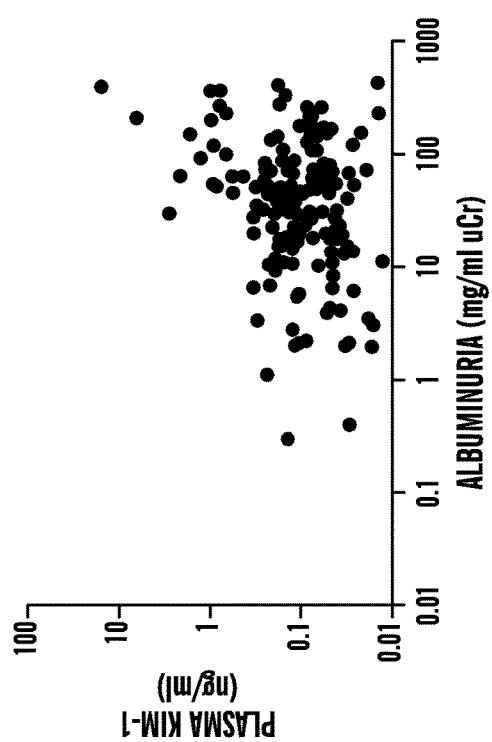

Demographic characteristics, clinical descriptions, serum creatinine, urine albumin, and urinary and plasma KIM-1 values are shown in Table 1 and Table 3. Plasma KIM-1 levels were significantly higher in patients with AKI than healthy volunteers (P<0.001) and patients who had cardiac surgery but did not develop AKI by creatinine criteria (FIG. 2A). There was little overlap in plasma KIM-1 levels between patients with AKI and healthy controls. The slightly higher levels in some of the cardiac surgery patients without AKI may reflect subclinical kidney injury not identified as AKI using creatinine criteria or may reflect underlying sub-clinical CKD. Ongoing proximal tubule injury might be expected in some of these patients because 52% of cardiac surgery/ICU patients without AKI had CKD stage 3 or higher with a mean eGFR of 52 ml/min per 1.73 $m^2$. The area under the receiver-operating characteristic curve (AUC-ROC) of plasma KIM-1 for identifying AKI from all these populations, including both healthy volunteers and CS/ICU patients without AKI, was 0.96 (95% confidence interval [95% CI], 0.92 to 1.02; P<0.001), while the AUC-ROCs were 0.98 (95% CI, 0.97 to 1.00; P<0.001) (FIG. 2C) for normalized urinary KIM-1 and 0.91 (95% CI, 0.85 to 0.97; P<0.001) for non-normalized urinary KIM-1 (FIG. 5B). The difference between the AUC-ROC of plasma and urinary KIM-1 was not statistically significant (P=0.31). Plasma KIM-1 was positively correlated with normalized urinary KIM-1 (r=0.43; P<0.001) (FIG. 2D) and non-normalized urinary KIM-1 (r=0.24; P=0.02) (FIG. 5C). Urinary albumin-to-creatinine ratios were significantly higher (P<0.001) in CS/ICU patients without AKI than in non-hospitalized normal volunteers. Both plasma and urinary KIM-1 were positively correlated with normalized and non-normalized urinary albumin concentration (r=0.33 [P=0.001] for pKIM-1; r=0.35 [P<0.001] for uKIM-1), respectively (FIGS. 2E and 2F). Plasma KIM-1 levels were also correlated with plasma creatinine (r=0.58; P<0.001) (FIG. 2G).

TABLE 1

Characteristics of participants with and without AKI in a cross-sectional study.

| Characteristic | Healthy Volunteers | CS Patients without AKI | CS/ICU Patients with AKI (n = 28) |
|---|---|---|---|
| Age (yr) | 34 ± 1 | 74 ± 2 | 74 ± 2 |
| Men, n (%) | 24 (50) | 10 (63) | 18 (65) |
| Race | | | |
| White | 20 | 15 | 26 |
| African American | 15 | 1 | 1 |
| Asian and others | 13 | | 1 |
| Baseline plasma creatinine (mg/dl) | 0.88 ± 0.02 | 1.32 ± 0.1 | 1.23 ± 0.1 |
| Albumin-to-creatinine ratio (mg/g urinary creatinine) | 5.2 (2.09 to 7.5) | 71.7 (12.8 to 130.6) | 193.7 (118.4 to 269) |
| Baseline eGFR (ml/min per 1.73 m$^2$)$^a$ | 93.8 ± 2.6 | 51.7 ± 3.8 | 60.1 ± 4.4 |
| Plasma KIM-1 (pg/ml) | 64.4 (51 to 77.7) | 205.7 (62.15 to 349.3) | 1458 (274.8 to 2641) |
| Urinary KIM-1 (ng/mg urinary | 0.29 | 0.77 | 5.9 |

Values for continuous variables given as mean ± SEM or mean (95% CI).
CS, cardiac surgery.
$^a$Baseline eGFR was calculated using the Modification of Diet in Renal Disease equation.

TABLE 4

Demographics, serum creatine, urine albumin and plasma KIM-1 values in healthy volunteers and patients. (Abbreviations: A, Asian; AKI, acute kidney injury; B, Black; CS, cardiac surgery; ICU, intensive care unit; HW, Hispanic White; M, Multi-racial; W, white)

| Subject | Group | Age/sex/race | Baseline | SCr on day of collection (mg/dL) | Plasma KIM-I (pg/mL) | Urine K1M-1 (ng/mg uCr) | Albuminuria (mg/g uCr) |
|---|---|---|---|---|---|---|---|
| 1 | HV | 32/F/A | — | 0.79 | 101.65 | 0.47 | 2.1 |
| 2 | HV | 40/M/A | — | 0.88 | 16.51 | 0.49 | 3 |
| 3 | HV | 20/1v1/B | — | 1.07 | 53.29 | 0.07 | 4 |
| 4 | HV | 21/M/A | — | 0.97 | 86.44 | 0.23 | 2.2 |
| 5 | HV | 44/1v1/B | — | 1.12 | 65.27 | 0.07 | 10.2 |
| 6 | HV | 21/M/A | — | 0.87 | 46.37 | 0.44 | 8.1 |
| 7 | HV | 35/F/B | — | 0.76 | 140.27 | 0.07 | 0.3 |
| 8 | HV | 48/M/B | — | 1.11 | 18.53 | 0.11 | 3.5 |
| 9 | HV | 45/F/A | — | 0.85 | 36.43 | 0.23 | 4.1 |
| 10 | HV | 39/F/A | — | 0.85 | 46.37 | 0.41 | 10.6 |
| 11 | HV | 33/M/B | — | 1.04 | 49.59 | 0.13 | 4.2 |
| 12 | HV | 37/M/A | — | 0.87 | 29.53 | 0.23 | 2.1 |
| 13 | HV | 21/F/A | — | 0.83 | 29.53 | 0.14 | 0.4 |
| 14 | HV | 26/F/W | — | 1.04 | 59.08 | 0.22 | 0 |
| 15 | HV | 25/F/W | — | 0.9 | 33.01 | 0.19 | 2 |
| 16 | HV | 42/114/W | — | 0.89 | 240.03 | 0.24 | 1.1 |
| 17 | HV | 33/M/W | — | 1.05 | 118.21 | 0.28 | 2 |
| 18 | HV | 50/1v1/W | — | 1.11 | 12.98 | 0.37 | 11.1 |
| 19 | HV | 24/M/W | — | 0.99 | 106.52 | 0.10 | 0 |
| 20 | HV | 32/1$^7$/B | — | 0.76 | 77.39 | 0.17 | 0 |
| 21 | HV | 29/M/A | — | 0.98 | 20.48 | 0.16 | 3.28 |
| 22 | HV | 28/1v1/B | — | 1.01 | 34.56 | 0.10 | 3.38 |
| 23 | HV | 46/M/13 | — | 0.98 | 123.67 | 0.14 | 5.09 |
| 24 | HV | 28/F/B | — | 0.98 | 113.12 | 0.11 | 5.24 |
| 25 | HV | 43/M/B | — | 0.99 | 34.45 | 0.17 | 3.61 |
| 26 | HV | 45/M/W | — | 0.95 | 67.23 | 0.56 | 22.29 |
| 27 | HV | 46/M/W | — | 1 | 33.32 | 0.24 | 2.26 |
| 28 | HV | 42/M/W | — | 1 | 156.76 | 0.20 | 2.22 |
| 29 | HV | 19/F/W | — | 0.56 | 33.45 | 0.41 | 3.30 |
| 30 | HV | 35/M/W | — | 0.87 | 29.67 | 0.10 | 17.70 |
| 31 | HV | 31/F/B | — | 0.67 | 89.65 | 0.26 | 2.65 |
| 32 | HV | 23/F/W | — | 0.73 | 18.47 | 0.28 | 49.52 |
| 33 | HV | 25/F/W | — | 0.76 | 88.97 | 1.52 | 1.73 |
| 34 | HV | 25/F/W | — | 0.8 | 65.78 | 0.27 | 4.33 |
| 35 | HV | 48/F/W | — | 0.9 | 33.67 | 0.60 | 3.29 |
| 36 | HV | 26/F/W | — | 0.76 | 98.65 | 0.12 | 2.86 |
| 37 | HV | 30/F/B | — | 0.96 | 36.89 | 0.16 | 1.72 |
| 38 | HV | 30/M/W | — | 0.72 | 12.86 | 0.35 | 6.01 |
| 39 | HV | 27/F/A | — | 0.71 | 11.98 | 0.43 | 4.08 |
| 40 | HV | 36/M/A | — | 0.78 | 98.34 | 0.24 | 4.52 |
| 41 | HV | 35/F/M | — | 0.86 | 101.55 | 0.22 | 2.13 |
| 42 | HV | 27/F/W | — | 0.71 | 47.89 | 0.35 | 2.84 |
| 43 | HV | 20/111/A | — | 0.97 | 101.23 | 0.37 | 1.71 |
| 44 | HV | 20/F/W | — | 0.69 | 111.32 | 0.34 | 1.58 |
| 45 | HV | 49/F/13 | — | 0.95 | 78.53 | 0.27 | 9.37 |

TABLE 4-continued

Demographics, serum creatine, urine albumin and plasma KIM-1 values in healthy volunteers and patients. (Abbreviations: A, Asian; AKI, acute kidney injury; B, Black; CS, cardiac surgery; ICU, intensive care unit; HW, Hispanic White; M, Multi-racial; W, white)

| Subject | Group | Age/sex/race | Baseline | SCr on day of collection (mg/dL) | Plasma KIM-1 (pg/mL) | Urine KIM-1 (ng/mg uCr) | Albuminuria (mg/g uCr) |
|---|---|---|---|---|---|---|---|
| 46 | HV | 43/M/A | — | 0.99 | 17.87 | 0.37 | 2.46 |
| 47 | HV | 51/F/B | — | 0.98 | 46.78 | 0.29 | 6.21 |
| 48 | HV | 41/F/B | — | 0.53 | 16.37 | 0.48 | 3.71 |
| 49 | CS - no AKI | 77/F/W | 0.9 | 0.73 | 123.34 | 1.55 | 35 |
| 50 | CS - no AKI | 751 M/W | 1.31 | 1.04 | 957.70 | 0.69 | 53.8 |
| 51 | CS -no AKI | 79/M/W | 1.4 | 1.12 | 243.26 | 0.47 | 45 |
| 52 | CS - no AKI | 76/M/W | 1.21 | 0.84 | 37.92 | 0.72 | 23.6 |
| 53 | CS - no AKI | 58/M/W | 1.12 | 1.25 | 14.64 | 0.88 | 429.94 |
| 54 | CS - no AKI | 83/M/W | 0.94 | 0.93 | 26.49 | 1.38 | 0 |
| 55 | CS - no AKI | 83/F/W | 1.27 | 0.98 | 108.00 | 0.52 | 3.52 |
| 56 | CS - no AKI | 76/M/W | 1.49 | 1.55 | 123.34 | 0.98 | 10.6 |
| 57 | CS - no AKI | 69/M/W | 2.25 | 1.9 | 14.64 | 0.44 | 231.13 |
| 58 | CS - no AK! | 781 M/W | 0.98 | 0.83 | 339.58 | 0.47 | 20.1 |
| 59 | CS - no AKI | 78/F/W | 1.33 | 1.07 | 164.03 | 0.82 | 88.1 |
| 60 | CS -no AKI | 82/F/W | 1.15 | 0.94 | 60.06 | 0.97 | 31 |
| 61 | CS -no AKI | 57/F/W | 1.03 | 0.81 | 253.01 | 0.88 | 59.38 |
| 62 | CS-no AKI | 84/F/W | 2.27 | 1.8 | 81.56 | 0.67 | 31 |
| 63 | CS - no AKI | 59/M/W | 1.45 | 1.38 | 17.12 | 0.75 | 2 |
| 64 | CS - no AKI | 67/M/H | 1.15 | 1.23 | 727.00 | 0.16 | 82.56 |
| 65 | CS - AKI | 81/MON | 1 | 2.23 | 2831.71 | 1.69 | 30.05 |
| 66 | CS - AKI | 67/M/W | 1.49 | 3.11 | 184.07 | 0.95 | 406 |
| 67 | CS - AKI | 64/M/W | 2.2 | 5 | 15579.65 | 7.47 | 400 |
| 68 | CS - AKI | 63/F/W | 1.03 | 2.08 | 663.37 | 2.28 | 230 |
| 69 | CS - AKI | 56/M/W | 1.82 | 4.1 | 6334.09 | 20.54 | 209 |
| 70 | CS - AKI | 71/M/W | 1.08 | 2.9 | 971.10 | 5.31 | 202 |
| 71 | ICU - AEG | 41/M/W | 0.9 | 4.21 | 922.42 | 3.42 | 120 |
| 72 | ICU-AKI | 62/M/1V | 1 | 4.05 | 1019.23 | 6.74 | 368 |
| 73 | ICU - AKI | 75/M/W | 1 | 2.8 | 663.37 | 1.20 | 100.4 |
| 74 | ICU - AKI | 78/M/W | 0.8 | 3.05 | 572.40 | 1.25 | 45.7 |
| 75 | ICU - AKI | 80/M/W | 0.7 | 2.47 | 60.06 | 2.72 | 56.4 |
| 76 | ICU - AKI | 74/M/W | 1.3 | 2.23 | 771.32 | 20.32 | 368 |
| 77 | CS - AKI | 70/M/W | 1.74 | 2.7 | 284.81 | 7.49 | 298.0 |
| 78 | CS - AKI | 85/F/B | 0.95 | 1.35 | 311.24 | 0.87 | 35.1 |
| 79 | CS - AKI | 89/F/W | 1.18 | 2.14 | 403.11 | 4.93 | 82.8 |
| 80 | CS - AKI | 84/F/W | 0.87 | 1.6 | 184.81 | 0.82 | 105.6 |
| 81 | CS - AKI | 82/M/W | 1.32 | 2.23 | 544.74 | 1.68 | 20.9 |
| 82 | CS - AKI | 90/F/W | 1.3 | 2.27 | 184.81 | 2.68 | 176.0 |
| 83 | CS - AKI | 96/F/W | 1.14 | 2 | 403.11 | 3.12 | 115.5 |
| 84 | CS - AKI | 56/M/HW | 2.6 | 4.01 | 258.64 | 9.76 | 811.4 |
| 85 | CS - AKI | 80/M/W | 0.66 | 1.4 | 1027.26 | 10.97 | 572.0 |
| 86 | CS - AKI | 72/M/W | 1.52 | 2.5 | 258.64 | 5.54 | 14.2 |
| 87 | CS - AKI | 60/F/W | 1.22 | 2.21 | 331.31 | 1.94 | 110.3 |
| 88 | CS - AKI | 79/14/W | 0.82 | 1.57 | 544.74 | 2.99 | 43.1 |
| 89 | CS - AKI | 83/M/W | 2.1 | 2.52 | 3291.32 | 28.96 | 169.8 |
| 90 | CS - AKI | 78/M/W | 1.19 | 2.6 | 518.15 | 3.48 | 74.5 |
| 91 | CS - AKI | 82/F/W | 0.89 | 1.68 | 412.31 | 1.76 | 65.6 |
| 92 | CS - AKI | 77/F/W | 0.7 | 1.24 | 1293.48 | | |

To obtain information on the time course of plasma KIM-1 elevation in humans with AKI, the inventors collected plasma and urine samples from patients (Table 2) before cardiopulmonary bypass (CPB) surgery; at the end of CPB; and then at 4 hours, 12 hours (urine only), and daily for 5 days after CPB. KIM-1 and albumin were measured in samples from nine patients with and nine patients without AKI. The time required for diagnosis of AKI (KDIGO criteria, stage 1) was a median of 3 days (range, 2-6 days).

TABLE 2

Characteristics of participants with and without AKI in longitudinal study. (Values for continuous variables given as mean ± SEM. CABG, coronary artery bypass grafting. aBaseline eGFR was calculated using the Modification of Diet in Renal Disease equation.)

| Characteristic | Patients with AKI (n = 9) | Patients without AKI (n = 9) |
|---|---|---|
| Age (yr) | 73.4 ± 8.2 | 74.3 ± 8.6 |
| Men, n (%) | 5 (56) | 7 (78) |
| White race (n) | 9 | 9 |
| Mean baseline serum | 1.2 ± 0.4 | 1.1 ± 0.2 |
| Baseline eGFR (ml/min per 1.73 m$^2$)$^a$ | 57.1 ± 13.8 | 65.1 ± 12.4 |
| CABG | 1 (11) | 5 (55) |
| Valve or combined CABG/valve, n (%) | 8 (88) | 4 (44) |

Figure 2H:
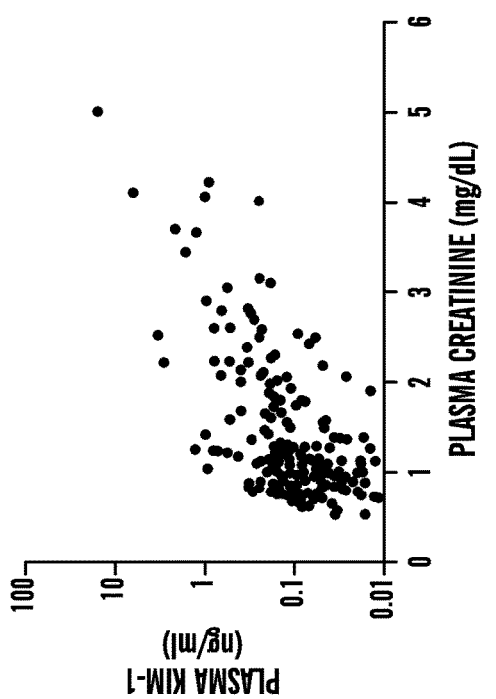
Figure 2I:
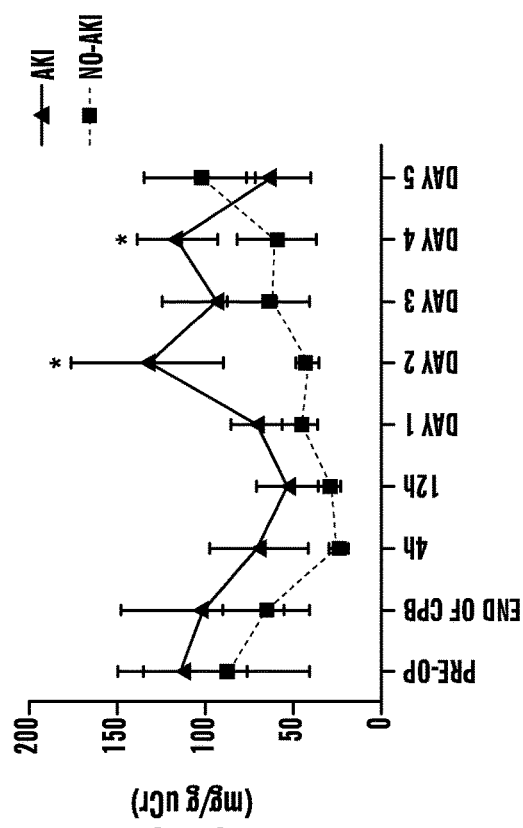
Figure 2J:
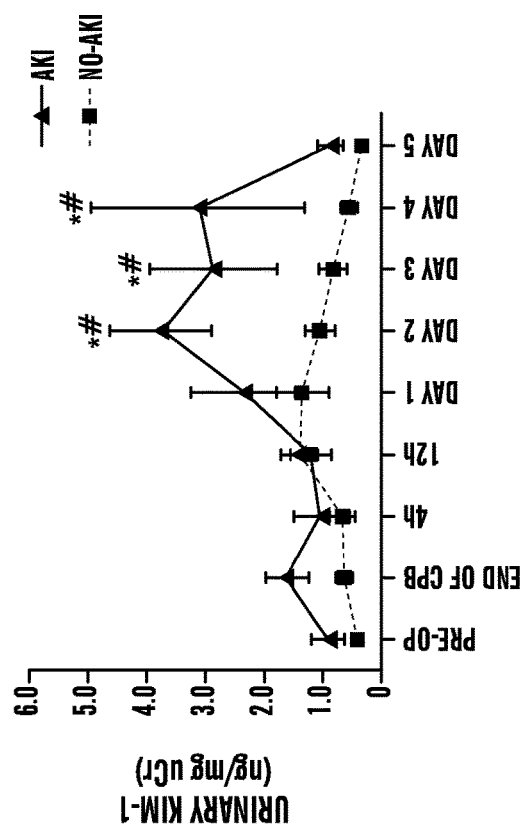

Plasma KIM-1 levels at day 2 were significantly elevated versus baseline levels in patients with AKI (P<0.01) compared with patients who did not develop AKI at this time. The AUC-ROC was 0.74 (95% CI, 0.48 to 0.91) (FIG. 2H). The AUC-ROC for plasma, urinary KIM-1, and urinary albumin at various time points after CPB are provided in Table 5. Normalized urinary KIM-1 levels were elevated on day 1 and significantly elevated at day 2 in patients who developed AKI compared with baseline levels (P=0.003) and levels in patients without AKI (P<0.02) (FIG. 2I). Urinary albumin levels, normalized to urinary creatinine, fell and then rose slightly in patients with and without AKI, but did not differ statistically compared with baseline levels at any time point in patients with AKI (FIG. 2J).

Table 5: Biomarker values in patents undergoing cardiac surgery. Urine and plasma samples were not available from all patients at all time points. Abbreviations: AUC-ROC, area under the receiver operating characteristics curve; AKI, acute kidney injury; End, end of the surgery. Asterisks mark the time point at which biomarker levels were statistically significantly higher than baseline levels in patients with AKI.

| | Plasma KIM-1 (pg/mL) | | | Urinary KIM-1 (ng/mg uCr) | | | Urinary albumin (mg/g uCr) | | |
|---|---|---|---|---|---|---|---|---|---|
| | AKI Median (IQR) [N] | No AKI Median (IQR) [N] | AUC-ROC | AKI Median (IQR) [N] | No AKI Median (IQR) [N] | AUC-ROC | AKI Median (IQR) [N] | No AKI Median (IQR) [N] | AUC-ROC |
| Pre | 128.8 (41.3, 167.5) [8] | 82.0 (49.8, 154.4) [5] | 0.55 (0.26-0.82) | 505.2 (398.6, 1531.9) [8] | 358.4 (150.2, 682.9) [5] | 0.73 (0.42-0.93) | 120.9 (27.8, 137.5) [6] | 67.0 (14.0, 128.0) [5] | 0.63 (0.31-0.89) |
| End | 97.5 (41.7, 134.4) [7] | 76.9 (42.4, 100.2) [9] | 0.51 (0.25-0.76) | 1499.3 (956.0, 2047.4) [7] | 503.1 (341.9, 1041.3) [9] | 0.81 (0.54-0.96) | 85.9 (23.3, 150.3) [5] | 27.1 (13.3, 96.8) [9] | 0.67 (0.37-0.89) |
| 4 h | 90.5 (52.3, 133.5) [8] | 86.2 (51.5, 107.6) [7] | 0.59 (0.31-0.83) | 444.6 (376.7, 1038.7) [9] | 585.7 (313.9, 643.1) [7] | 0.52 (0.27-0.77) | 30.5 (13.5, 127.8) [7] | 19.9 (15.6, 33.9) [7] | 0.65 (0.36-0.88) |
| 12 h | — | — | | 972.9 (511.8, 1511.9) [8]* | 1033.6 (871.6, 2050.1) [8] | 0.61 (0.34-0.84) | 44.2 (19.3, 64.9) [6] | 32.4 (12.1, 41.8) [8] | 0.67 (0.37-0.89) |
| Day 1 | 114.2 (58.3, 167.2) [8] | 81.3 (62.3, 120.5) [8] | 0.55 (0.29-0.79) | 1464.0 (1198.3, 2055.8) [9] | 1069.6 (608.3, 1646.8) [7] | 0.65 (0.38-0.87) | 52.3 (42.2, 92.0) [7] | 48.6 (18.7, 68.5) [7] | 0.71 (0.42-0.92) |
| Day 2 | 230.2 (160.7, 365.1) [9]* | 103.9 (70.0, 155.1) [8] | 0.74 (0.48-0.91) | 3643.1 (1355.0, 5092.8) [9] | 991.2 (532.6, 1487.2) [8] | 0.89 (0.64-0.99) | 72.7 (47.9, 213.2) [7] | 46.8 (24.8, 52.4) [8] | 0.77 (0.49-0.94) |
| Day 3 | 241.2 (144.7, 447.5) [8] | 125.3 (59.5, 169.6) [9] | 0.78 (0.52-0.94) | 1570.6 (1017.3, 4101.7) [8] | 512.4 (323.0, 1083.2) [9] | 0.73 (0.42-0.93) | 52.5 (47.1, 104.9) [7] | 45.7 (22.3, 72.8) [9] | 0.65 (0.38-0.87) |
| Day 4 | 197.5 (117.5, 458.5) [9] | 89.1 (62.5, 137.7) [7] | 0.81 (0.54-0.96) | 1285.1 (847.1, 2170.4) [9] | 645.3 (477.7, 686.0) [6] | 0.83 (0.56-0.97) | 142.1 (70.0, 156.7) [7] | 45.8 (13.6, 72.2) [6] | 0.76 (0.45-0.95) |
| Day 5 | 112.0 (94.3, 244.1) [6] | — [1] | | 785.5 (473.0, 1269.5) [7] | 348.7 (231.5, 466.0) [2] | 0.86 (0.48-0.99) | 46.4 (24.8, 85.5) [5] | 102.3 (70.7, 133.8) [2] | — |

Example 4

KIM-1 Protein Levels in the Blood of Human Subjects With Diabetes

Blood KIM-1 levels were also evaluated in two groups of patients with various stages of CKD. The first group included clinic patients with CKD due to various causes (Tables 6 and 7), and the second group included a cohort of 124 patients with type 1 diabetes and proteinuria (>500 mg albumin/24 hours) with longitudinal follow-up. Characteristics of the groups are provided in Table 6.

TABLE 6

Characteristics of two study groups with CKD. Values for continuous variables given as mean ± SD; values for categorical variables given as number or number (percentage).

|  | CKD patients (n = 46) | Type I Diabetes and Proteinuria (n = 124) |
|---|---|---|
| Age (y) | 49 ± 2 | 42 ± 2 |
| Male | 35 (76%) | 72 (58%) |
| Race |  |  |
| White | 30 | 123 |
| African American | 9 | 1 |
| Asian & Others | 7 |  |
| sCr (mg/dL) | 2.43 ± 0.2 | 1.39 ± 0.9 |
| eGFR* (mL/min/1.73 m$^2$) | 41.4 ± 4.5 | 68 ± 34 |
| Plasma KIM-1 (pg/ml) |  |  |
| CKD stage 1 | 83 ± 55 (p) | 89 ± 70 (s) |
| CKD stage 2 | 104 ± 98 (p) | 158 ± 173 (s) |
| CKD stage 3 | 201 ± 162 (p) | 181 ± 178 (s) |
| CKD stage 4 | 261 ± 126 (p) | 288 ± 336 (s) |
| CKD stage 5 | 360 ± 172 (p) | 770 ± 770 (s) |

Abbreviations:
CKD, chronic kidney injury;
eGFR, estimated glomerular filtration rate;
sCr, serum creatinine, (p) plasma, (s) serum.
*Baseline eGFR wa scalculated using MDRD equation.

TABLE 7

Various etiologies of chronic kidney disease

| Pathology |  |
|---|---|
| Glomerular | IgA Nephropathy (N = 10) |
|  | Focal glomerulosclerosis (N = 4) |
|  | Membranous Glomerulonephritis (N = 5) |
|  | Lupus (N = 2) |
|  | Others (N = 2) |
| Tubulointerstitial | Polycystic kidney disease (N = 4) |
|  | Chronic interstitial toxicity (N = 2) |
|  | Lithium Toxicity (N = 2) |
| Other | Diabetes/Hypertension/others (N = 15) |

Figure 3A:
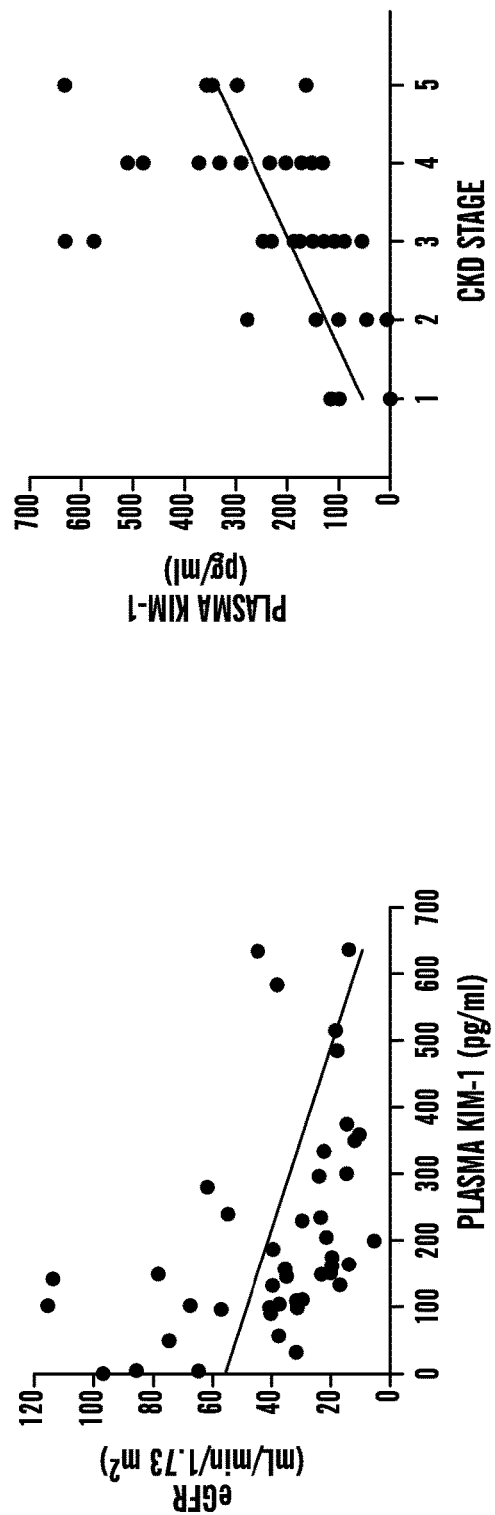
FIGS. 3A-3F shows blood KIM-1 as a biomarker of CKD and predictor of progression of patients with type 1 diabetes.
Figure 3B:
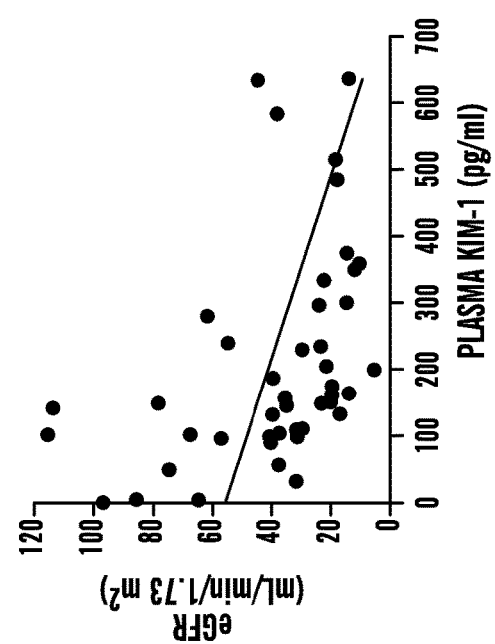
Figure 3D:
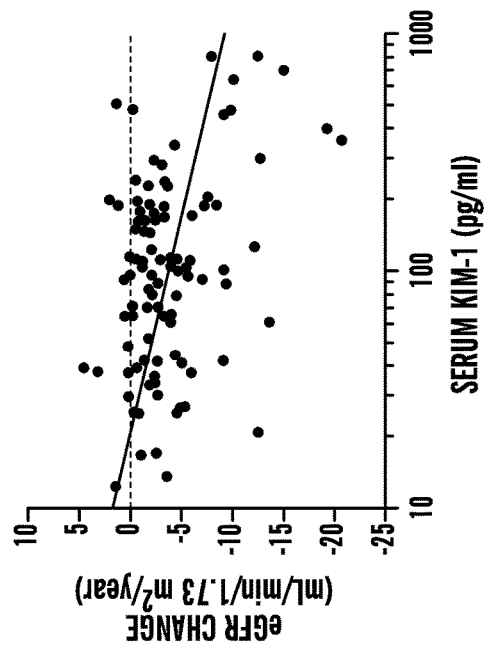
Figure 3F:
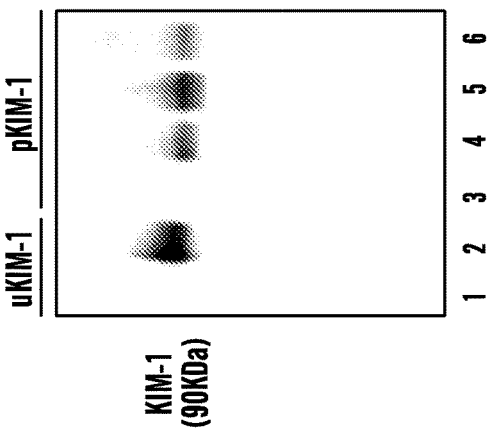
Figure 3C:
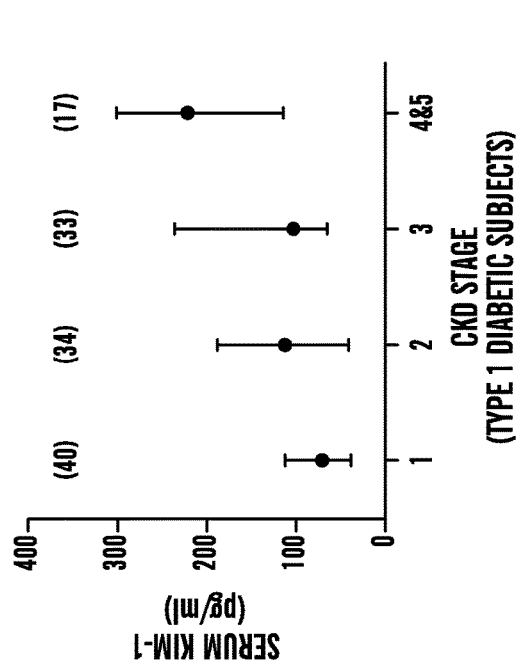

In both groups, blood KIM-1 levels increased with increasing CKD stage (FIG. 3A-3C). Whereas the first group did not have follow-up, the group of patients with type 1 diabetes and proteinuria were followed for 5-15 years to ascertain the rate of eGFR loss using serial measurements of serum creatinine and the occurrence of ESRD. FIG. 3D shows the strong relationship of baseline serum KIM-1 levels with rate of eGFR decline during the 5-15 year follow-up period with a median follow-up of 10 years, in 107 diabetic patients with stages 1-3 CKD at baseline; Spearman correlation coefficient=0.52 (P<0.001). The association of baseline serum KIM-1 levels with rate of eGFR loss was the strongest and highly statistically significant (P<0.001) in multiple regression analysis when other baseline characteristics, such as eGFR, urinary albumin-to-creatinine ratio, and hemoglobin A1c were considered. During the follow-up period, 24 of the 107 patients who had stage 1-3 CKD at baseline developed ESRD.[15]

Figure 3E:
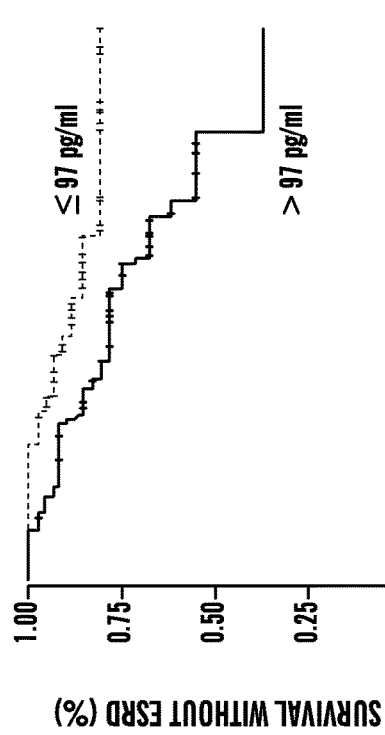
Figure 4A:
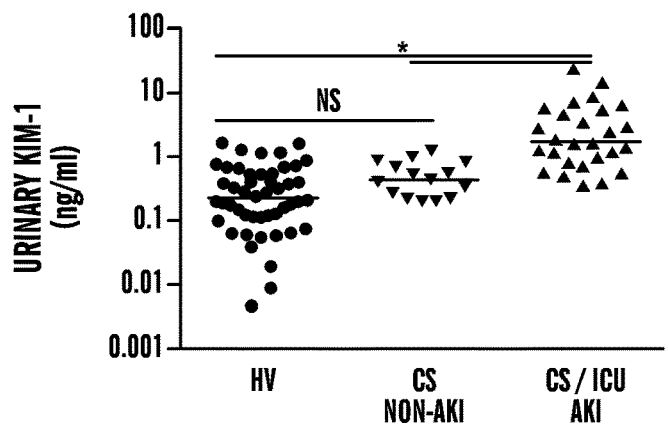
FIGS. 4A-4C shows the performance of non-normalized urinary KIM-1. Plasma and urine were collected from healthy volunteers, post cardiac surgery (CS) patients with or without AKI.
Figure 4B:
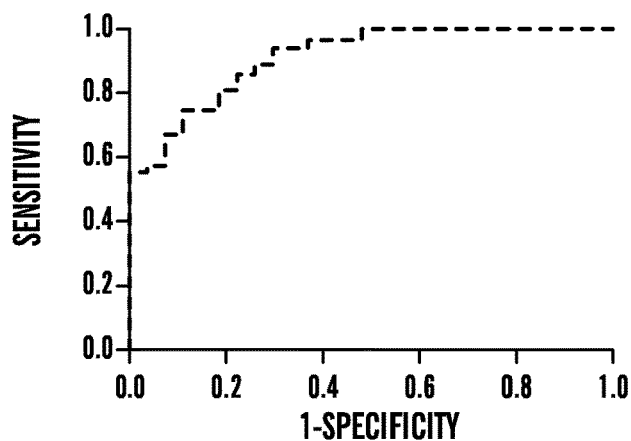
Figure 4C:
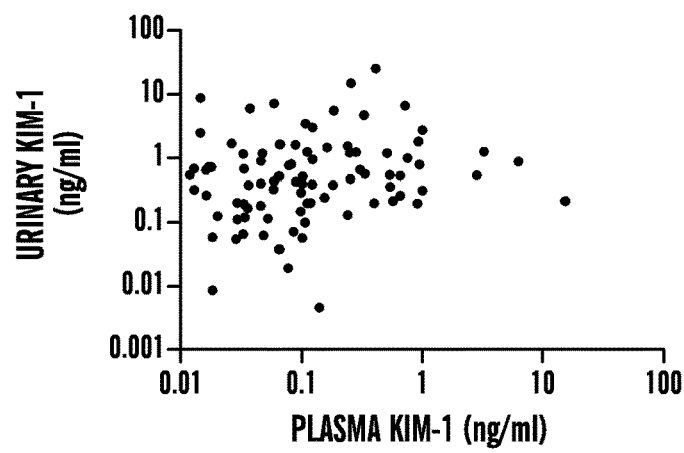

To further examine the association of baseline serum KIM-1 with risk of ESRD, Kaplan-Meier survival analysis was performed. As shown in FIG. 3E, after 12.5 years of follow-up, only 20% of patients with serum levels of KIM-1 below the median (97 pg/ml) progressed to ESRD compared with 63% of patients with baseline KIM-1 above the median (P<0.01). This finding was confirmed in multivariate Cox regression analysis. The effect of baseline serum level of KIM-1 on hazard ratio of ESRD was significant (P<0.01) when other baseline covariates, such as eGFR, urinary albumin-to-creatinine ratio, and hemoglobin A1c, were included. The size of the KIM-1 fragment in plasma and urine in patients with AKI and CKD was similar (molecular mass, approximately 90 kD). This is the predicted size of the cleaved ectodomain, and both plasma and urine KIM-1 is recognized by the same antibody (FIG. 3F).

Example 5

Currently, no other blood biomarker specifically reflects kidney proximal tubule injury. Blood KIM-1 reflects the integrated result of kidney proximal tubule injury over a period of time and nicely complements urinary levels in patients to evaluate acute or chronic kidney injury. Plasma KIM-1 may be particularly suitable for detecting chronic ongoing injury. Importantly, although spot urinary KIM-1 concentration, normalized to urinary creatinine concentration, is very attractive as a biomarker given the stability of KIM-1 and the easy accessibility of urine specimens, urinary excretion can vary widely over time in patients with AKI, such that a spot collection may not reflect these variations.[16] The present invention provides a method that reflects a time-averaged production of a kidney injury biomarker, which is useful to complement to the urine measurement.

In both mice and rats, the increase in plasma KIM-1 levels directly reflected the degree of histologic and functional kidney injury. Both plasma and urinary KIM-1 levels were significantly elevated within 3 hours after injury in mice, indicating that both are early and sensitive biomarkers of kidney injury. Plasma KIM-1 levels are elevated in the unilateral ureteral obstruction model of fibrosis, while plasma creatinine is normal, indicating that plasma KIM-1 can also serve as a marker of chronic kidney injury. While healthy kidney tissue expresses very low or undetectable levels of KIM-1, the mRNA of one KIM-1 variant has been reported to be expressed by the liver.[17] The inventors studies herein, using CCl4, a known hepatotoxicant, demonstrate that plasma KIM-1 is not changed with liver toxicity.

In humans, plasma KIM-1 was significantly elevated in patients with established AKI compared with healthy volunteers and hospitalized individuals without AKI after cardiac surgery. Because the definition of AKI relies on changes in plasma creatinine, an insensitive and nonspecific indicator of acute kidney proximal tubule injury, the di-agnostic performance of any biomarker compared with plasma creatinine as a gold standard has to be interpreted in that light.14 Tubular injury may not be associated with an increase in plasma creatinine concentration, and an increase in creatinine does not necessarily reflect in-jury[14] The AUC-ROC of plasma KIM-1 was 0.98 when patients with established AKI were compared with only healthy volunteers in the analysis, excluding the cardiac surgery non-AKI group, some of whom may have had subclinical injury and of whom 52% had CKD stage 3 or higher. The AUC-ROC of plasma and urinary KIM-1 did not significantly differ, although our sample size was limited. Compared with urinary KIM-1 normalized to creatinine (AUC-ROC, 0.98), use of absolute KIM-1 levels resulted in a lower AUC-ROC (0.91) and weaker correlation with plasma KIM-1 (r=0.23) in patients with AKI. Normalization to urine creatinine accounts for variation in water reabsorption along the nephron. According to Waikar et al., "Lower creatinine excretion in the setting of acute kidney injury may amplify a tubular injury biomarker signal, thereby increasing its clinical utility."[16] The AUC-ROC of plasma and urinary KIM-1 to differentiate patients with AKI from those without AKI was high because of the cross-sectional nature of these studies, where the diagnosis of AKI was well established clinically (FIG. 2C), compatible with prior studies.[5] In prospective studies in which all nine patients developed stage 1 AKI, the AUC-ROC was lower (Table 5). In addition to the integrated effects of kidney KIM-1 production and release into the blood, plasma KIM-1 levels will be influenced by the volume of KIM-1 distribution and the renal or extrarenal metabolism and clearance of KIM-1. The correlation coefficient of 0.43 reflects a statistically significant association between urinary and plasma KIM-1. The strong correlation between plasma KIM-1 and plasma creatinine concentration in humans and rodents in the setting of acute injury is not unexpected given that renal tubular injury will increase both these markers.

In patients with CKD of various causes, blood KIM-1 levels were correlated with increasingly advanced stages of disease. Baseline serum KIM-1 performed very well as a predictive biomarker for progressive kidney disease in a type 1 diabetic cohort even after other common covariates, including urinary albumin-to-creatinine ratio, hemoglobin A1c, and eGFR, were taken into account. In some embodiments, the invention encompasses assessing elevation of blood KIM-1 levels to risk-stratify patients, predict outcome (including progression of CKD), and serve as an efficacy biomarker in therapeutic trials. The inventors discovery can be used to determine blood KIM-1 levels to determine the extent of ongoing injury to the kidney over time.

In conclusion, the inventors have discovered that blood KIM-1 protein is a marker of kidney injury in mice, rats, and humans. In humans, blood KIM-1 levels are significantly elevated in the setting of AKI and CKD and predict progression of renal disease in a type 1 diabetic cohort. Thus, KIM-1 protein as a biomarker has utility as a sensitive and specific diagnostic and prognostic marker for kidney injury. Importantly, and in contrast to using other blood biomarkers or KIM-1 levels as a urinary biomarker, the inventors have discovered that KIM-1 blood levels reflects specific injury to the proximal tubule of the kidney, the primary site of injury for ischemia and most nephrotoxicants.[18]

Example 6

Figure 5A:
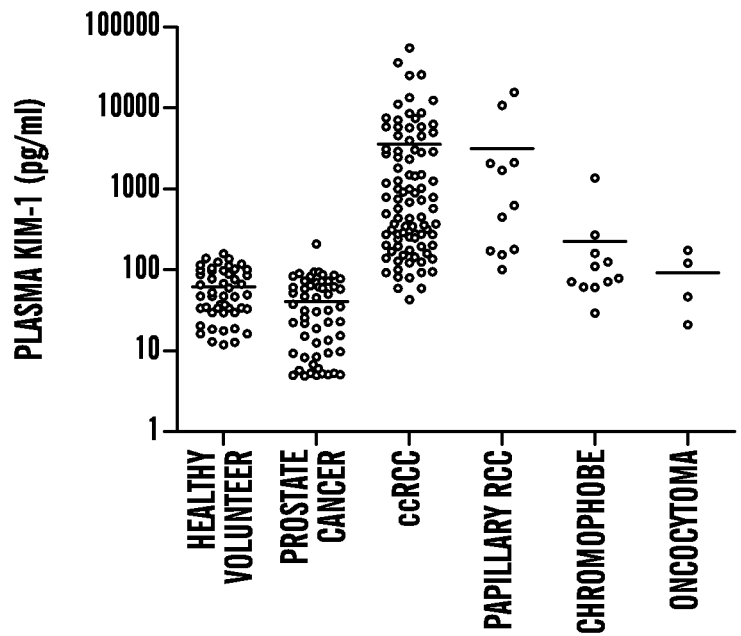
FIGS. 5A-5D shows increase in plasma KIM-1 in RCC.
Figure 5B:
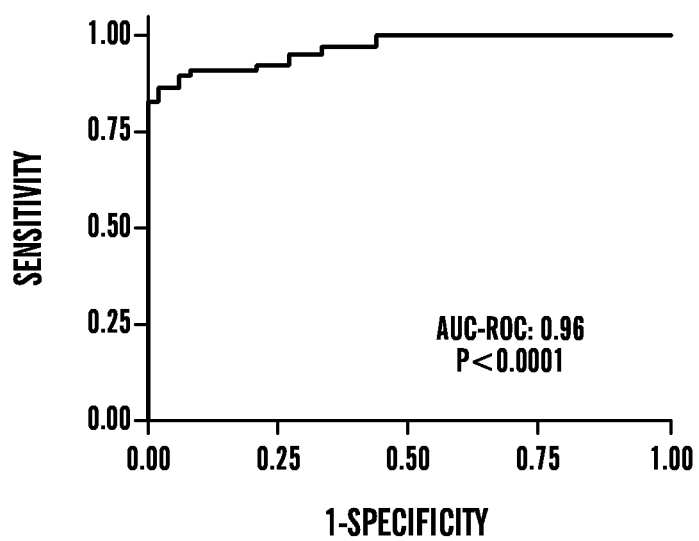
Figure 5C:
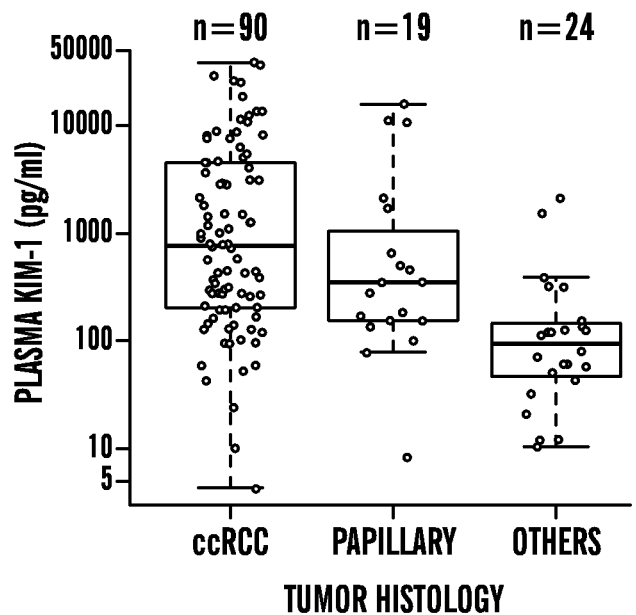
Figure 5D:
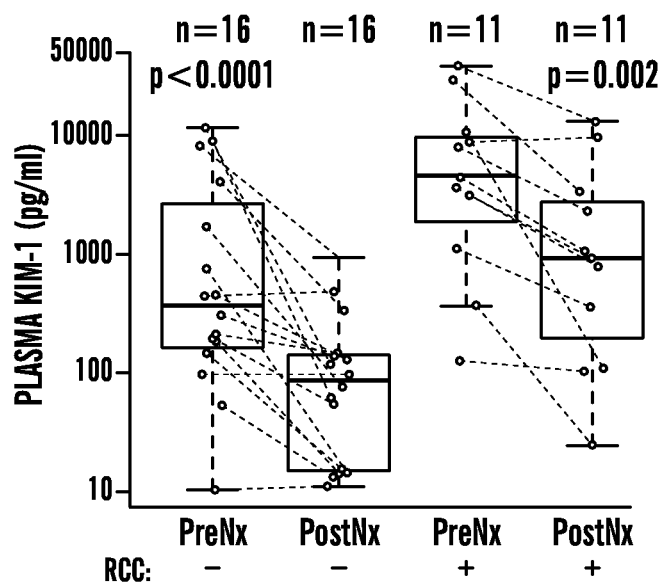
Figure 5E:
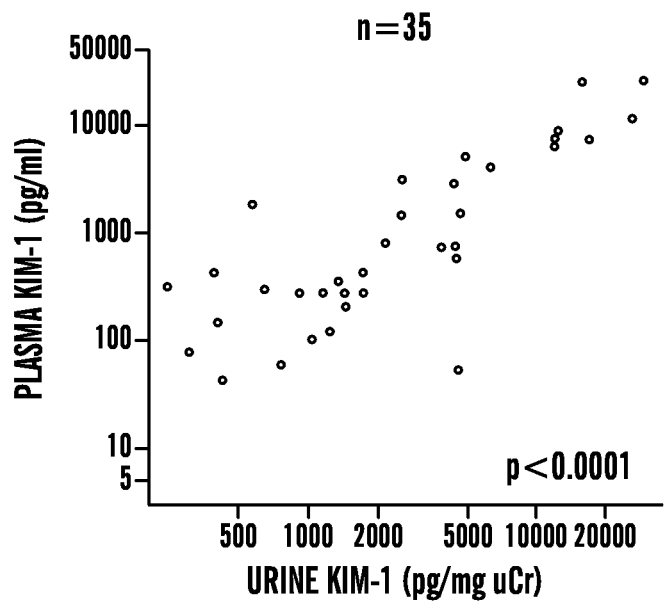
FIG. 5E shows plasma KIM-1 levels are associated with urine KIM-1 levels in subjects with RCC.
Figure 6A:
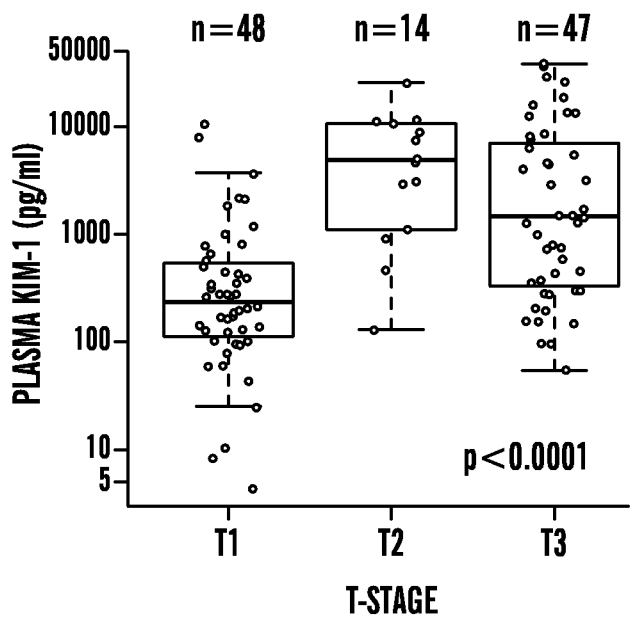
FIGS. 6A-6E shows plasma KIM-1 levels associated with Clinicopathological parameters in subjects with RCC.
Figure 6A:
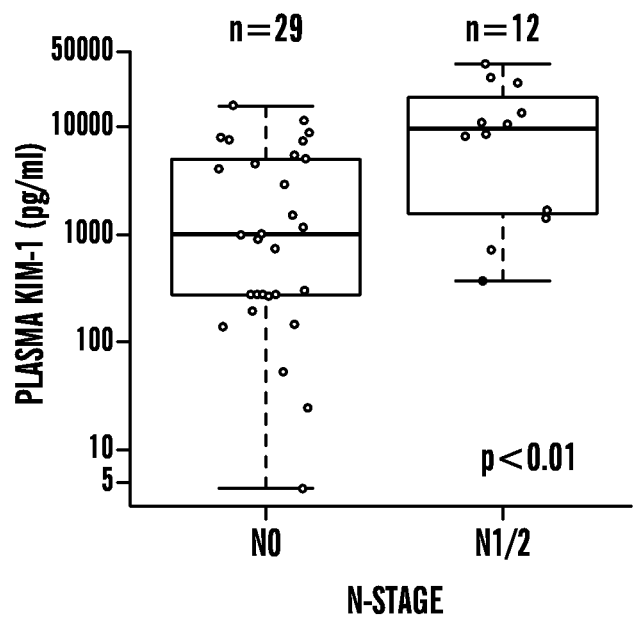
Figure 6A:
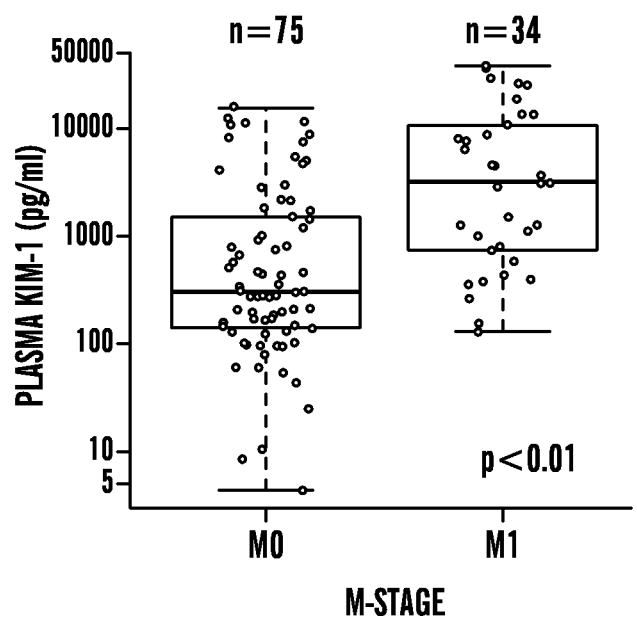
Figure 6B:
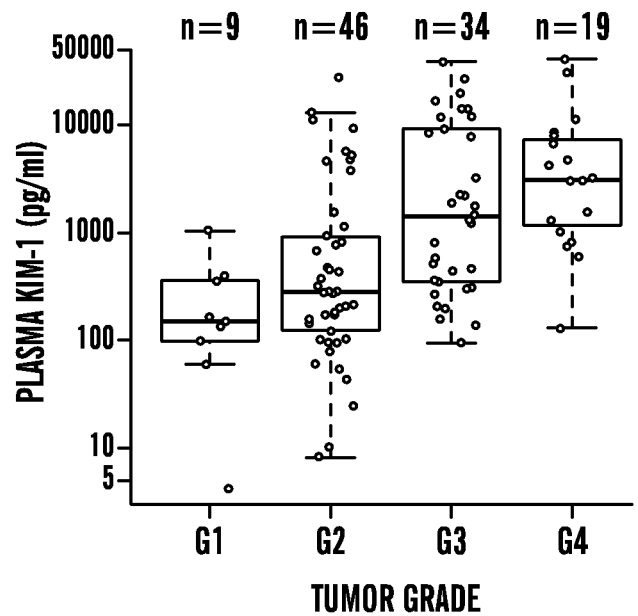
Figure 6C:
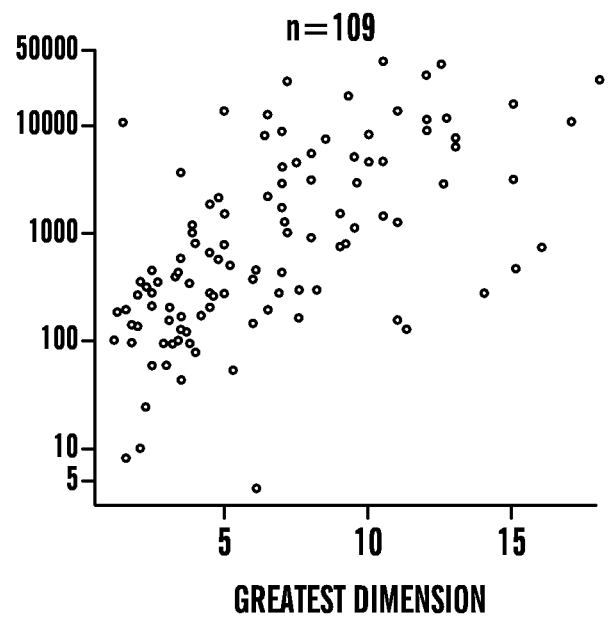
Figure 6D:
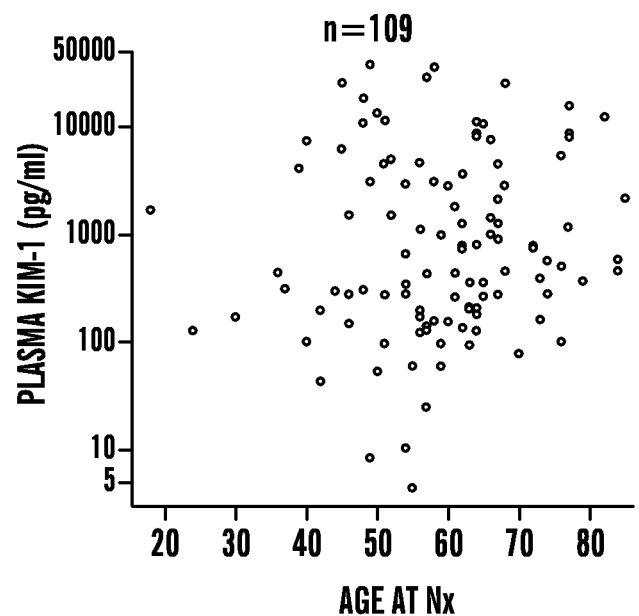
Figure 6E:
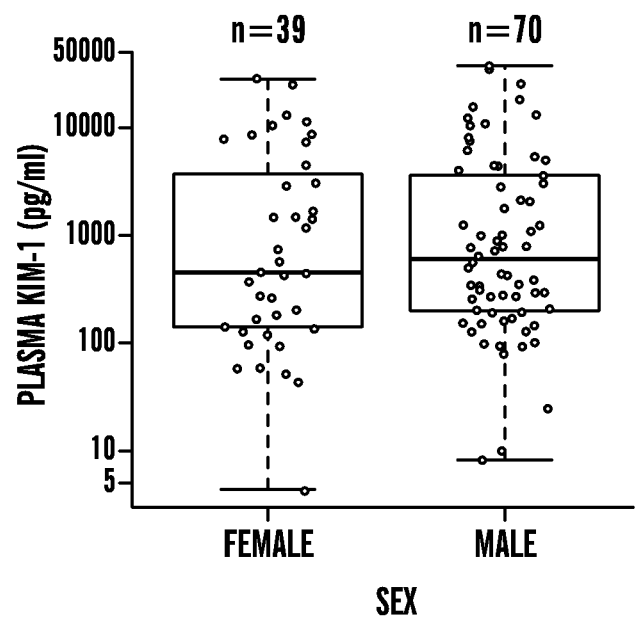
Figure 7A:
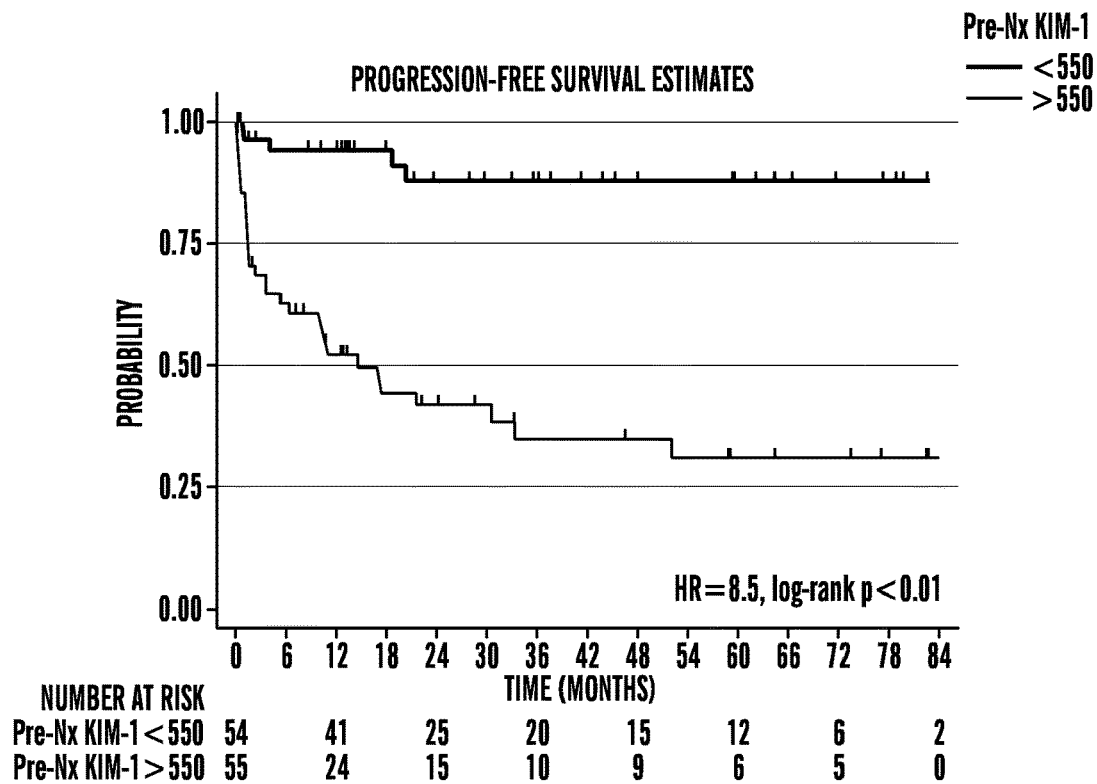
FIG. 7A shows plasma KIM-1 is associated with RCC disease progression and progression free survival (PFS).
Figure 7B:
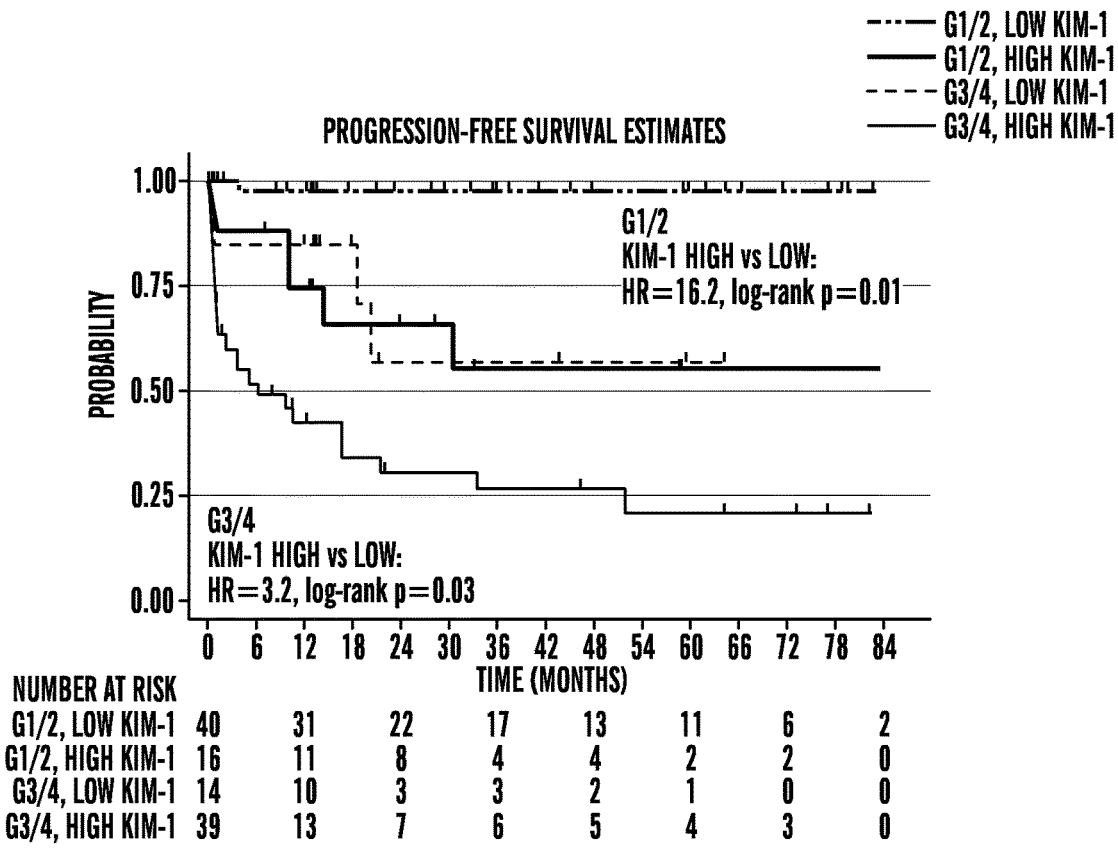
FIG. 7B subjects with grade 3-4 or grade 1-2 RCC with higher plasma KIM-1 levels have a more severe progression as compared to subjects with the same grade of RCC but with lower plasma KIM-1 levels.
Figure 7C:
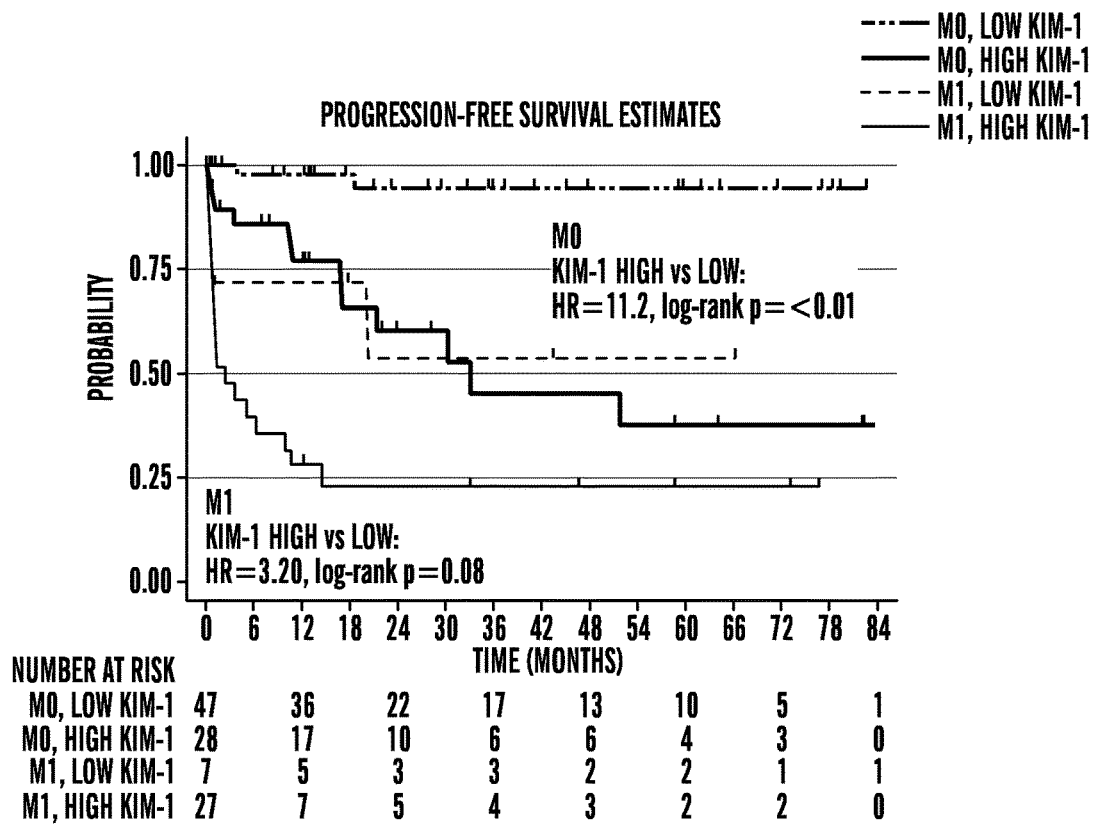
FIG. 7C shows that subjects with metastatic RCC with higher plasma KIM-1 levels have a more severe disease progression as compared to subjects with the metastatic RCC but with lower plasma KIM-1 levels.
Figure 7D:
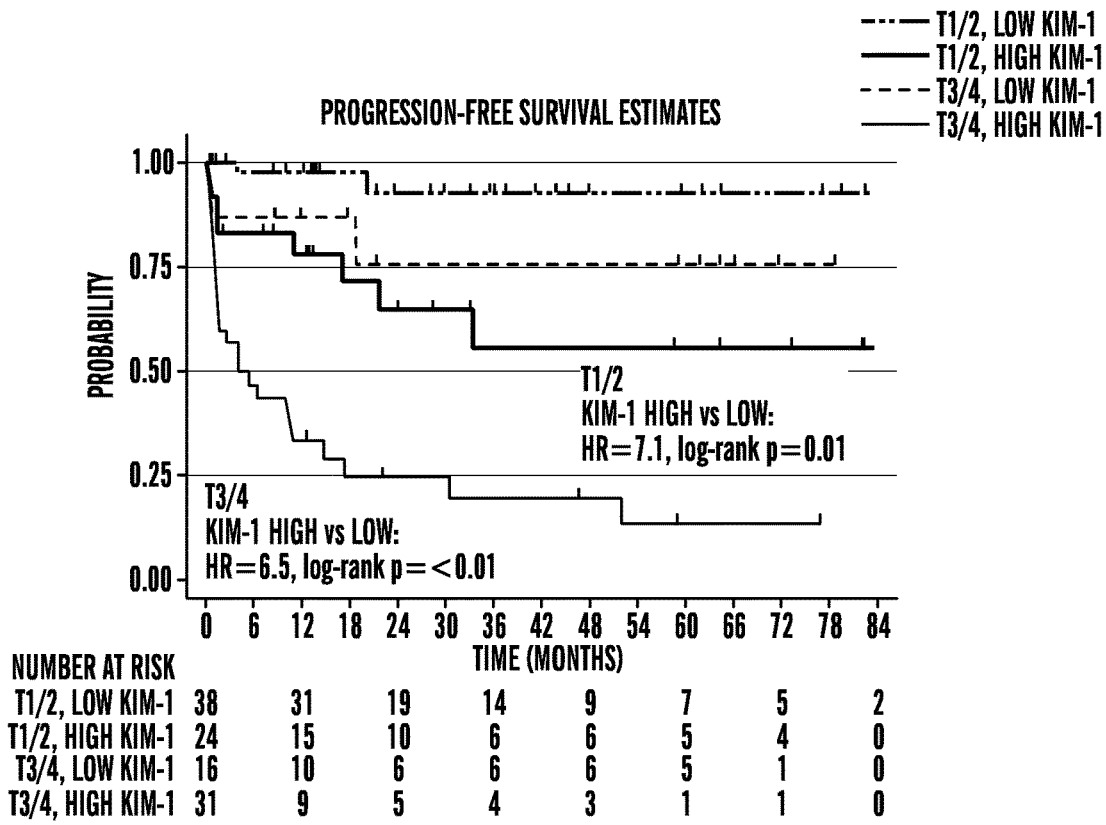
FIG. 7D subjects with T stage 1-2 or grade 3-4 RCC with higher plasma KIM-1 levels have a more severe progression as compared to subjects with the same T-stage of RCC but with lower plasma KIM-1 levels.
Figure 8:
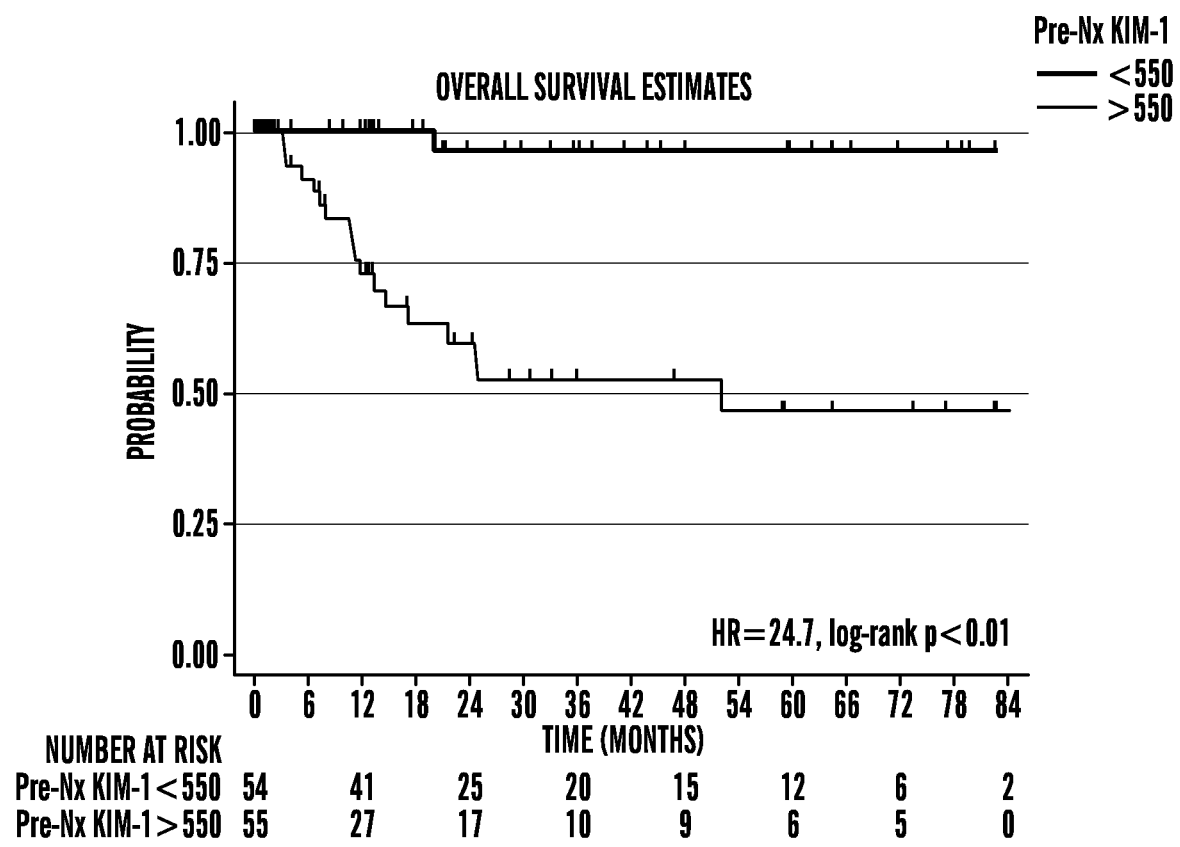
FIG. 8 shows elevated plasma KIM-1 is associated with overall survival with subjects with RCC. Kaplan-Meier survival curves show that high KIM-1 levels are associated with a decrease in overall survival compared to subjects with RCC with lower plasma KIM-1 levels, regardless of the tumor grade, metastasis status or T-stage.
Figure 9A:
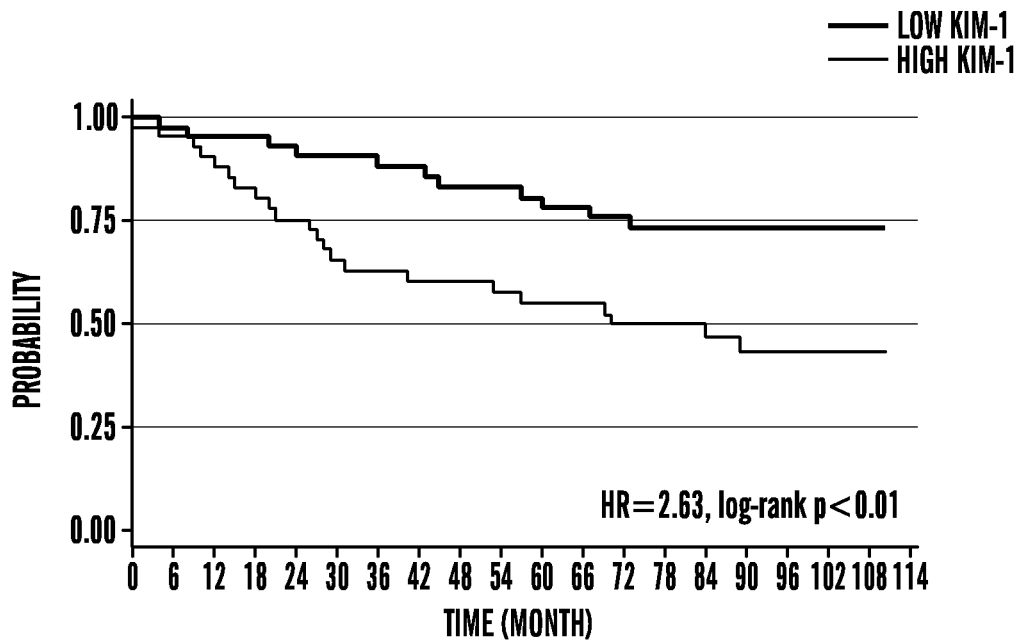
FIGS. 9A-9D show plasma KIM-1 is associated with disease progression and progression free survival (PFS) in the German cohort.
Figure 9B:
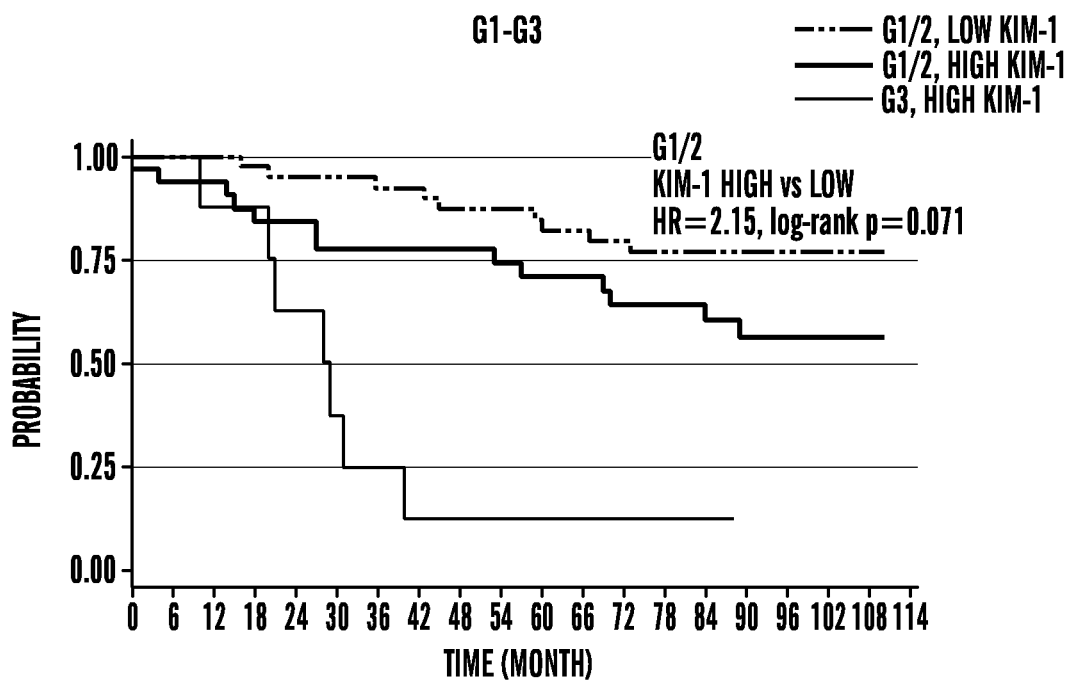
Figure 9C:
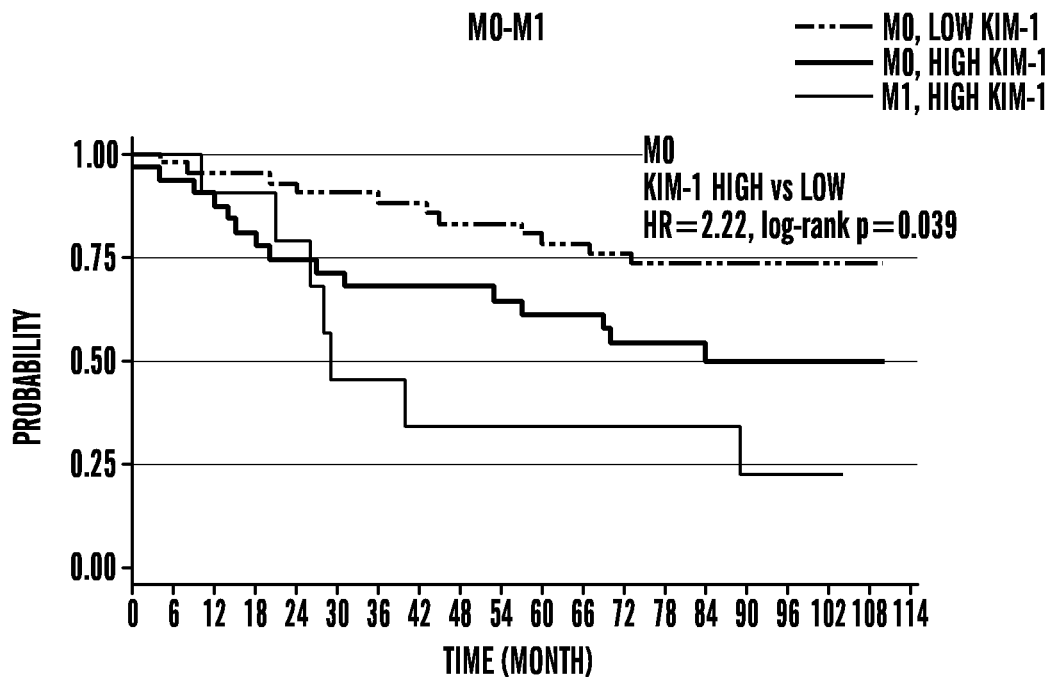
Figure 9D:
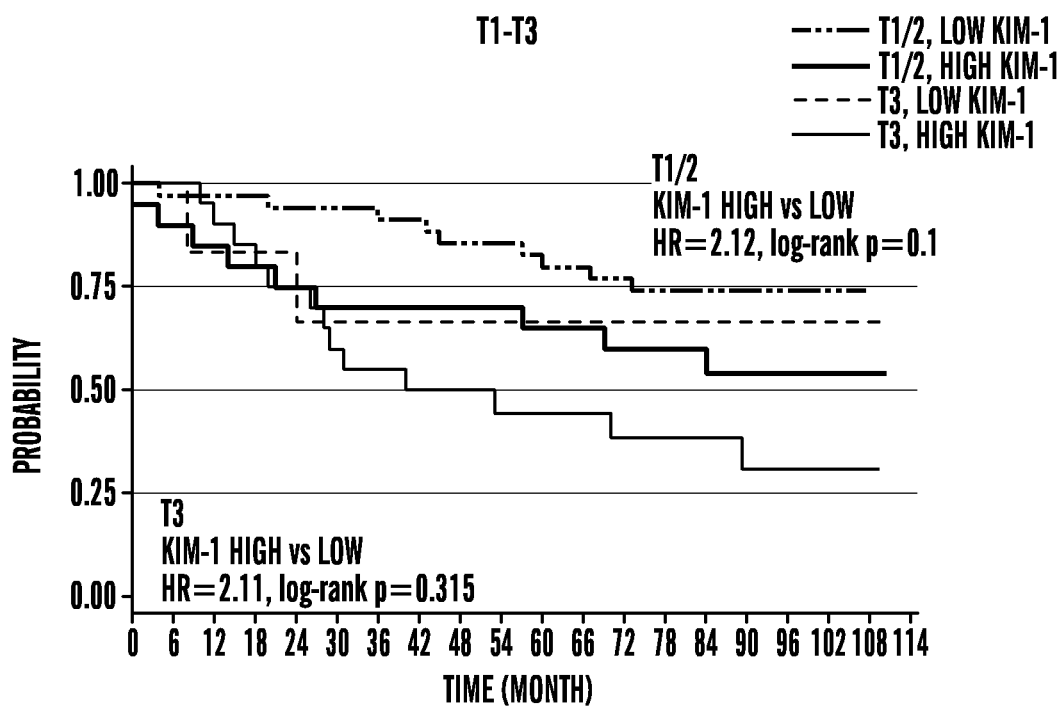
Figure 10A:
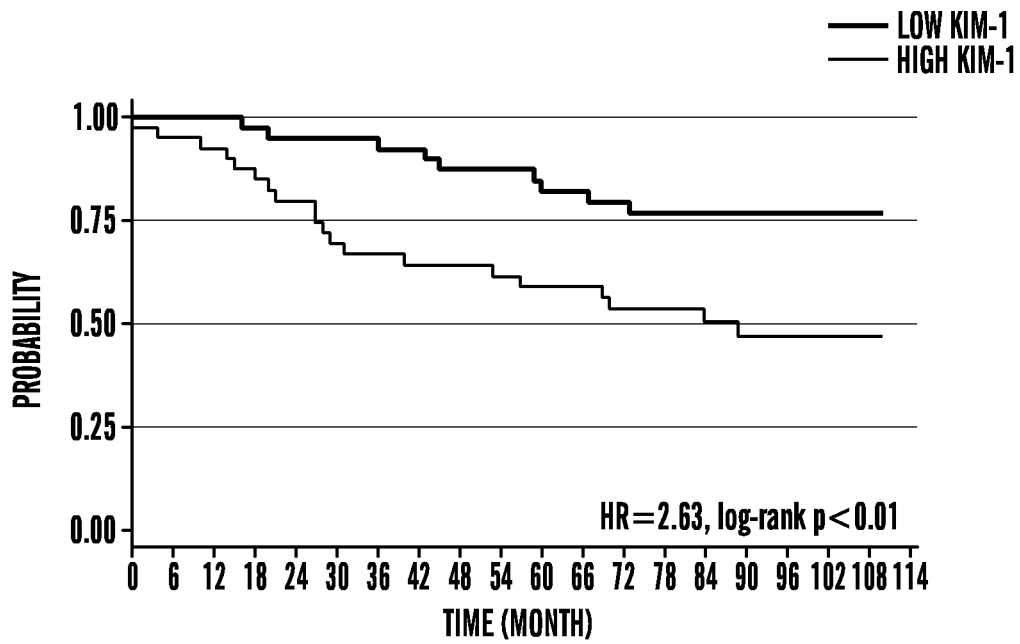
FIGS. 10A-10D show elevated plasma KIM-1 is associated with overall survival with subjects with RCC in the German Cohort subjects.
Figure 10B:
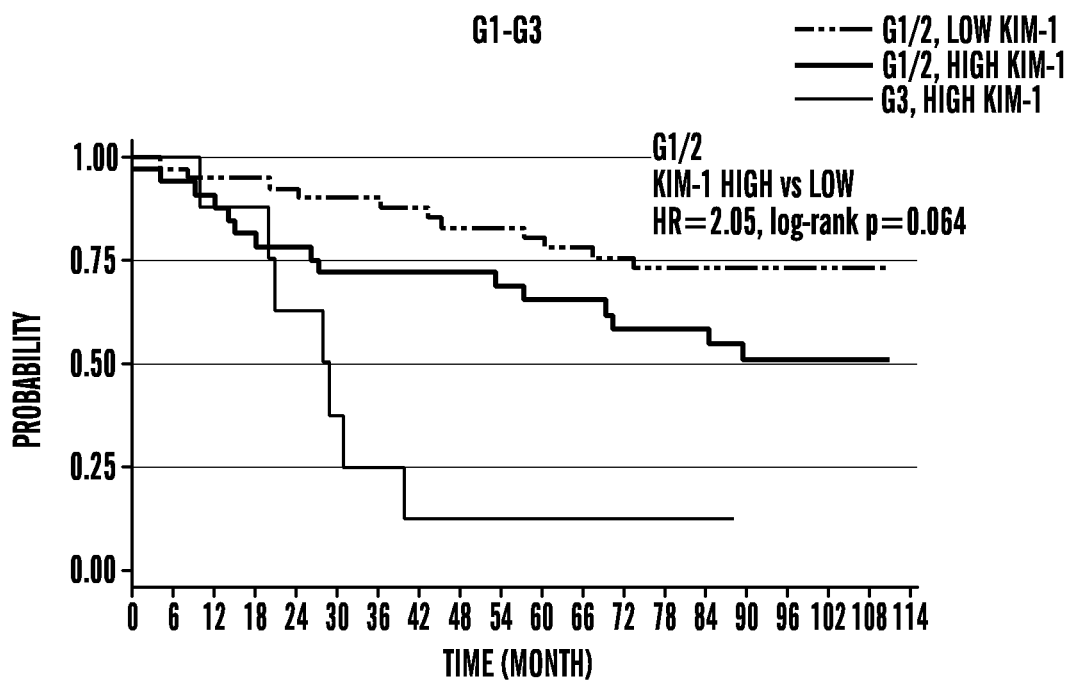
Figure 10C:
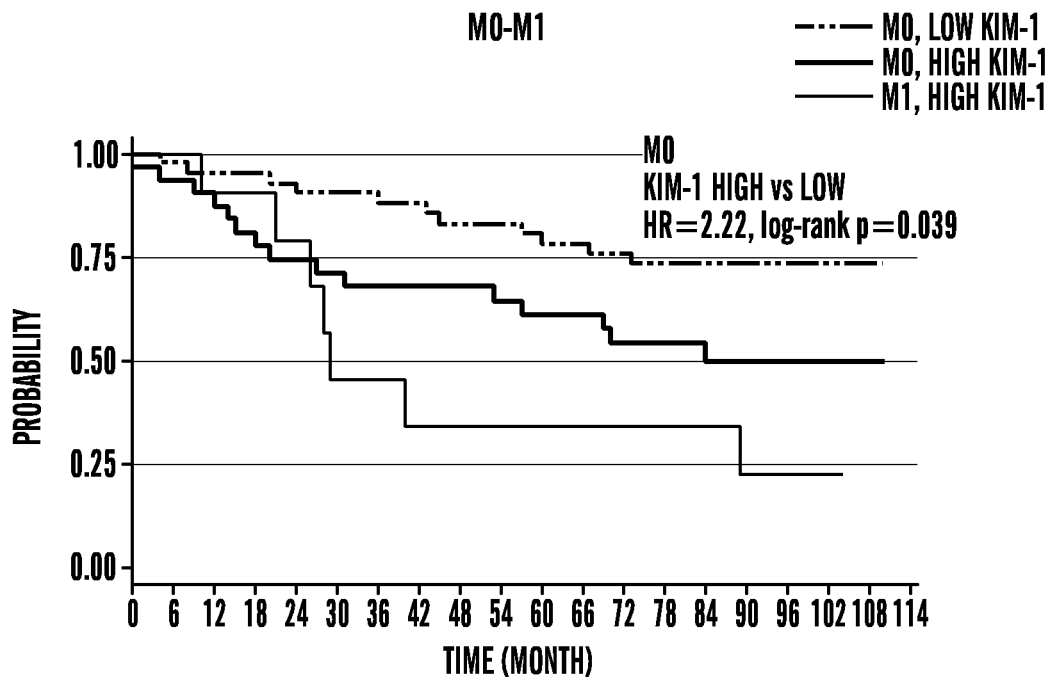
Figure 10D:
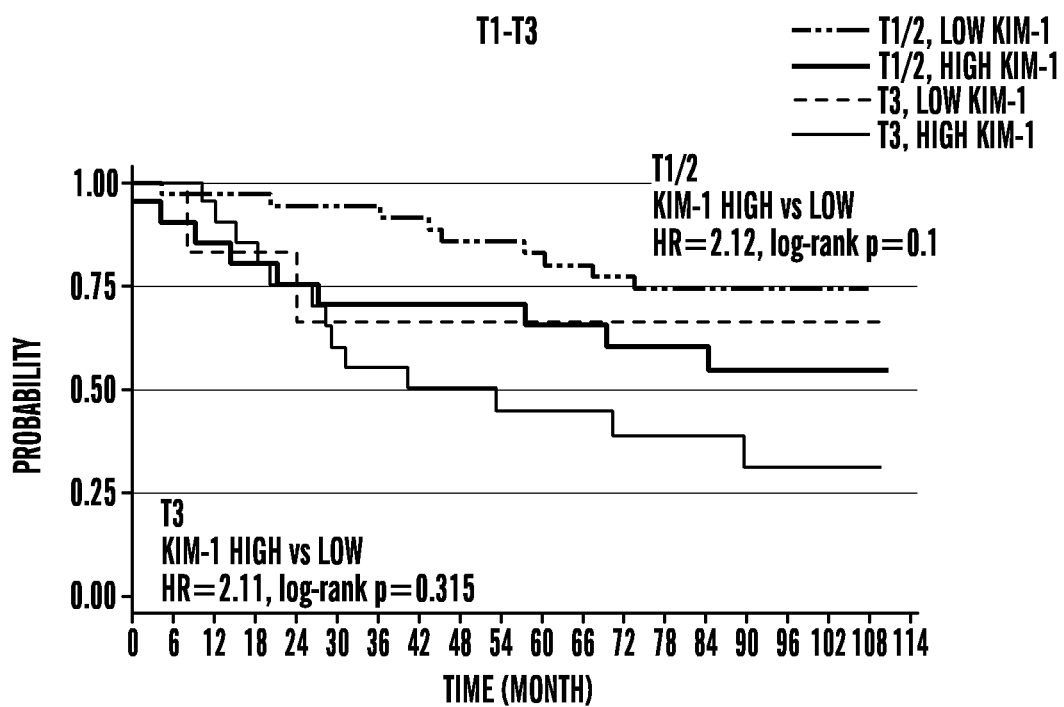
Figure 11A:
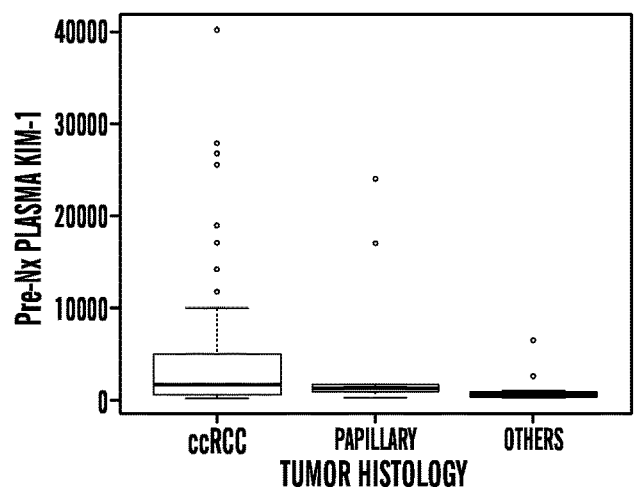
FIGS. 11A-11F plasma KIM levels are elevated in the clear cell papillary subtype of RCC and are associated with Clinicopathological parameters in RCC subjects from the German cohort.
Figure 11B:
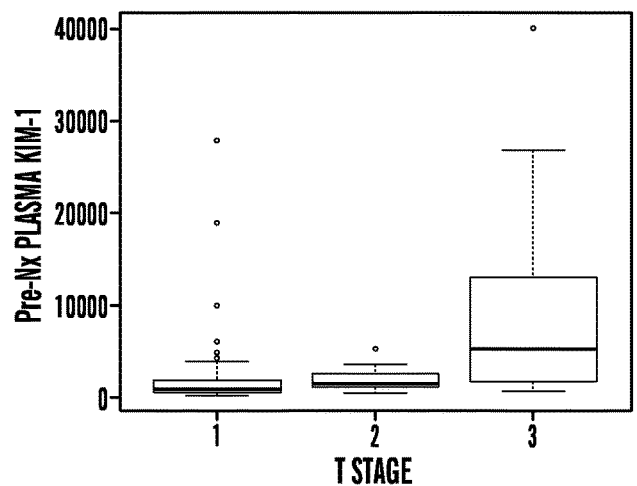
Figure 11C:
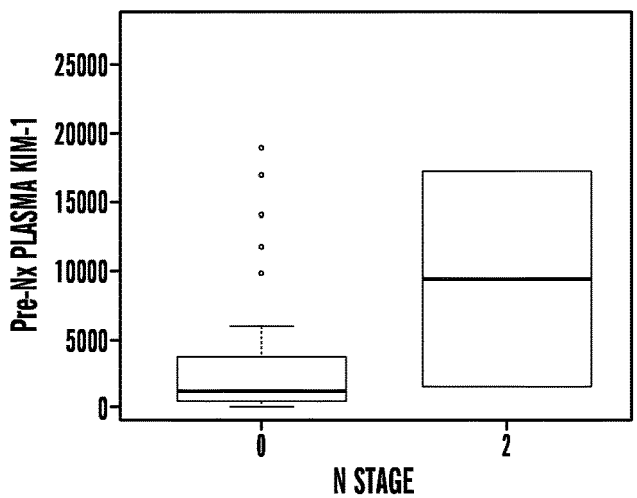
Figure 11D:
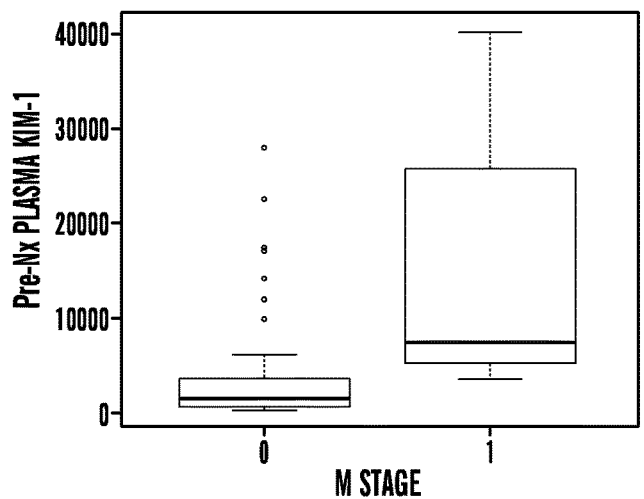
Figure 11E:
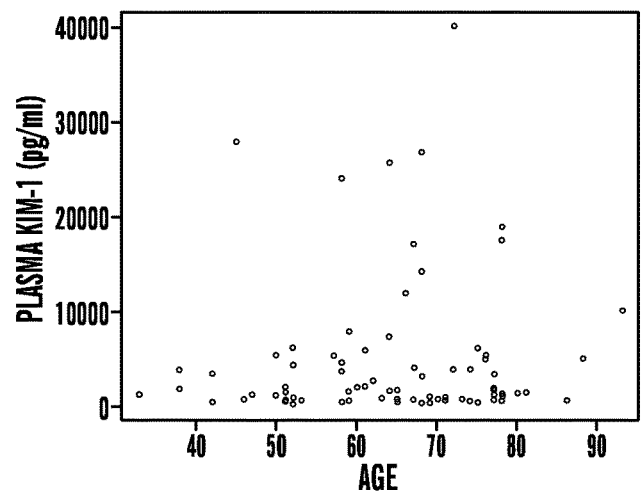
Figure 11F:
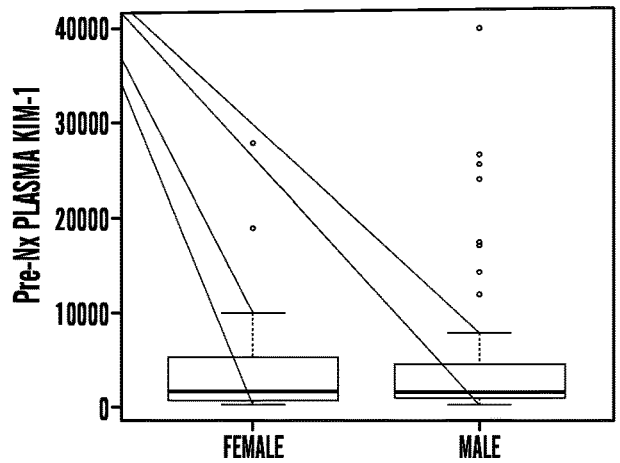
Figure 12:
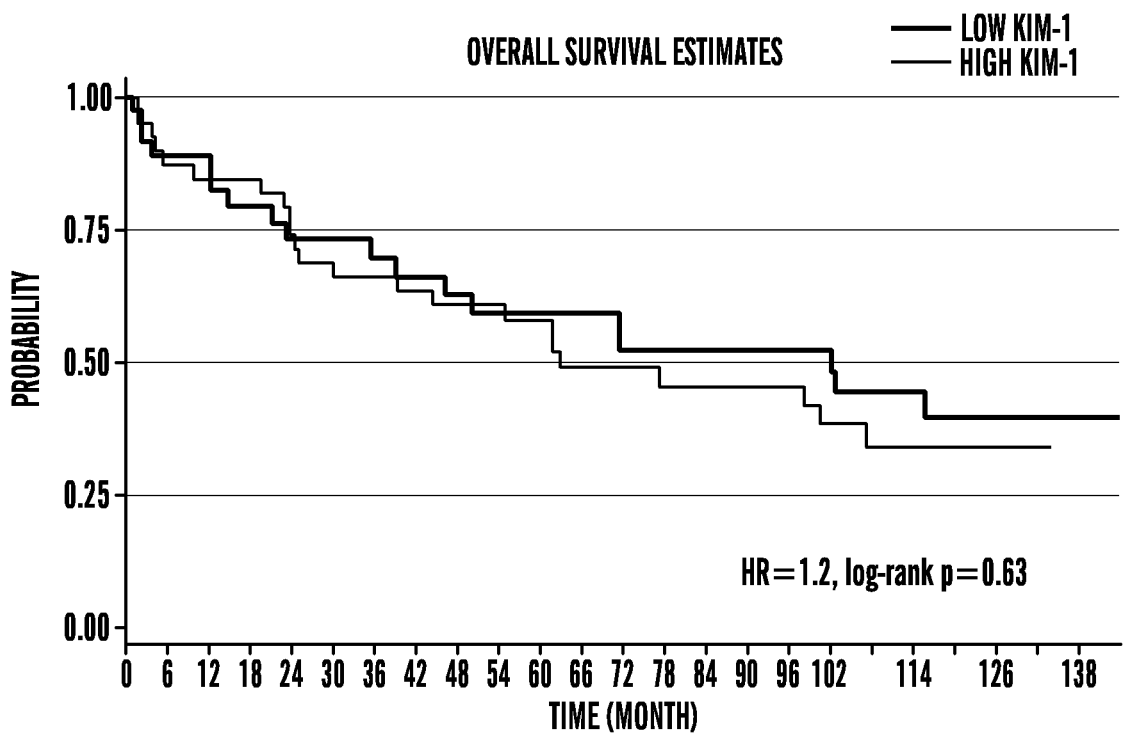
FIG. 12 shows elevated plasma KIM-1 levels is associated with a decrease in overall survival rate, as determined by the Kaplan-Meier survival curve.
Figure 13:
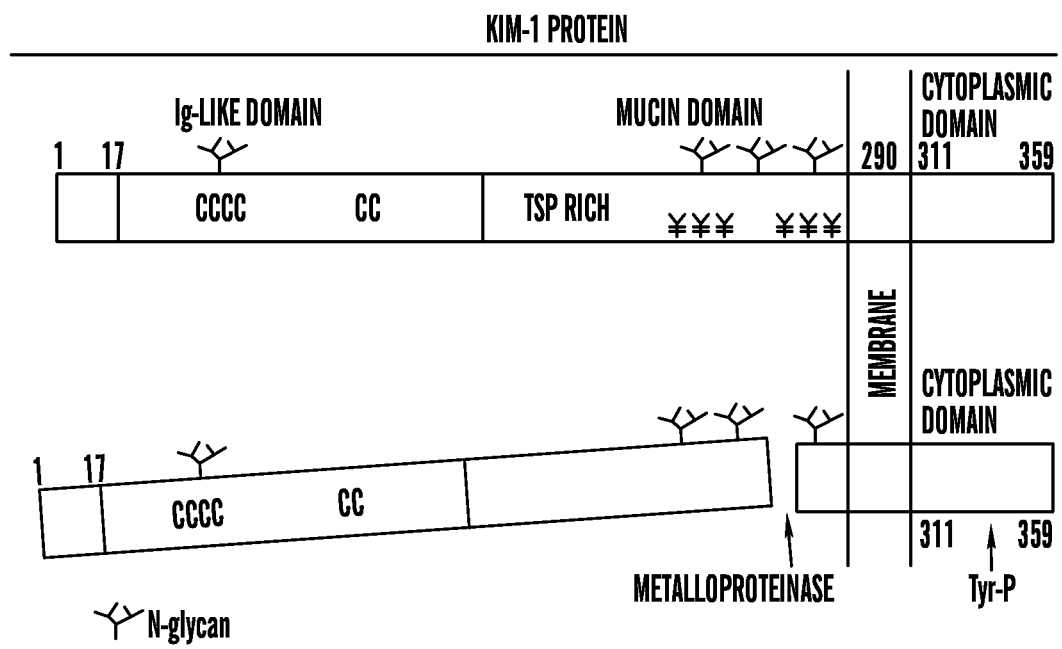
FIG. 13 depicts a schematic of the structure of KIM-1.

Herein, the inventors have also discovered that KIM-1 is present in the blood, e.g., KIM-1 is increased in plasma of subjects with ccRCC and papillary RCC, but not other types of RCC (e.g., chromophobe or oncocytoma (see FIG. 5A). As shown in FIGS. 6A-6B, and FIG. 11B-11D, increased levels of KIM-1 in the blood of subjects indicates a more severe tumor pathology (e.g., more severe tumor grade) as well as RCC metastasis. Although KIM-1 levels are increased in the urine in patients with ccRCC (Bonventre (2009), Nephrol Dial Transplant, 24; 3265-3268; Han W K et al., (2005) Human kidney injury molecule-1 is a tissue and urinary tumor marker of renal cell carcinoma. J Am Soc Nephrol; 16: 1126-1134). As demonstrated herein, KIM-1 is more reliable for general use in detecting metastases and over all burden of tumor mass since the KIM-1 ectodomain may not get adequately filtered by the glomeruli of the kidney due to the size of the polypeptide. Furthermore when the tumor is located in the kidney the architecture of the kidney is distorted and hence KIM-1 may not readily get into the collecting system of the kidney and excreted into the urine. Thus, it is highly surprising that it is released into the blood, as KIM-1 polypeptide is expressed by tubular epithelium kidney cells and it was previously believed that it was released only into the urine in subjects with RCC.

Importantly, the inventors demonstrate that elevated KIM-1 protein in the plasma of subjects indicates metastatic RCC (FIG. 6A, right panel and FIG. 11D), and that KIM-1 can be used as a biomarker for early RCC, before the subject has any symptoms of RCC. Additionally, in a long-term study, the inventors demonstrate subjects with a KIM-1 polypeptide level of at least 550 pg/ml have a more aggressive RCC and earlier onset of disease symptoms (FIGS. 7A-7D, and FIGS. 9A-9D), and a decreased survival time (FIGS. 8A and 10A-10D and FIG. 12).

Accordingly, another aspect of the present invention is directed to methods, kits and compositions for diagnosis of Renal Cell carcinoma (RCC), e.g., ccRCC in a subject by detecting levels of KIM-1 in the blood sample obtained from a subject. Accordingly, aspects of the present invention provides compositions and methods for the diagnosis and prognosis of renal cell carcinoma (RCC) using blood or plasma levels of KIM-1 as a diagnostic test that is sensitive and specific. Plasma KIM-1 levels is useful for diagnosis and/or assessment of prognosis of clear cell RCC in a subject.

Example 7

KIM-1 as a Biomarker for Kidney Infection

KIM-1 is produced and shed into the urine following proximal tubular kidney injury, and is not produced in the bladder. KIM-1 (and or its ectodomain) is increased in the urine of some patients with bladder infections because the infection has reached the upper urinary tract. In a patient with cystitis alone, not suffering from pyelonephritis, the level of KIM-1 in the plasma is not elevated. Conversely, the KIM-1 levels in the blood from a subject with cystitis have an elevated level of KIM-1 (and/or its ectodomain) as compared with control or reference plasma KIM-1 levels, and indicates that the patient may have pyelonephritis and needs a different clinical intervention. Therefore, the present invention also encompasses measuring KIM-1 polypeptide levels in the blood to facilitates the diagnosis and treatment of pyelonephritis in cystitis patients.

REFERENCES

The References cited in the specification and Examples are incorporated herein in their entirety.
1. Ichimura T, Bonventre J V, Bailly V, Wei H, Hession C A, Cate R L, Sanicola M: Kidney injury molecule-1 (KIM-1), a putative epithelial cell adhesion molecule containing a novel immunoglobulin domain, is up-regulated in renal cells after injury. *J Biol Chem* 273: 4135-4142,1998
2. Han W K, Bailly V, Abichandani R, Thadhani R, Bonventre J V: Kidney Injury Molecule-1 (KIM-1): a novel biomarker for human renal proximal tubule injury. *Kidney Int* 62: 237-244, 2002
3. Ichimura T, Hung C C, Yang S A, Stevens J L, Bonventre J V: Kidney injury molecule-1: a tissue and urinary biomarker for nephrotoxicant-induced renal injury. *Am J Physiol Renal Physiol* 286: F552F563, 2004

4. Vaidya V S, Ozer J S, Dieterle F, Collings F B, Ramirez V, Troth S, Muniappa N, Thudium D, Gerhold D, Holder D J, Bobadilla N A, Marrer E, Perentes E, Cordier A, Vonderscher J, Maurer G, Goering P L, Sistare F D, Bonventre J V: Kidney injury molecule-1 outperforms traditional biomarkers of kidney injury in preclinical biomarker qualification studies. *Nat Biotechnol* 28: 478-485, 2010
5. Vaidya V S, Waikar S S, Ferguson M A, Collings F B, Sunderland K, Gioules C, Bradwin G, Matsouaka R, Betensky R A, Curhan G C, Bonventre J V: Urinary biomarkers for sensitive and specific detection of acute kidney injury in humans. *Clin Transl Sci* 1: 200-208, 2008 van Timmeren M M, Bakker S J, Vaidya V S, Bailly V, Schuurs T A, Damman J, Stegeman C A, Bonventre J V, van Goor H: Tubular kidney injury molecule-1 in protein-overloadnephropathy. *Am J Physiol Renal Physiol* 291: F456-F464, 2006
7. Sabbisetti V S, Ito K, Wang C, Yang L, Mefferd S C, Bonventre J V: Novel assays for detection of urinary KIM-1 in mouse models of kidney injury. *Toxicol Sci* 131: 13-25, 2013
8. Dieterle F, Sistare F, Goodsaid F, Papaluca M, Ozer J S, Webb C P, Baer W, Senagore A, Schipper M J, Vonderscher J, Sultana S, Gerhold D L, Phillips J A, Maurer G, Carl K, Laurie D, Harpur E, Sonee M, Ennulat D, Holder D, Andrews-Cleavenger D, Gu Y Z, Thompson K L, Goering P L, Vidal J M, Abadie E, Maciulaitis R, Jacobson-Kram D, Defelice A F, Hausner E A, Blank M, Thompson A, Harlow P, Throckmorton D, Xiao S, Xu N, Taylor W, Vamvakas S, Flamion B, Lima B S, Kasper P, Pasanen M, Prasad K, Troth S, Bounous D, Robinson-Gravatt D, Betton G, Davis M A, Akunda J, McDuffie J E, Suter L, Obert L, Guffroy M, Pinches M, Jayadev S, Blomme E A, Beushausen S A, Barlow V G, Collins N, Waring J, Honor D, Snook S, Lee J, Rossi P, Walker E, Mattes W: Renal biomarker qualification submission: a dialog between the FDA-EMEA and Predictive Safety Testing Consortium. *Nat Biotechnol* 28: 455-462, 2010
9. U.S. Food and Drug Administration: FDA, European Medicines Agency to consider additional test results when assessing new drug safety: Collaborative effort by FDA and EMEA expected to yield additional safety data. 2008. Available at: http://www.fda.gov/NewsEvents/Newsroom/PressAnnouncements/2008/ucm116911.htm. Accessed Apr. 2, 2014
10. Myers B D, Chui F, Hilberman M, Michaels A S: Transtubular leakage of glomerular filtrate in human acute renal failure. *Am J Physiol* 237: F319-F325, 1979
11. Sutton T A: Alteration of microvascular permeability in acute kidney injury. *Microvasc Res* 77: 4-7, 2009
12. Sutton T A, Fisher C J, Molitoris B A: Micro-vascular endothelial injury and dysfunction during ischemic acute renal failure. *Kidney Int* 62: 1539-1549, 2002
13. KDIGO clinical practice guideline for acute kidney injury. *Kidney Int Suppl* 2: 1-138, 2012
14. Waikar S S, Betensky R A, Emerson S C, Bonventre J V: Imperfect gold standards for kidney injury biomarker evaluation. *J Am Soc Nephrol* 23: 13-21, 2012
15. Rosolowsky E T, Skupien J, Smiles A M, Niewczas M, Roshan B, Stanton R, Eckfeldt J H, Warram J H, Krolewski A S: Risk for ESRD in type 1 diabetes remains high despite re-noprotection. *J Am Soc Nephrol* 22: 545-553, 2011
16. Waikar S S, Sabbisetti V S, Bonventre J V: Normalization of urinary biomarkers to cre-atinine during changes in glomerular filtration rate. *Kidney Int* 78: 486-494, 2010
17. Feigelstock D, Thompson P, Mattoo P, Zhang Y, Kaplan G G: The human homolog of HAVcr-1 codes for a hepatitis A virus cellular receptor. *J Virol* 72: 6621-6628, 1998
18. Bonventre J V, Vaidya V S, Schmouder R, Feig P, Dieterle F: Next-generation biomarkers for detecting kidney toxicity. *Nat Biotechnol* 28: 436-440, 2010
19. Yang L, Besschetnova T Y, Brooks C R, Shah J V, Bonventre J V: Epithelial cell cycle arrest in G2/M mediates kidney fibrosis after injury. *Nat Med* 16: 535-543, 1p, 143, 2010
20. Humphreys B D, Xu F, Sabbisetti V, Grgic I, Naini S M, Wang N, Chen G, Xiao S, Patel D, Henderson J M, Ichimura T, Mou S, Soeung S, McMahon A P, Kuchroo V K, Bonventre J V: Chronic epithelial kidney injury molecule-1 expression causes murine kidney fibrosis. *J Clin Invest* 123: 4023-4035, 2013
21. Khosrotehrani K, Reyes R R, Johnson K L, Freeman R B, Salomon R N, Peter I, Stroh H, Guégan S, Bianchi D W: Fetal cells participate over time in the response to specific types of murine maternal hepatic injury. *Hum Reprod* 22: 654-661, 2007
22. Palevsky P M, Liu K D, Brophy P D, Chawla L S, Parikh C R, Thakar C V, Tolwani A J, Waikar S S, Weisbord S D: KDOQI US commentary on the 2012 KDIGO clinical practice guideline for acute kidney injury. *Am J Kidney Dis* 61: 649-672, 2013
23. Skupien J, Warram J H, Smiles A M, Niewczas M A, Gohda T, Pezzolesi M G, Cantarovich D, Stanton R, Krolewski A S: The early decline in renal function in patients with type 1 diabetes and proteinuria predicts the risk of end-stage renal disease. *Kidney Int* 82: 589-597, 2012
24. Vaidya V S, Waikar S S, Ferguson M A, Collings F B, Sunderland K, Gioules C, Bradwin G, Matsouaka R, Betensky R A, Curhan G C, Bonventre J V: Urinary biomarkers for sensitive and specific detection of acute kidney injury in humans. *Clin Transl Sci* 1: 200-208, 2008
25. Vaidya V S, Ramirez V, Ichimura T, Bobadilla N A, Bonventre J V: Urinary kidney injury molecule-1: a sensitive quantitative bio-marker for early detection of kidney tubular injury. *Am J Physiol Renal Physiol* 290: F517-F529, 2006
26. Grgic I, Campanholle G, Bijol V, Wang C, Sabbisetti V S, Ichimura T, Humphreys B D, Bonventre J V: Targeted proximal tubule injury triggers interstitial fibrosis and glomer-ulosclerosis. *Kidney Int* 82: 172-183, 2012
27. Hanley J A, McNeil B J: A method of comparing the areas under receiver operating characteristic curves derived from the same cases. *Radiology* 148: 839-843, 1983

SEQUENCE LISTING

```
SEQ ID NO: 1 KIM- polypeptide NCBI Ref Seq: NP_036338
    1   mhpqvvilsl ihladsvag svkvggeagp svtlpchysg avtsmcwnrg scslftcqng
   61   ivwtngthvt yrkdtrykll gdlsrrdvsl tientavsds gvyccrvehr gwfndmkitv
  121   sleivppkvt ttpivttvpt vttvrtsttv ptttvpmtt vptttvpttm siptttvlt
```

| | |
|---|---|
| 181 | tmtvstttsv ptttsipttt svpvtttvst fvppmplprq nhepvatsps spqpaethpt |
| 241 | tlqgairrep tssplysytt dgndtvtess dglwnnnqtq lflehsllta nttkgiyagv |
| 301 | cisvlvllal lgviiakkyf fkkevqqlsv sfsslqikal qnavekevqa edniyiensl |
| 361 | yatd |

SEQ ID NO: 2 KIM-1 mRNA sequence, variant 1 NCBI Ref Seq: NM_012206
| | |
|---|---|
| 1 | attctcctgc ctcagcctcc cgagtagctg ggactacagg cgccagtgac cacgcccggc |
| 61 | taatttttg tattttagt agagacgggg tttcacccti ttagccagga tggtctcgat |
| 121 | ctcctgactt cgtgatctgc ccgccttggc ctcccaaagt gctaggatta caggtttgag |
| 181 | ccaccgcgcc cggcccigtt tcctitttgt tgttccccl gataccctgt atcaggacca |
| 241 | ggagtcagtt tggcggttat gtgtggggaa gaagctggga agtcagggge tgtttctgtg |
| 301 | gacagctttc cctgtcctt ggaaggcaca gagctctcag ctgcagggaa ctaacagagc |
| 361 | tctgaagccg ttatatgtgg tcttctctca tttccagcag agcaggetca tatgaatcaa |
| 421 | ccaactgggt gaaaagataa gttgcaatct gagatttaag acttgatcag ataccatctg |
| 481 | gtggagggta ccaaccagce tgtctgctca ttttccttca ggetgatcce ataatgcatc |
| 541 | ctcaagtggt catcttaage ctcatcctac atctggcaga ttctgtagct ggttctgtaa |
| 601 | aggttggtgg agaggcaggt ccatctgtca cactaccctg ccactacagt ggagctgtca |
| 661 | catccatgtg ctggaataga ggctcatgtt ctctattcac atgccaaaat ggcattgtct |
| 721 | ggaccaatgg aacccacgtc acctatcgga aggacacacg ctataagcta ttggggggacc |
| 781 | tttcaagaag ggatgtctct ttgaccatag aaaatacagc tgtgtctgac agtggcgtat |
| 841 | attgttgccg tgttgagcac cgtgggtggt tcaatgacat gaaaatcacc gtatcattgg |
| 901 | agattgtgcc acccaaggtc acgactactc caattgtcac aactgttcca accgtcacga |
| 961 | ctgttcgaac gagcaccact gttccaacga caacgactgt tccaatgacg actgttccaa |
| 1021 | cgacaactgt tccaacaaca atgagcattc caacgacaac gactgttctg acgacaatga |
| 1081 | ctgtttcaac gacaacgagc gttccaacga caacgagcat tccaacaaca caagtgttc |
| 1141 | cagtgacaac aactgtctct acctttgttc ctccaatgcc tttgcccagg cagaaccatg |
| 1201 | aaccagtagc cacttcacca tcttcacctc agccagcaga aacccaccct acgacactgc |
| 1261 | agggagcaat aaggagagaa cccaccagct cacctattgta ctcttacaca acagatggga |
| 1321 | atgacaccgt gacagagtct tcagatggec tttggaataa caatcaaact caactgttcc |
| 1381 | tagaacatag tctactgacg gccaatacca ctaaaggaat ctatgctgga gtctgtatttt |
| 1441 | ctgtcttggt gcttctigct cttttgggtg tcatcattgc caaaaagtat ttcttcaaaa |
| 1501 | aggaggttca acaactaagt gtttcattta gcagccttca aattaaagct ttgcaaaatg |
| 1561 | cagttgaaaa ggaagtccaa gcagaagaca atatctacat tgaaaatagt ctttatgcca |
| 1621 | cggactaaga cccagtggtg ctctttgaga gtttacgccc atgagtgcag aagactgaac |
| 1681 | agacatcagc acatcagacg tcttttagac cccaagacaa ttttttctgtt tcagttttcat |
| 1741 | ctggcattcc aacatgtcag tgatactggg tagagtaact ctctcactcc aaactgtgta |
| 1801 | tagtcaacct catcattaat gtagtcctaa ttttttatgc t |

SEQ ID NO: 3 KIM-1 mRNA sequence, variant 2 NCBI Ref Seq: NM_0010994 14
| | |
|---|---|
| 1 | attctcctgc ctcagcctcc cgagtagctg ggactacagg cgccagtgac cacgcccggc |
| 61 | taatttttg tattttagt agagacgggg tttcacccti ttagccagga tggtctcgat |
| 121 | ctcctgactt cgtgatctgc ccgccttggc ctcccaaagt gctaggatta caggctgatc |
| 181 | ccataatgca tcctcaagtg gtcatcttaa gcctcatcct acatctggca gattctgtag |
| 241 | ctggttctgt aaaggttggt ggagaggcag gtccatctgt cacactaccc tgccactaca |
| 301 | gtggagctgt cacatccatg tgctggaata gaggetcatg ttctctattc acatgccaaa |
| 361 | atggcattgt ctggaccaat ggaacccacg tcacctatcg gaaggacaca cgctataagc |
| 421 | tatgggggga cctttcaaga agggatgtct ctttgaccat agaaaataca gctgtgtctg |
| 481 | acagtggcgt atattgttgc cgtgttgagc accgtgggtg gttcaatgac atgaaaatca |
| 541 | ccgtatcatt ggagattgtg ccacccaagg tcacgactac tccaattgtc acaactgttc |
| 601 | caaccgtcac gactgttcga acgagcacca ctgttccaac gacaacgact gttccaatga |
| 661 | cgactgttcc aacgacaact gttccaacaa caatgagcat tccaacgaca acgactgttc |
| 721 | tgacgacaat gactgtttca cgacaacga gcgttccaac gacaacgagc attccaacaa |
| 781 | caacaagtgt tccagtgaca acaactgtct tacctittgt tcctccaatg cctttgccca |
| 841 | ggcagaacca tgaaccagta gccacttcac catcttcacc tcagccagca gaaacccacc |
| 901 | ctacgacact gcagggagca ataaggagag aacccaccag ctcaccattg tactcttaca |
| 961 | caacagatgg gaatgacacc gtgacagagt cttcagatgg ccttttggaat aacaatcaaa |
| 1021 | ctcaactgtt cctagaacat agtctactga cggccaatac cactaaagga atctatgctg |
| 1081 | gagtctgtat ttctgtcttg gtgcttcttg ctcttttggg tgtcatcatt gccaaaaagt |
| 1141 | atttcttcaa aaaggaggtt caacaactaa gtgtttcatt tagcagcctt caaattaaag |
| 1201 | ctttgcaaaa tgcagttgaa aaggaagtcc aagcagaaga caatatctac attgagaata |
| 1261 | gtctttatgc cacggactaa gacccagtgg tgctctttga gagtttacgc ccatgagtgc |
| 1321 | agaagactga acagacatca gcacatcaga cgtcttttag accccaagac aattttttctg |
| 1381 | tttcagtttc atctggcatt ccaacatgtc agtgatactg ggtagagtaa ctctctcact |
| 1441 | ccaaactgtg tatagtcaac ctcatcatta atgtagtcct aatttttat gct |

SEQ ID NO: 4 KIM-1 mRNA sequence NCBI Ref Seq: NM_001173393
| | |
|---|---|
| 1 | gttacccagc attgtgagtg acagagcctg gatctgaacg ctgatcccat aatgcatcct |
| 61 | caagtggtca tcttaagcct catcctacat ctggcagatt ctgtagctgg ttctgtaaag |
| 121 | gttggtgag aggcaggtcc atctgtcaca ctaccctgcc actacagtgg agctgtcaca |
| 181 | tccatgtgct ggaatagagg ctcatgttct ctattcacat gccaaaatgg cattgtctgg |
| 241 | accaatggaa cccacgtcac ctatcggaag gacacacgct ataagctatt gggggacctt |
| 301 | tcaagaaggg atgtctcttt gaccatagaa aatacagctg tgtctgacag tggcgtatat |
| 361 | tgttgccgtg ttgagcaccg tgggtggttc aatgacatga aaatcaccgt atcattggat |
| 421 | attgtgccac ccaaggtcac gactactcca attgtcacaa ctgttccaac cgtcacgact |
| 481 | gttcgaacga gcaccactgt tccaacgaca acgactgttc aatgacgac tgttccaacg |
| 541 | acaactgttc caacaacaat gagcattcca acgacaacga ctgtctgac gacaatgact |
| 601 | gtttcaacga caacgagcgt tccaacgaca acgagcattc caacaacaac aagtgttcca |

SEQUENCE LISTING

```
  661   gtgacaacaa ctgtctctac ctttgttcct ccaatgcctt tgcccaggca gaaccatgaa
  721   ccagtagcca cttcaccatc ttcacctcag ccagcagaaa cccaccctac gacactgcag
  781   ggagcaataa ggagagaacc caccagctca ccattgtact cttacacaac agatgggaat
  841   gacaccgtga cagagtcttc agatggcctt tggaataaca atcaaactca actgttccta
  901   gaacatagtc tactgacggc caataccact aaaggaatct atgctggagt ctgtatttct
  961   gtcttggtgc ttcttgctct tttgggtgtc atcattgcca aaaagtattt cttcaaaaag
 1021   gaggttcaac aactaagtgt ttcatttagc agccttcaaa ttaaagcttt gcaaaatgca
 1081   gttgaaaagg aagtccaagc agaagacaat atctacattg agaatagtct ttatgccacg
 1141   gactaagacc cagtggtgct ctttgagagt ttacgcccat gagtgcagaa gactgaacag
 1201   acatcagcac atcagacgtc ttttagaccc caagacaatt tttctgtttc agtttcatct
 1261   ggcattccaa catgtcagtg atactgggta gagtaactct ctcactccaa actgtgtata
 1321   gtcaacctca tcattaatgt agtcctaatt tttatgct
```

SEQ ID NO: 5 SSDGLWNNNQTQLFLEHS

SEQ ID NO: 6: The ectodomain of KIM-1 (amino acids 1-295 of SEQ ID NO: 1)
mhpqvvilsl ilhladsvag svkvggeagp svtlpchysg avtsmcwnrg scslftcqng
ivwtngthvt yrkdtrykll gdlsrrdvsl tientavsds gvyccrvehr gwfndmkitv
sleivppkvt ttpivttvpt vttvrtsttv pttttvpmtt vptttvpttm sipttttvlt
tmtvstttsv ptttsipttt svpvtttvst fvppmplprq nhepvatsps spqpaethpt
tlqgairrep tssplysytt dgndtvtess dglwnnnqtq lflehsllta nttkg

---

The invention claimed is:

1. An assay for diagnosing kidney injury or Renal Cell Carcinoma (RCC) in a subject and treating the subject, consisting essentially of:
   a. contacting a blood sample obtained from a subject identified to have, or at risk of having a kidney injury, with an anti-KIM-1 antibody that specifically binds to a KIM-1 polypeptide of (SEQ ID NO: 1), and measuring the binding between the KIM-1 polypeptide and the anti-KIM-1 antibody;
   b. comparing the level of the KIM-1 polypeptide in the blood sample with a reference level of the KIM-1 polypeptide;
   c. selecting the subject as having a kidney injury or Renal Cell Carcinoma (RCC) when the level of KIM-1 polypeptide in the blood sample is 4-fold higher, or greater than 4-fold higher than the reference level for the KIM-1 polypeptide; and
   d. administering an effective treatment for treating kidney disease to the subject selected as being diagnosed with a kidney injury or RCC.

2. The assay of claim 1, wherein the kidney injury is selected from the group consisting of: injury to the proximal tubule of the kidney; acute kidney injury (AKI); chronic kidney disease (CKD); early kidney injury which will progress into chronic kidney disease (CKD).

3. The assay of claim 1, wherein the blood sample is obtained from a subject selected from the group consisting of: a subject suspected to have a kidney disease, a subject who has undergone a cardiopulmonary bypass (CBP), a subject who has type-1 diabetes, a subject who has diabetic nephrology.

4. The assay of claim 1, wherein the subject is diagnosed with a risk of developing end stage renal disease (ESRD) within 10 years when the level of KIM-1 polypeptide detected in the blood is at least 5-fold above the reference level.

5. The assay of claim 1, wherein the anti-KIM-1 antibody is a polyclonal antibody, a chimeric antibody, an Fab antigen-binding fragment thereof, fragment, an F(ab')2 antigen-binding fragment thereof, an Fab 'antigen-binding fragment thereof, an F sc antigen-binding fragment thereof, or an Fv antigen-binding fragment thereof.

6. The assay of claim 1, wherein the agent anti-KIM-1 antibody is immobilized on, or attached to, the surface of a solid support.

7. The assay of claim 6, wherein the solid support surface is in the format of a dipstick, a test strip, paper-based assay, a latex bead, a microsphere, or a multi-well plate.

8. The assay of claim 1, wherein the anti-KIM-1 antibody comprises a detectable label, or can be bound by a secondary agent which comprises a detectable label.

9. The assay of claim 1, wherein the assay is an immunoassay selected from the group consisting of: an ELISA assay, multiplex bead assay, dipstick assay, Western blot analysis, radioimmunoassay (RIA), Immunoradiometric assay (IRMA), chemiluminescent immunoassays, a fluorescence antibody method, passive haemagglutination.

10. The assay of claim 1, wherein the blood sample is selected from the group consisting of; a whole blood sample a plasma sample, a serum sample or a fractionated blood sample.

11. A method for assessing the severity of kidney injury in a subject and treating the subject, consisting essentially of:
   a. detecting whether human kidney injury molecule-1 (KIM-1) polypeptide is present in a first blood sample obtained from the subject at a first timepoint, by contacting the first blood sample with an anti-KIM-1 antibody which specifically binds to a KIM-1 polypeptide (SEQ ID NO: 1), and detecting binding between the KIM-1 polypeptide and the anti-KIM-1 antibody;
   b. detecting whether human KIM-1 polypeptide is present in a second blood sample obtained from the subject at a second timepoint, by contacting the second blood sample with an anti-KIM-1 antibody and detecting binding between the KIM-1 polypeptide and the anti-KIM-1 antibody, wherein the second timepoint is later than the first timepoint;
   c. selecting the subject as being diagnosed with having a more severe kidney injury at the second timepoint as compared to the first timepoint when the level of KIM-1 polypeptide detected in the second blood sample is above the level of KIM-1 polypeptide detected in the first blood sample obtained at the first timepoint, wherein the level of KIM-1 polypeptide in the first blood sample obtained at a first timepoint is at least 4-fold higher than a reference blood KIM-1 polypeptide level; or
   d. selecting the subject as being diagnosed with having a less severe kidney injury at the second timepoint as compared to the first timepoint when the level of KIM-1 polypeptide detected in the second blood sample obtained at the second timepoint is below the level of KIM-1 polypeptide detected in the first blood sample obtained at the first timepoint, wherein the level of KIM-1 polypeptide in the first blood sample obtained at a first timepoint is at least 4-fold higher than a reference blood KIM-1 polypeptide level; and
   e. administering an appropriate treatment for kidney disease to the subject diagnosed to have a more severe kidney injury at the second timepoint.

12. The method of claim 11, further comprising administering an appropriate therapeutic agent for treating kidney injury or RCC to the subject between the first timepoint and second timepoint, and determining the therapeutic agent to be effective when the level of the KIM-1 polypeptide detected in the second blood sample obtained at the second timepoint is significantly lower than the level of the KIM-1 polypeptide detected in the first blood sample obtained at the first timepoint.

13. The method of claim 11, wherein the first blood sample and second blood sample are the same type and selected from the group consisting of: whole blood, plasma, serum or fractionated blood.

14. The method of claim 11, wherein the kidney injury selected from the group consisting of: injury to the proximal tubule of the kidney; acute kidney injury (AKI); chronic kidney disease (CKD); early kidney injury which will progress into chronic kidney disease (CKD).

15. The method of claim 11, wherein the anti-KIM-1 antibody is selected from an antibody fragment, or antigen-binding fragment of an antibody, or a protein-binding molecule.

16. The method of claim 15, wherein the anti-KIM-1 antibody is a polyclonal antibody, a chimeric antibody, an Fab antigen-binding fragment thereof, an F(ab')2 antigen-binding fragment thereof, an Fab antigen-binding fragment thereof, an F sc antigen-binding fragment thereof, or an Fv antigen-binding fragment thereof.

17. The method of claim 11, wherein the anti-KIM-1 antibody is immobilized on, or attached to, the surface of a solid support.

18. The method of claim 11, wherein the anti-KIM-1 antibody agent comprises a detectable label, or wherein the agent can be bound by a secondary agent which comprises a detectable label.

19. The method of claim 11, wherein the anti-KIM-1 antibody can be detected using an immunoassay selected from the group consisting of: an ELISA assay, multiplex assay (IRMA), chemiluminescent immunoassays, a fluorescence antibody method, passive haemagglutination.

* * * * *

SEQUENCE LISTING

<160> NUMBER OF SEQ ID NOS: 7

<210> SEQ ID NO 1
<211> LENGTH: 364
<212> TYPE: PRT
<213> ORGANISM: Homo sapiens

<400> SEQUENCE: 1

```
Met His Pro Gln Val Val Ile Leu Ser Leu Ile Leu His Leu Ala Asp
1               5                  10                  15

Ser Val Ala Gly Ser Val Lys Val Gly Gly Glu Ala Gly Pro Ser Val
            20                  25                  30

Thr Leu Pro Cys His Tyr Ser Gly Ala Val Thr Ser Met Cys Trp Asn
        35                  40                  45

Arg Gly Ser Cys Ser Leu Phe Thr Cys Gln Asn Gly Ile Val Trp Thr
    50                  55                  60

Asn Gly Thr His Val Thr Tyr Arg Lys Asp Thr Arg Tyr Lys Leu Leu
65                  70                  75                  80

Gly Asp Leu Ser Arg Arg Asp Val Ser Leu Thr Ile Glu Asn Thr Ala
                85                  90                  95

Val Ser Asp Ser Gly Val Tyr Cys Cys Arg Val Glu His Arg Gly Trp
            100                 105                 110

Phe Asn Asp Met Lys Ile Thr Val Ser Leu Glu Ile Val Pro Pro Lys
        115                 120                 125

Val Thr Thr Thr Pro Ile Val Thr Thr Val Pro Thr Val Thr Thr Val
    130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                165                 170                 175

Thr Val Leu Thr Thr Met Thr Val Ser Thr Thr Thr Ser Val Pro Thr
            180                 185                 190

Thr Thr Ser Ile Pro Thr Thr Thr Ser Val Pro Val Thr Thr Thr Val
        195                 200                 205

Ser Thr Phe Val Pro Pro Met Pro Leu Pro Arg Gln Asn His Glu Pro
```

```
                     210                 215                 220
Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                245                 250                 255

Ser Tyr Thr Thr Asp Gly Asn Asp Thr Val Thr Glu Ser Ser Asp Gly
                260                 265                 270

Leu Trp Asn Asn Asn Gln Thr Gln Leu Phe Leu Glu His Ser Leu Leu
            275                 280                 285

Thr Ala Asn Thr Thr Lys Gly Ile Tyr Ala Gly Val Cys Ile Ser Val
        290                 295                 300

Leu Val Leu Leu Ala Leu Leu Gly Val Ile Ile Ala Lys Lys Tyr Phe
305                 310                 315                 320

Phe Lys Lys Glu Val Gln Gln Leu Ser Val Ser Phe Ser Ser Leu Gln
                325                 330                 335

Ile Lys Ala Leu Gln Asn Ala Val Glu Lys Glu Val Gln Ala Glu Asp
                340                 345                 350

Asn Ile Tyr Ile Glu Asn Ser Leu Tyr Ala Thr Asp
            355                 360

<210> SEQ ID NO 2
<211> LENGTH: 1841
<212> TYPE: DNA
<213> ORGANISM: Homo sapiens

<400> SEQUENCE: 2
attctcctgc ctcagcctcc cgagtagctg ggactacagg cgccagtgac cacgcccggc     60 taatttttg tattttagt agagacgggg tttcacccct ttagccagga tggtctcgat      120
ctcctgactt cgtgatctgc cgccttggc ctcccaaagt gctaggatta caggtttgag     180
ccaccgcgcc cggccctgtt ccttttgt ttgttcccct gatacccgt atcaggacca       240 ggagtcagtt tggcggttat gtgtggggaa gaagctggga agtcaggggc tgtttctgtg    300
gacagctttc cctgtccttt ggaaggcaca gagctctcag ctgcagggaa ctaacagagc    360
tctgaagccg ttatatgtgg tcttctctca tttccagcag agcaggctca tatgaatcaa    420
ccaactgggt gaaaagataa gttgcaatct gagatttaag acttgatcag ataccatctg    480
gtggagggta ccaaccagcc tgtctgctca ttttccttca ggctgatccc ataatgcatc    540
ctcaagtggt catcttaagc ctcatcctac atctggcaga ttctgtagct ggttctgtaa    600
aggttggtgg agaggcaggt ccatctgtca cactaccctg ccactacagt ggagctgtca    660
catccatgtg ctggaataga ggctcatgtt ctctattcac atgccaaaat ggcattgtct    720
ggaccaatgg aacccacgtc acctatcgga aggacacacg ctataagcta ttggggacc    780 tttcaagaag ggatgtctct ttgaccatag aaaatacagc tgtgtctgac agtggcgtat    840
attgttgccg tgttgagcac cgtgggtggt tcaatgacat gaaaatcacc gtatcattgg    900
agattgtgcc acccaaggtc acgactactc caattgtcac aactgttcca accgtcacga    960
ctgttcgaac gagcaccact gttccaacga caacgactgt tccaatgacg actgttccaa   1020
cgacaactgt tccaacaaca atgagcattc aacgacaaca gactgttctg acgacaatga   1080
ctgtttcaac gacaacgagc gttccaacga acgagcat tccaacaaca caagtgttc     1140 cagtgacaac aactgtctct acctttgttc ctccaatgcc tttgcccagg cagaaccatg   1200
aaccagtagc cacttcacca tcttcacctc agccagcaga acccaccct acgacactgc    1260
```

| | | | | |
|---|---|---|---|---|
| agggagcaat | aaggagagaa | cccaccagct | caccattgta | ctcttacaca acagatggga | 1320 |
| atgacaccgt | gacagagtct | tcagatggcc | tttggaataa | caatcaaact caactgttcc | 1380 |
| tagaacatag | tctactgacg | gccaatacca | ctaaaggaat | ctatgctgga gtctgtattt | 1440 |
| ctgtcttggt | gcttcttgct | cttttgggtg | tcatcattgc | caaaaagtat ttcttcaaaa | 1500 |
| aggaggttca | acaactaagt | gtttcattta | gcagccttca | aattaaagct ttgcaaaatg | 1560 |
| cagttgaaaa | ggaagtccaa | gcagaagaca | atatctacat | tgagaatagt ctttatgcca | 1620 |
| cggactaaga | cccagtggtg | ctctttgaga | gtttacgccc | atgagtgcag aagactgaac | 1680 |
| agacatcagc | acatcagacg | tcttttagac | cccaagacaa | ttttttctgtt tcagtttcat | 1740 |
| ctggcattcc | aacatgtcag | tgatactggg | tagagtaact | ctctcactcc aaactgtgta | 1800 |
| tagtcaacct | catcattaat | gtagtcctaa | ttttttatgc | t | 1841 |

<210> SEQ ID NO 3
<211> LENGTH: 1493
<212> TYPE: DNA
<213> ORGANISM: Homo sapiens

<400> SEQUENCE: 3

| | | | | |
|---|---|---|---|---|
| attctcctgc | ctcagcctcc | cgagtagctg | ggactacagg | cgccagtgac cacgcccggc | 60 |
| taattttttg | tatttttagt | agagacgggg | tttcaccctt | ttagccagga tggtctcgat | 120 |
| ctcctgactt | cgtgatctgc | ccgccttggc | ctcccaaagt | gctaggatta caggctgatc | 180 |
| ccataatgca | tcctcaagtg | gtcatcttaa | gcctcatcct | acatctggca gattctgtag | 240 |
| ctggttctgt | aaaggttggt | ggagaggcag | gtccatctgt | cacactaccc tgccactaca | 300 |
| gtggagctgt | cacatccatg | tgctggaata | gaggctcatg | ttctctattc acatgccaaa | 360 |
| atggcattgt | ctggaccaat | ggaacccacg | tcacctatcg | gaaggacaca cgctataagc | 420 |
| tattggggga | cctttcaaga | agggatgtct | ctttgaccat | agaaaataca gctgtgtctg | 480 |
| acagtggcgt | atattgttgc | cgtgttgagc | accgtgggtg | gttcaatgac atgaaaatca | 540 |
| ccgtatcatt | ggagattgtg | ccacccaagg | tcacgactac | tccaattgtc acaactgttc | 600 |
| caaccgtcac | gactgttcga | acgagcacca | ctgttccaac | gacaacgact gttccaatga | 660 |
| cgactgttcc | aacgacaact | gttccaacaa | caatgagcat | tccaacgaca acgactgttc | 720 |
| tgacgacaat | gactgtttca | acgacaacga | gcgttccaac | gacaacgagc attccaacaa | 780 |
| caacaagtgt | tccagtgaca | caactgtcct | ctacctttgt | tcctccaatg cctttgccca | 840 |
| ggcagaacca | tgaaccagta | gccacttcac | catcttcacc | tcagccagca gaaacccacc | 900 |
| ctacgacact | gcagggagca | ataaggagag | aacccaccag | ctcaccattg tactcttaca | 960 |
| caacagatgg | gaatgacacc | gtgacagagt | cttcagatgg | cctttggaat aacaatcaaa | 1020 |
| ctcaactgtt | cctagaacat | agtctactga | cggccaatac | cactaaagga atctatgctg | 1080 |
| gagtctgtat | ttctgtcttg | gtgcttcttg | ctcttttggg | tgtcatcatt gccaaaaagt | 1140 |
| atttcttcaa | aaaggaggtt | caacaactaa | gtgtttcatt | tagcagcctt caaattaaag | 1200 |
| ctttgcaaaa | tgcagttgaa | aaggaagtcc | aagcagaaga | caatatctac attgagaata | 1260 |
| gtctttatgc | cacggactaa | gacccagtgg | tgctctttga | gagtttacgc ccatgagtgc | 1320 |
| agaagactga | acagacatca | gcacatcaga | cgtcttttag | accccaagac aattttttctg | 1380 |
| tttcagtttc | atctggcatt | ccaacatgtc | agtgatactg | ggtagagtaa ctctctcact | 1440 |
| ccaaactgtg | tatagtcaac | ctcatcatta | atgtagtcct | aatttttttat gct | 1493 |

<210> SEQ ID NO 4
<211> LENGTH: 1359
<212> TYPE: DNA
<213> ORGANISM: Homo sapiens

<400> SEQUENCE: 4

```
gttacccagc attgtgagtg acagagcctg gatctgaacg ctgatcccat aatgcatcct      60
caagtggtca tcttaagcct catcctacat ctggcagatt ctgtagctgg ttctgtaaag     120
gttggtggag aggcaggtcc atctgtcaca ctaccctgcc actacagtgg agctgtcaca     180
tccatgtgct ggaatagagg ctcatgttct ctattcacat gccaaaatgg cattgtctgg     240
accaatggaa cccacgtcac ctatcggaag gacacacgct ataagctatt gggggacctt     300
tcaagaaggg atgtctcttt gaccatagaa atacagctg tgtctgacag tggcgtatat      360
tgttgccgtg ttgagcaccg tgggtggttc aatgacatga aaatcaccgt atcattggag     420
attgtgccac ccaaggtcac gactactcca attgtcacaa ctgttccaac cgtcacgact     480
gttcgaacga gcaccactgt tccaacgaca acgactgttc caatgacgac tgttccaacg     540
acaactgttc caacaacaat gagcattcca acgacaacga ctgttctgac gacaatgact     600
gtttcaacga caacgagcgt tccaacgaca acgagcattc caacaacaac aagtgttcca     660
gtgacaacaa ctgtctctac ctttgttcct ccaatgcctt tgcccaggca gaaccatgaa     720
ccagtagcca cttcaccatc ttcacctcag ccagcagaaa cccaccctac gacactgcag     780
ggagcaataa ggagagaacc caccagctca ccattgtact cttacacaac agatgggaat     840
gacaccgtga cagagtcttc agatggcctt tggaataaca atcaaactca actgttccta     900
gaacatagtc tactgacggc caataccact aaaggaatct atgctggagt ctgtatttct     960
gtcttggtgc ttcttgctct tttgggtgtc atcattgcca aaaagtattt cttcaaaaag    1020
gaggttcaac aactaagtgt tcatttagc agccttcaaa ttaaagcttt gcaaaatgca    1080
gttgaaaagg aagtccaagc agaagacaat atctacattg agaatagtct ttatgccacg    1140
gactaagacc cagtggtgct ctttgagagt ttacgcccat gagtgcagaa gactgaacag    1200
acatcagcac atcagacgtc ttttagaccc caagacaatt tttctgtttc agtttcatct    1260
ggcattccaa catgtcagtg atactgggta gagtaactct ctcactccaa actgtgtata    1320
gtcaacctca tcattaatgt agtcctaatt ttttatgct                           1359
```

<210> SEQ ID NO 5
<211> LENGTH: 18
<212> TYPE: PRT
<213> ORGANISM: Homo sapiens

<400> SEQUENCE: 5

Ser Ser Asp Gly Leu Trp Asn Asn Asn Gln Thr Gln Leu Phe Leu Glu
1               5                   10                  15

His Ser

<210> SEQ ID NO 6
<211> LENGTH: 295
<212> TYPE: PRT
<213> ORGANISM: Homo sapiens

<400> SEQUENCE: 6

Met His Pro Gln Val Val Ile Leu Ser Leu Ile Leu His Leu Ala Asp
1               5                   10                  15

Ser Val Ala Gly Ser Val Lys Val Gly Gly Glu Ala Gly Pro Ser Val
            20                  25                  30

```
Thr Leu Pro Cys His Tyr Ser Gly Ala Val Thr Ser Met Cys Trp Asn
         35                  40                  45

Arg Gly Ser Cys Ser Leu Phe Thr Cys Gln Asn Gly Ile Val Trp Thr
     50                  55                  60

Asn Gly Thr His Val Thr Tyr Arg Lys Asp Thr Arg Tyr Lys Leu Leu
 65                  70                  75                  80

Gly Asp Leu Ser Arg Arg Asp Val Ser Leu Thr Ile Glu Asn Thr Ala
                 85                  90                  95

Val Ser Asp Ser Gly Val Tyr Cys Cys Arg Val Glu His Arg Gly Trp
             100                 105                 110

Phe Asn Asp Met Lys Ile Thr Val Ser Leu Glu Ile Val Pro Pro Lys
             115                 120                 125

Val Thr Thr Thr Pro Ile Val Thr Thr Val Pro Thr Val Thr Thr Val
         130                 135                 140

Arg Thr Ser Thr Thr Val Pro Thr Thr Thr Val Pro Met Thr Thr
145                 150                 155                 160

Val Pro Thr Thr Thr Val Pro Thr Thr Met Ser Ile Pro Thr Thr Thr
                 165                 170                 175

Thr Val Leu Thr Thr Met Thr Val Ser Thr Thr Thr Ser Val Pro Thr
             180                 185                 190

Thr Thr Ser Ile Pro Thr Thr Thr Ser Val Pro Val Thr Thr Thr Val
             195                 200                 205

Ser Thr Phe Val Pro Pro Met Pro Leu Pro Arg Gln Asn His Glu Pro
         210                 215                 220

Val Ala Thr Ser Pro Ser Ser Pro Gln Pro Ala Glu Thr His Pro Thr
225                 230                 235                 240

Thr Leu Gln Gly Ala Ile Arg Arg Glu Pro Thr Ser Ser Pro Leu Tyr
                 245                 250                 255

Ser Tyr Thr Thr Asp Gly Asn Asp Thr Val Thr Glu Ser Ser Asp Gly
             260                 265                 270

Leu Trp Asn Asn Asn Gln Thr Gln Leu Phe Leu Glu His Ser Leu Leu
             275                 280                 285

Thr Ala Asn Thr Thr Lys Gly
         290                 295

<210> SEQ ID NO 7
<211> LENGTH: 4
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Cys Cys Cys
1
```